United States Patent
Puri et al.

(10) Patent No.: US 10,849,960 B2
(45) Date of Patent: Dec. 1, 2020

(54) SYNERGISTIC COMBINATION OF IL-4, INTERFERON GAMMA, AND INTERFERON ALPHA IN TREATING OVARIAN CANCER

(71) Applicant: The United States of America, as represented by the Secretary, Department of Health and Human Services, Silver Spring, MD (US)

(72) Inventors: Raj K. Puri, Potomac, MD (US); Kathryn C. Zoon, Kensington, MD (US); Syed R. Husain, Gaithersburg, MD (US); Daniel S. Green, Silver Spring, MD (US)

(73) Assignee: The United States of America, as represented by the Secretary, Department of Health and Human Services, Silver Spring, MD (US)

(*) Notice: Subject to any disclaimer, the term of this patent is extended or adjusted under 35 U.S.C. 154(b) by 0 days.

(21) Appl. No.: 16/645,431

(22) PCT Filed: Sep. 7, 2018

(86) PCT No.: PCT/US2018/049919
§ 371 (c)(1),
(2) Date: Mar. 6, 2020

(87) PCT Pub. No.: WO2019/051204
PCT Pub. Date: Mar. 14, 2019

(65) Prior Publication Data
US 2020/0282020 A1     Sep. 10, 2020

Related U.S. Application Data

(60) Provisional application No. 62/556,049, filed on Sep. 8, 2017.

(51) Int. Cl.
| | | |
|---|---|---|
| *A61K 38/17* | (2006.01) | |
| *A61K 38/21* | (2006.01) | |
| *C07K 16/28* | (2006.01) | |
| *A61P 35/00* | (2006.01) | |
| *A61K 35/15* | (2015.01) | |
| *A61K 45/06* | (2006.01) | |

(52) U.S. Cl.
CPC ............ *A61K 38/212* (2013.01); *A61K 35/15* (2013.01); *A61K 38/1793* (2013.01); *A61K 38/217* (2013.01); *A61P 35/00* (2018.01); *C07K 16/28* (2013.01); *A61K 45/06* (2013.01)

(58) Field of Classification Search
CPC . A61K 38/212; A61K 38/217; A61K 38/2026
See application file for complete search history.

(56) References Cited

U.S. PATENT DOCUMENTS

2017/0202922 A1    7/2017   Puri

OTHER PUBLICATIONS

Critchley-Thorne et al. PNAS, Jun. 2, 2009, vol. 106, No. 22, pp. 9010-9015.*
Kioi et al, Cancer Research, 2005, 65(18):8388-8396.*
Di Franco et al. Frontiers in Immunology, 26, Jul. 2017, vol. 8, Article 878, pp. 1-13.*
Baron et al., "Clinical Model: Interferons Activate Human Monocytes to an Eradicative Tumor Cell Level In Vitro," *J Interferon Cytokine Res.*, 27:157-163, 2007.
Baron et al., "Near Eradication of Clinically Relevant Concentrations of Human Tumor Cells by Interferon-Activated Monocytes In Vitro," *J Interferon Cytokine Res.*, 31:569-573, Nov. 7, 2011.
Pearson et al., "Enhanced Therapeutic Efficacy Against an Ovarian Tumor Xenograft of Immunotoxins Used in Conjunction with Recombinant α-Interferon," *Cancer Res.*, 50:6379-6388, 1990.
International Search Report and Written Opinion dated Dec. 14, 2018, for PCT/US2018/049919 (10 pages).
Debinski et al., "Interleukin-4 Receptors Expressed on Tumor Cells May Serve as a Target for Anticancer Therapy Using Chimeric *Pseudomonas exotoxin*," *Int J. Cancer*, 58:7440748, 1994.
Jemal et al., "Cancer statistics," *CA Cancer J Clin.*, 55:10-30, 2005.
Kawakami et al., "Interleukin 4 Receptor on Human Lung Cancer: A Molecular Target for Cytotoxin Therapy," *Clin Cancer Res.*, 8:3503-3511, 2002.
Markman et al., "Second-line Platinum Therapy in Patients With Ovarian Cancer Previously Treated With Cisplatin," *J Clin Oncol.*, 9:389-393, 1991.
Nakashima et al., "Potent Antitumor Effects of Combination Therapy With IFNs and Monocytes in Mouse Models of Established Human Ovarian and Melanoma Tumors," *Cancer Immunol Immunother*, 61:1081-1092, 2012.
Obiri et al., "Expression of High-Affinity IL-4 Receptors on Human Melanoma, Ovarian and Breast Carcinoma Cells," *Clin Exp Immunol.*, 95:144-155, 1994.
Puri et al., "Human Neurological Cancer Cells Express interleukin-4 (IL-4) Receptors Which Are Targets for the Toxic Effects of IL4-Pseudomonas Exotoxin Chimeric Protein," *Int J. Cancer*, 58:574-581, 1994.
Sasaki et al., "Identification of the Interleukin 4 Receptor ■ Gene as a Direct Target for p73," *Cancer Res.*, 63:8145-8152, 2003.

* cited by examiner

*Primary Examiner* — Prema M Mertz
(74) *Attorney, Agent, or Firm* — Klarquist Sparkman, LLP

(57) ABSTRACT

Methods and compositions are disclosed for treating a subject with a cancer. The compositions can include a chimeric molecule comprising an agent that specifically binds the interleukin 4 receptor (IL-4R) and a toxic moiety, an interferon alpha (IFNα), and an interferon gamma (IFNγ). In some non-liming embodiments, the compositions can also include monocytes. The methods disclosed herein include administering a therapeutically effective amount of the compositions taught herein to a subject with cancer, thereby treating the cancer in the subject, wherein cells in the cancer express IL-4R. In some non-liming embodiments, the methods can also include administering monocytes.

17 Claims, 10 Drawing Sheets

Specification includes a Sequence Listing.

FIG. 2

| OVCAR-5 | | A2780 | |
|---|---|---|---|
| IL-4PE (ng/mL)/IFNs (ng/mL) | CI Values | IL-4PE (ng/mL)/IFNs (ng/mL) | CI Values |
| 0.04/0.16 | 1.25 (A) | 0.32/1.6 | 0.50 (S) |
| 0.2/0.8 | 0.4 (S) | 1.6/8 | 0.06 (S) |
| 1/4 | 0.11 (S) | 4/20 | 0.02 (S) |
| 5/20 | 26.2E-06 (S) | 40/200 | 4.5E-04 (S) |
| EC50 | 0.58 (S) | EC50 | 0.24 (S) |

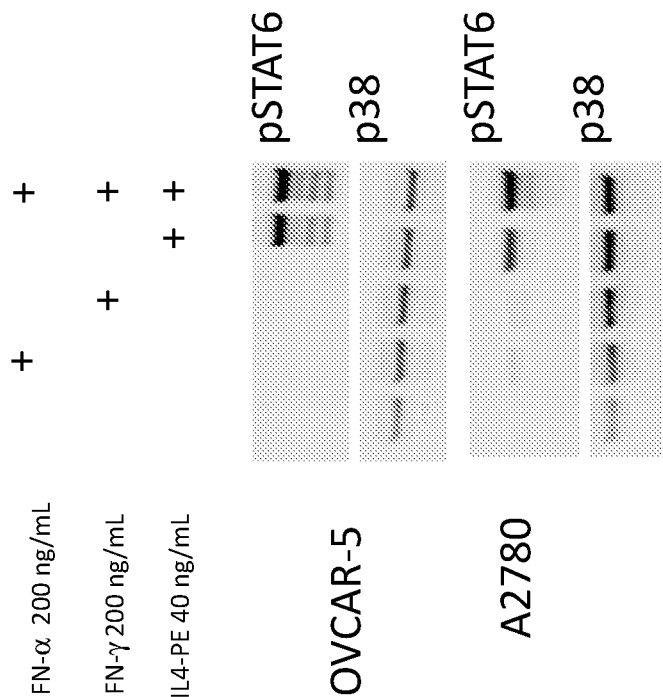
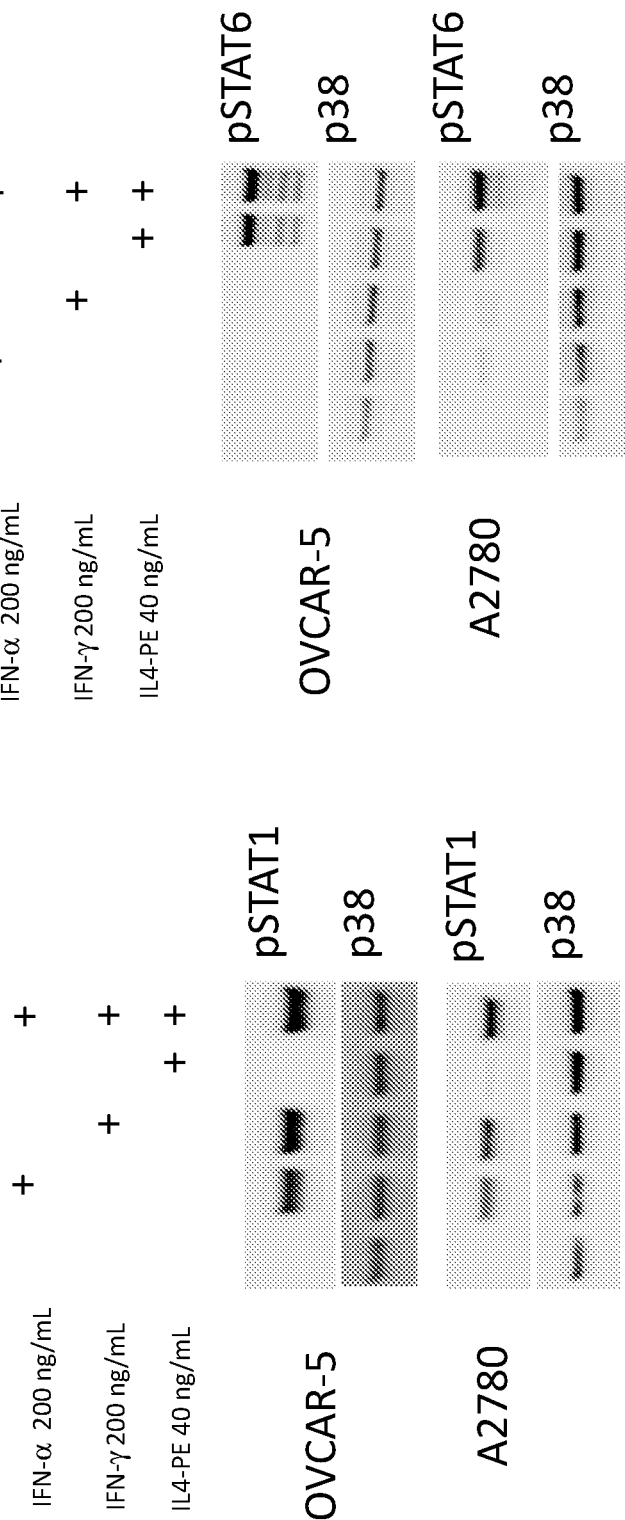

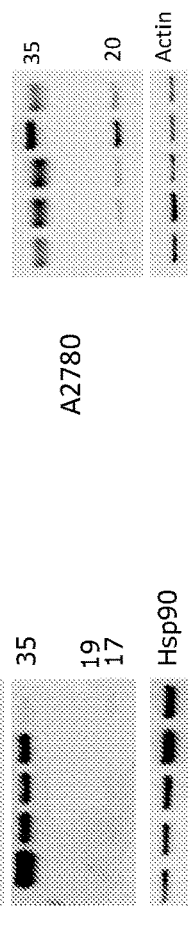
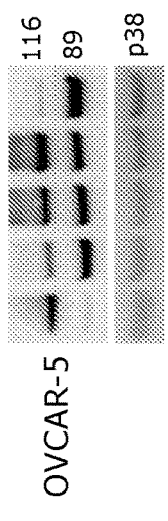
FIG. 8A  PARP
FIG. 8B  Caspase 3
FIG. 8C  Caspase 7

SYNERGISTIC COMBINATION OF IL-4, INTERFERON GAMMA, AND INTERFERON ALPHA IN TREATING OVARIAN CANCER

CROSS REFERENCE TO RELATED APPLICATIONS

This application is the U.S. National Stage of International Application No. PCT/US2018/049919, filed Sep. 7, 2018, which was published in English under PCT Article 21(2), which claims the benefit of U.S. Provisional Application No. 62/556,049, filed Sep. 8, 2017, which is herein incorporated by reference in its entirety.

FIELD

This relates to the treatment of cancer, specifically to the use of a combination of interferon alpha (IFNα), interferon gamma (IFNγ), and a chimeric molecule that includes a toxic moiety and an IL-4R-binding agent.

BACKGROUND

Ovarian cancer is the fifth most common cause of cancer death among women in the US according to the American Cancer Society. Surgery is the main treatment, and it removes all visible disease in the abdomen, which is commonly referred to as surgical debulking. Chemotherapy may then be used to destroy remaining ovarian cancer cells. Despite optimal surgery and chemotherapy, approximately 80% of patients with epithelial ovarian cancer will relapse after first-line chemotherapy (Markman et al., *J Clin Oncol.*, 9(3):389-393, 1991). Targeted therapies are also used for some types of ovarian cancer. There is a good chance of a cure if ovarian cancer is diagnosed and treated when the disease is at an early stage (i.e., confined to the ovary and has not spread).

Unfortunately, the majority of ovarian cancer patients (70%) are diagnosed at an advanced stage (Stage III or IV) of the disease, at which time the primary tumor has metastasized and few therapeutic options are available. The incidence of distant metastasis at diagnosis in patients with ovarian cancer is highest among all cancer types (Jemal et al., *CA Cancer J Clin.*, 55:10-30, 2005). Despite advances in the treatment of many malignant cancers, ovarian cancer remains largely refractory to current treatments (Ledermann, et al., *Ann Oncol*, 24:6, 24-32, 2013). Thus, a need remains for new agents and combinations of treatments for ovarian cancer.

SUMMARY

Methods and compositions are disclosed for treating a subject with a cancer, wherein cells in the cancer express IL-4R. In some embodiments, the compositions include a chimeric molecule that includes an agent that specifically binds the interleukin 4 receptor (IL-4R) and a toxic moiety or a polynucleotide encoding the chimeric molecule; an interferon alpha (IFNα) polypeptide, an effective fragment thereof, or a variant thereof or a polynucleotide encoding the IFNα polypeptide, the effective fragment thereof, or the variant thereof; and an interferon gamma (IFNγ) polypeptide, an effective fragment thereof or a variant thereof, or a polynucleotide encoding the IFNγ polypeptide, the effective fragment thereof, or the variant thereof. These compositions are of use for treating a subject with a cancer, wherein the cells in the cancer express IL-4R.

In other embodiments, methods are disclosed that include administering to the subject a therapeutically effective amount of a composition, including a chimeric molecule that includes an agent that specifically binds IL-4R and a toxic moiety or a polynucleotide encoding the chimeric molecule; an IFNα polypeptide, an effective fragment thereof, or a variant thereof or a polynucleotide encoding the IFNα polypeptide, the effective fragment thereof, or the variant thereof; and an IFNγ polypeptide, an effective fragment thereof, or a variant thereof or a polynucleotide encoding the IFNγ polypeptide, the effective fragment thereof, or the variant thereof.

The foregoing and other objects, features, and advantages of the invention will become more apparent from the following detailed description, which proceeds with reference to the accompanying figures.

BRIEF DESCRIPTION OF THE DRAWINGS

FIG. 2: Synergistic antitumor effect of combination of IL4-PE and IFNs in ovarian cancer cell lines. Synergy analysis is presented as a combinatorial index (CI) number for each concentration group tested, where A indicates antagonism and S is synergistic. Values were generated from data presented in FIGS. 1A-1B using CompuSyn software.

(FIG. 3A) Schematic of dosing: $2 \times 10^6$ A2780 cells were injected IP on Day 0. Animals were treated with either IFNα(SYLATRON®) and IFNγ (20 ng each per mouse), IL4-PE (1 μg/mouse), both IFNs and IL4-PE or saline intraperitoneally with a total volume of 100 μL on days 5, 7, and 9. (FIG. 3B) Kaplan Meir survival curves for the combination of all three experiments. Graphs show survival of groups treated with saline (untreated, dashed line), IL4-PE (dashed line with dots), IFNs (continuous line), or IFNs and IL4-PE (densely dashed line).

FIGS. 6A-6B: Western blot analysis of IFN and IL4-PE STAT activation. (FIG. 6A) Western blots for phosphorylated STAT1 in OVCAR-5 and A2780 cells stimulated with IFNα2a, IFNγ, IL4-PE, or all three agents for 20 minutes at the highest concentrations from FIGS. 1A-1B (representative of three separate experiments). (FIG. 6B) Western blots for phosphorylated STAT6 in OVCAR-5 and A2780 cells stimulated with IFNα2a, IFN, IL4-PE, or all three agents for 20 minutes (representative of three separate experiments). P38 protein kinase was used as a loading control.

FIGS. 8A-8C: Western blot analysis of IFN and IL4-PE induction of apoptosis-related proteins. Indicated cell lines were cultured with IFNα2a, IFNγ, or IL4-PE alone or all three drugs for 33 hours. Cells were lysed and probed for indicated protein products (FIG. 8A) PARP and cleaved PARP, (FIG. 8B) caspase-3 and cleaved caspase-3, and (FIG. 8C) caspase-7 and cleaved caspase-7.

SEQUENCE LISTING

Figure 1A:
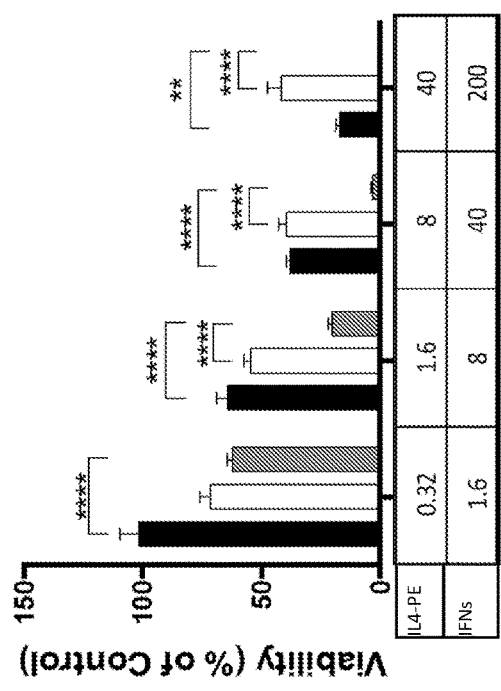
FIGS. 1A-1B: Treatment of ovarian cancer cell lines with IFNα2a, IFNγ, and IL4-PE. OVCAR-5 (FIG. 1A) and A2780 (FIG. 1B) cells were treated with increasing concentrations of IL4-PE (black bars), IFNα, and IFNγ (open bars) or the combination of IL4-PE, IFNα, and IFNγ (grey bar). Concentrations are presented on the abscissae with the IL4-PE concentration first and the IFNα and IFNγ concentrations second. Cell viability is presented as percent of the control on the ordinate. Statistics were calculated by 2-way ANOVA with P-values≤0.05 (*P<0.05, P<0.01, *P<0.001, ****P<0.0001).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 5, 2020, 30.4 KB, which is incorporated by reference herein. In the accompanying sequence listing:

SEQ ID NO: 2 is an amino acid sequence of an IFNα.
SEQ ID NO: 3 is an amino acid sequence of an IFNγ.
SEQ ID NO: 4 is an amino acid sequence of an IFNγ.
SEQ ID NO: 5 is a nucleic acid sequence of an IFNα.
SEQ ID NO: 6 is a nucleic acid sequence of an IFNα.
SEQ ID NO: 7 is a nucleic acid sequence of an IFNγ.
SEQ ID NO: 8 is a nucleic acid sequence of an IFNγ.
SEQ ID NO: 9 is an amino acid sequence of an IL-4.
SEQ ID NO: 10 is an amino acid sequence of an IL-4.
SEQ ID NO: 11 is a nucleic acid sequence of an IL-4.
SEQ ID NO: 12 is a nucleic acid sequence of an IL-4.
SEQ ID NO: 13 is an amino acid sequence of a PE.
SEQ ID NO: 14 is a nucleic acid sequence of a PE.
SEQ ID NO: 15 is an amino acid sequence of an IL4-PE38KDEL.
SEQ ID NO: 16 is a nucleic acid sequence of an IL4-PE38KDEL.

DETAILED DESCRIPTION

Methods are needed for the treatment of cancers, where cells in the cancer express IL-4R. These cancers include, but are not limited to, ovarian cancer, lung cancer, liver cancer, melanoma, osteosarcoma, or a brain cancer. With regard to ovarian cancer, the spread (e.g., metastatic spread, including distant metastases, such as in the bone, lung, and brain, for example, as can occur late in the course of the disease) of this cancer is often through the intraperitoneal (IP) route (e.g., through the peritoneum, for example, with extensions into the pelvis). Therefore, IP administration of chemotherapy is a logical approach for ovarian cancer therapy. Intraperitoneal administration of cisplatin-based chemotherapy is effective in both survival and toxicity; however, toxicity is higher when IP administration is used compared with intravenous (IV) administration. While ovarian cancer patients show a positive response to the first line combination chemotherapy of taxane plus carboplatin, many have disease relapse, and immunotherapy with anti-PD1 and anti-PDL1 antibodies has largely been unsuccessful in ovarian cancer patients. With no FDA-approved, second line therapies, patients that have disease relapse have a high mortality rate with an overall cure rate of approximately 30% (Bast et al., *Nat Rev Cancer*, 9:415-428, 2009). Therefore, increasing the number of therapeutic options for the treatment of late stage ovarian cancer is urgently needed.

One of the hallmarks of ovarian cancer is increasing resistance to chemotherapy over time (Ledermann et al., *Ann Oncol*, 24(Suppl 6):24-32, 2013). While the mechanisms of resistance have not been fully elucidated and are highly complex, resistance is partially due to mutations within the cancer cells that result in evasion (Burrell et al., *Nature*, 501:338-345, 2013). The ability to target multiple pathways at the same time is critical for treatment of modern cancers.

The limited efficacy of monotherapy for treating malignant cancers has highlighted the need to use a combination of multiple synergistic therapeutic modalities to achieve total remission. While single agent therapy can be beneficial, combination therapy provides the best treatment options for metastatic ovarian cancer (Parmar et al., *Lancet*, 361:2099-2106, 2003). The ability to simultaneously target distinct cellular pathways or targets may increase cell death or inhibit tumor cell growth. The use of multiple drugs also decreases the potential for the cancer to mutate and become drug resistant (see, for example, Jensen et al., *Br J Cancer*, 75:869-877, 1997).

Methods and compositions are disclosed for treating a subject with a cancer, where cells in the cancer express the interleukin 4 receptor (IL-4R). The subject can be as a human or a veterinary animal. The compositions can include a chimeric molecule comprising an agent that specifically binds IL-4R and a toxic moiety, or a polynucleotide encoding the chimeric molecule; an interferon alpha (IFNα) polypeptide, an effective fragment thereof, or a variant thereof or a polynucleotide encoding the IFNα polypeptide, the effective fragment thereof, or the variant thereof; and an interferon gamma (IFNγ) polypeptide, an effective fragment thereof, or a variant thereof or a polynucleotide encoding the IFNγ polypeptide, the effective fragment thereof, or the variant thereof. In some embodiments, the IFNα and/or IFNγ polypeptide or the effective fragment or the variant thereof can be human polypeptide(s). The methods disclosed herein include administering a therapeutically effective amount of these compositions. The compositions can be administered systemically or locally.

In some embodiments, the agent that specifically binds IL-4R can be an IL-4 polypeptide, an effective fragment thereof, or a variant thereof. In additional embodiments, the IL-4 can be human. In other embodiments, the variant of the IL-4 polypeptide can be a circularly permuted IL-4 polypeptide. Exemplary IL-4 polypeptides can include amino acid sequences at least 95% or 100% identical to SEQ ID NO: 1. In other embodiments, the agent that specifically binds the IL-4R can be an antibody that specifically binds IL-4R or an antigen-binding fragment thereof. In certain non-limiting examples, the antibody can be a monoclonal antibody. In other non-limiting examples, the antigen-binding fragment is a Fab', (Fab')$_2$, single chain (sc)Fv, or disulfide stabilized (ds)Fv.

In certain embodiments, the toxic moiety can be a *Pseudomonas* exotoxin (PE), ricin A, abrin, ribotoxin, ribonuclease, saporin, calicheamycin, Diphtheria toxin, botulinum toxin, pokeweed antiviral toxin, bryodin 1, *Clostridium perfringens* enterotoxin (CPE), Cholera toxin, BAD (BCL-2 associated death prompter protein), ribosome-inactivating toxins or a cytotoxic fragment thereof. In some non-limiting examples the toxic moiety can be a PE polypeptide or a cytotoxic fragment thereof. In additional non-limiting examples, the PE polypeptide can be wild type PE, PE38, or PE40. In other non-limiting examples, the chimeric molecule can include a circularly permuted IL-4 and a PE or a cytotoxic fragment thereof. In other non-limiting examples, the toxic moiety can be a chemotherapeutic agent, such as, but not limited to, taxane, carboplatin, cyclophosphamide, and/or doxorubicin.

In some embodiments, the subject can have a solid or malignant tumor, an ovarian cancer, a lung cancer, a liver cancer, a melanoma, an osteosarcoma, or a brain cancer. In certain non-limiting examples, the cancer is ovarian cancer. In other examples, the methods can include also administering to the subject another therapy, such as surgery or another therapeutic agent, such as chemotherapy, hormone therapy, radiation therapy, immunotherapy, and/or a vaccine. In specific, non-limiting examples, the immunotherapy includes adoptive cell transfer (e.g., using monocytes).

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural cells and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 8, 2017. All references and GENBANK® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Administration: To provide or give a subject a therapeutic intervention, such as a therapeutic drug (e.g., IFNα, IFNγ, and IL4-PE for a subject with cancer), procedure, or protocol. Exemplary routes of administration for drug therapy include, but are not limited to, oral, subcutaneous, intramuscular, intradermal, intraperitoneal, intratumoral, intraprostatic, intravenous, sublingual, rectal, transdermal, intranasal, and inhalation routes.

Adoptive cell transfer: An immunotherapy that includes transferring cells into a patient (e.g., Rosenberg et al., *Nat Rev Cancer,* 8(4): 299-308, 2008; Green et al., *J Translational Medicine,* 16(1):196, 2018; Langan et al., *J Immunother,* 34(4): 397-4-02, 2011, all of which are incorporated herein by reference in their entireties). The cells can be from the patient (e.g., autologous) or another individual (e.g., allogenic) and can include any type of cell, for example, leukocytes, such as monocytes (including monocyte-derived cells, such as macrophages), T cells, and B cells. Common protocols include culturing and expanding cells of interest (e.g., tumor-destroying leukocytes) and then transferring the cells to the patient (e.g., via infusion). In some examples, additional agents can be administered, such as immunodepleting agents (e.g., a preparative regimen prior to administration of the cells of interest, such as a regimen that includes administration of cyclophosphamide and/or fludarabine), and/or an agent co-administered with the cells of interest (e.g., an agent that enhances efficacy of the cells of interest, such as IL-2).

Agent: Any protein, nucleic acid molecule, compound, small molecule, organic compound, inorganic compound, or other molecule of interest. Agent can include a therapeutic agent, a diagnostic agent, or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent (such as IFNα, IFNγ, and IL4-PE) significantly reduces cancer.

Antibody: A polypeptide ligand including at least a light chain or heavy chain immunoglobulin variable region that specifically recognizes and binds an epitope of an antigen, such as IL-4R. Antibodies are composed of a heavy and a light chain, each of which has a variable region, termed the variable heavy (VH) region and the variable light (VL) region. Together, the VH region and the VL region are responsible for binding the antigen recognized by the antibody.

This includes intact immunoglobulins and the variants and portions thereof that are well-known in the art, such as Fab' fragments, F(ab)'2 fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms, such as chimeric antibodies (for example, humanized murine antibodies), or heteroconjugate antibodies (such as, bispecific antibodies). See also, Pierce Catalog and Handbook, 1994-

1995 (Pierce Chemical Co., Rockford, Ill.); Kuby, J., Immunology, 3rd Ed., W.H. Freeman & Co., New York, 1997.

Typically, a naturally occurring immunoglobulin has heavy (H) chains and light (L) chains interconnected by disulfide bonds. There are two types of light chain: lambda and kappa. There are five main heavy chain classes (or isotypes) that determine the functional activity of an antibody molecule: IgM, IgD, IgG, IgA, and IgE.

Each heavy and light chain contains a constant region and a variable region (the regions are also known as "domains"). In combination, the heavy and light chain variable regions specifically bind the antigen. Light and heavy chain variable regions contain a "framework" region interrupted by three hypervariable regions, which are also referred to as "complementarity-determining regions" or "CDRs." The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online. The sequences of the framework regions of different light or heavy chains are relatively conserved within a species. The framework region of an antibody, which is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. An antibody that binds IL-4R will have a specific VH region and VL region sequence and, thus, specific CDR sequences. Antibodies with different specificities (such as different combining sites for different antigens) have different CDRs. Although the CDRs that vary among antibodies, only a limited number of amino acid positions within the CDRs are directly involved in antigen binding. These positions within the CDRs are referred to as specificity determining residues (SDRs).

References to "VH" or "VH" refer to the variable region of an immunoglobulin heavy chain, including that of an Fv, scFv, dsFv, or Fab. References to "VL" or "VL" refer to the variable region of an immunoglobulin light chain, including that of an Fv, scFv, dsFv, or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit, or goat) that induces the B lymphocytes to produce IgG immunoglobulins specific for the antigen that are then purified from the mammal's serum.

A "chimeric antibody" has framework residues from one species, such as human, and CDRs (which generally confer antigen binding) from another species, such as a murine antibody that specifically binds IL-4R.

A "humanized" immunoglobulin is an immunoglobulin that includes a human framework region and one or more CDRs from a non-human (for example, a mouse, rat, or synthetic) immunoglobulin. The non-human immunoglobulin providing the CDRs is termed a "donor," and the human immunoglobulin providing the framework is termed an "acceptor." In one embodiment, all of the CDRs are from the donor immunoglobulin in a humanized immunoglobulin. Constant regions need not be present, but if they are, they must be substantially identical to human immunoglobulin constant regions (e.g., at least about 85-90%, such as about 95% or more identical). Hence, all parts of a humanized immunoglobulin, except possibly the CDRs, are substantially identical to corresponding parts of natural human immunoglobulin sequences. Humanized immunoglobulins can be constructed by means of genetic engineering (see, e.g., U.S. Pat. No. 5,585,089).

Binding or stable binding: An association between two substances or molecules, such as the hybridization of one nucleic acid molecule to another (or itself), the association of an antibody with a peptide, or the association of a protein with another protein or nucleic acid molecule.

Biological activity: Describes the beneficial or adverse effects of an agent on living matter. When the agent is a complex chemical mixture, this activity is exerted by the substance's active ingredient or pharmacophore but can be modified by the other constituents. Activity is generally dose-dependent, and it is not uncommon for effects to range from beneficial to adverse for one substance among low to high doses.

Brain cancer: A brain tumor or intracranial neoplasm due to abnormal cells that form within the brain. Includes two main types of tumors: malignant or cancerous tumors and benign tumors. Cancerous tumors can be divided into primary tumors that begin in the brain, and secondary tumors that have spread from elsewhere are known as brain metastasis tumors. Examples of common primary cancerous tumors include astrocytomas, meningiomas, and oligodendrogliomas.

Brain tissue is composed of two broad classes of cells: neurons and glia. These two types are present at equal number in the brain as a whole; however, glial cells outnumber neurons by approximately 4 to 1 in the cerebral cortex. Several types of glia are present and perform a number of critical functions, including structural support, metabolic support, insulation, and development. Primary glial cell tumors are referred to as gliomas and often are malignant by the time they are diagnosed.

Cancer: Includes the pathology of cancer (i.e., all such phenomena that compromise the well-being of the subject). This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. "Metastatic disease" refers to cancer cells that have left the original tumor site and migrate to other parts of the body for example via the bloodstream or lymph system. Cancer cells can spread locally or through the bloodstream and lymphatic system to other parts of the body. Examples of various cancers are described herein and include, but are not limited to, glioblastoma, breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Chemotherapeutic agent or Chemotherapy: Any chemical or biological agent with therapeutic usefulness in the treatment of diseases characterized by abnormal cell growth. Such diseases include tumors, neoplasms, and cancer as well as diseases characterized by hyperplastic growth, such as psoriasis. In one embodiment, a chemotherapeutic agent is an agent of use in treating ovarian cancer. In one example, a chemotherapeutic agent is a radioactive compound. One of skill in the art can readily identify a chemotherapeutic agent of use (see, e.g., Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993, incorporated herein by reference). Chemical chemotherapeutic agents used for treating cancer, such as ovarian cancer, include, but are not limited to, taxane, carboplatin, cyclophosphamide, and/or doxorubicin. Combination chemotherapy is the administration of more than one agent (such as more than one chemical chemotherapeutic agent) to treat cancer.

Chimera: A molecule (e.g., nucleic acid or protein) composed of parts with different origins (such as at least two nucleic acids or polypeptides) that are joined or linked to form a single continuous molecule, but are typically unjoined in their native state. A chimera may include nucleic acids or polypeptides that are joined end-to-end (for example, the amino-terminus of one sequence is joined to the carboxyl-terminus of a second sequence) or may include a sequence from one molecule that is embedded within that of another molecule (for example, the amino-terminus and carboxyl-terminus of the chimera are from one molecule, while an intervening sequence comes from another molecule).

A chimera may include a chimeric protein (also known as a fusion protein), for example a protein that is composed of amino acids from more than one protein. A chimera may also include a chimeric nucleic acid composed of nucleic acid sequences from more than one source, such as a chimeric nucleic acid which encodes a chimeric protein. For example, a chimera may include a protein that specifically binds IL-4R and a toxic moiety, such as IL4-PE. In other examples, a chimera may include a polynucleotide encoding a protein that specifically binds IL-4R and a toxic moiety, such as IL4-PE.

Circular Permutation: Circularly permuted molecules, which may include DNA, RNA, and protein, are single-chain molecules with their normal termini fused, often with a linker, to produce a circularly fused molecule, and then the circularly fused molecule is opened at another location with new termini at another position. See U.S. Pat. No. 6,011,002; Goldenberg et al., *J. Mol. Biol.*, 165: 407-413, 1983; and Pan et al., *Gene*, 125: 111-114, 1993, all of which are incorporated by reference herein. Circular permutation preserves the sequence and identity of the amino acids of a protein, while generating new termini at different locations.

It will be appreciated that, while circular permutation is described in terms of linking the two ends of a protein and then cutting the circularized protein, these steps are not actually required to create the end product. A protein synthesized de novo would be equivalent to a protein made by circularization and cutting (see, e.g., U.S. Pat. No. 6,011,002, incorporated by reference herein).

Circularly permuted molecules can be joined with other molecules to form a chimeric molecule. Examples of such molecules include circularly permuted ligands (e.g., IL-4) or antibodies (e.g., an antibody that specifically binds IL-4R) and toxin molecules (e.g., PE or variants thereof) that are joined to form a single molecule (e.g., IL4-PE).

Conservative variants: "Conservative" amino acid substitutions are those substitutions that do not substantially affect or decrease a function of a protein, such as the ability of the protein to exert a synergistic effect in the treatment cancer when administered to a subject. The term conservative variation also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the protein, such as the ability to induce a synergistic response when administered to a subject. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Cytokine: Proteins made by cells that affect the behavior of the same cell and/or other cells, such as lymphocytes. In one embodiment, a cytokine is a chemokine, a molecule that affects cellular trafficking. In another embodiment, a cytokine alters the maturation of lymphocytes, and influences isotype switching by B cells. Cytokines can further act through receptors. Interleukins, such as interleukin 4 (IL-4), and interferons are cytokines.

Cytotoxicity: The toxicity of a molecule, such as an immunotoxin, to the cells intended to be targeted, as opposed to the cells of the rest of an organism. One of skill in the art would recognize that many toxins exert cytotoxicity, including *Pseudomonas* exotoxin (PE), ricin A, abrin, ribotoxin, ribonuclease, saporin, calicheamycin, Diphtheria toxin, botulinum toxin, pokeweed antiviral toxin, bryodin 1, *Clostridium perfringens* enterotoxin (CPE), Cholera toxin, BAD (BCL-2 associated death prompter protein), ribosome-inactivating toxins, other bacterial toxins, and derivatives of plant or animal toxins or a cytotoxic fragment thereof.

Fc polypeptide: The polypeptide comprising the constant region of an antibody excluding the first constant region immunoglobulin domain. The Fc region generally refers to the last two constant region immunoglobulin domains of IgA, IgD, and IgG as well as the last three constant region immunoglobulin domains of IgE and IgM. An Fc region may also include part or all of the flexible hinge N-terminal to these domains. For IgA and IgM, an Fc region may or may not comprise the tailpiece and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region typically includes residues C226 or P230 through the carboxyl-terminus, wherein the numbering is according to the EU index as in Kabat. For IgA, the Fc region comprises immunoglobulin domains Calpha2 and Calpha3 (Cα2 and Cα3) and the lower part of the hinge between Calpha1 (Cα1) and Cα2.

Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80% or about 90% or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose the Fc region as defined above. The Fc region may refer to this region in isolation or this region in the context of a fusion protein.

Heterologous: Originating from a different genetic sources or species. For example, a chimeric nucleic acid that includes nucleic acids from two (or more) different genetic sources or from two (or more) otherwise separated segments of sequence from a single genetic source is considered a heterologous nucleic acid. Similarly, a polypeptide including peptides from two (or more) different proteins from a single genetic source or two (or more) proteins from different genetic sources (such as a fusion protein) is considered a heterologous polypeptide. For example, a chimeric protein that includes IL-4 and PE or a nucleic acid encoding the chimera is a heterologous protein or nucleic acid, respectively.

Immunotherapy: Use of the immune system for treatment of a disease or condition (e.g., cancer, such as an ovarian cancer, a lung cancer, a liver cancer, a melanoma, an osteosarcoma, a brain cancer, a solid tumor, or a malignant tumor) Immunotherapy can include using any agent or protocol that involves the immune system for treatment (e.g., cell-based, protein-based, and/or nucleic acid-based therapies as well as therapies based on other compounds, for example, compounds found in fungi, such as polysaccharides). In some examples, immunotherapy includes administering a cell-based therapy, such as monocytes (e.g., in combination with IFNα, IFNγ, and a chimeric molecule that includes a toxic moiety and an IL-4R-binding agent, such as IL4-PE), for example, using adoptive cell transfer.

Inhibiting or treating a disease: Inhibiting the full development of a disease or condition, for example, in a subject who is at risk for a disease such as cancer or metastasis or recurrence thereof. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, reduced tumor burden, reduce metastases, a slower progression of the disease, an improvement in the overall health or well-being of the subject, or by other parameters well known in the art that are specific to the particular disease. "Prophylaxis" is a treatment administered to a subject who does not exhibit signs of a disease or exhibits only early signs for the purpose of decreasing the risk of developing pathology.

Interferon (IFN): Pleiotropic cytokines that regulate cell cycle, cellular differentiation, cell proliferation and antiviral, bacterial, fungal, and parasitic responses and specifically bind interferon receptors (Platanias, *Nat Rev Immunol,* 5:375-386, 2005). The interferons include IFNα, IFNβ, IFN γ, IFN-ε, IFN-κ, IFN-ω, and IFN-2 While IFNα and IFNγ production is limited to a small number of cell types, primarily immune cells, the receptors are expressed on almost every cell in the body. Interferon-based drugs are used to treat malignancies and are the subject of ongoing clinical trials (Bekisz et al., *J Interferon Cytokine Res,* 33:154-161, 2013; Kavanagh et al., Blood 128:2824-2833, 2016; Pogue et al., *PLoS One,* 11:e0162472, 2016).

IFN alpha (IFNα): Also known as IFNA, leukocytic alpha-interferon, and IFN leukocyte (IFL; e.g., OMIM 147660), IFNα is a cytokine that binds the IFNα receptor (IFNαR) and exhibits antiviral activity. IFNα is primarily expressed by leukocytes, such as dendritic cells (e.g., plasmacytoid dendritic cells) and B cells, and has been studied as an immunotherapeutic drug by providing an effective antineoplastic- and antiviral-immune response. IFN-α drugs (e.g., INTRON-A®, ROFERON-A®, and SYLATRON®) are used in the treatment of a number of cancers (e.g., hairy cell leukemia and melanoma).

IFNα sequences are publicly available. GENBANK® Accession Nos. AAA52724.1, CAA25091.1, and AAA37886.1, incorporated herein by reference, provide exemplary human, rat, and mouse IFNα protein sequences, and GENBANK® Accession Nos. NM_024013.2, NM_001014786.1, and NM_010502.2, incorporated herein by reference, provide exemplary human, rat, and mouse IFNα nucleotide sequences, respectively.

IFN gamma (IFNγ): Also known as IFNG, IFG, IFN immune (IFI; e.g., OMIM 147570), IFNγ is a cytokine that binds the IFNγ receptor (IFNγR) and exhibits antiviral, antibacterial, and antiprotozan activity. IFNγ is primarily expressed by leukocytes, such as T cells and natural killer cells. In ovarian cancer studies, IFNα has also been used in combination with IFNγ as anti-cancer agents. IFN-γ drugs (e.g., ACTIMMUNE®) are already used clinically and are currently undergoing clinical trials for treatment of cancer, such as glioma and melanoma.

IFNγ sequences are publicly available. For example, GENBANK® Accession Nos. AAB59534.1, AAA41362.1, and ACR22511.1, incorporated by reference herein, disclose exemplary human, rat, and mouse IFNγ protein sequences, and GENBANK® Accession Nos. NM_000619.2, NM_138880.2, and NM_008337.4, incorporated by reference herein, disclose exemplary human, rat, and mouse IFNγ nucleotide sequences, respectively. One of ordinary skill in the art can identify additional IFNγ nucleic acid and protein sequences, including IFNγ variants that retain IFNγ biological activity (such as antitumor activity).

Interleukin 4 (IL-4): Also known as B-cell stimulatory factor (BSF1; e.g., OMIM 147780), IL-4 is a cytokine that binds the IL-4 receptor (IL-4Rα) and plays a role in regulating immunity. IL-4 can induce differentiation and proliferation of leukocytes, such as B and T cells. IL-4 is closely related and has functions similar to IL-13. IL-4 has been studied as an immunotherapeutic drug. IL-4R is expressed in certain solid tumors.

IL-4 sequences are publicly available. For example, GENBANK® Accession Nos. CAP72493.1, AAR87867.1, and AAH27514.1, incorporated by reference herein, disclose exemplary human, rat, and mouse IL-4 protein sequences, and M13982.1, NM_201270.1, and M25892.1, incorporated by reference herein, disclose exemplary human, rat, and mouse IL-4 nucleotide sequence, respectively. One of ordinary skill in the art can identify additional IL-4 nucleic acid and protein sequences, including IL-4 variants that retain IL-4 biological activity (such as specifically binding IL-4R).

Interleukin 4 receptor (IL-4R): Also known as CD124 and IL-4R alpha (IL-4Rα; e.g., OMIM 147781), a type I cytokine receptor that can bind IL-4 and IL-13. IL-4R plays a role in regulating antibody production as well as immune cell differentiation and activation. IL-4R is primarily expressed on leukocytes although some solid tumors overexpress IL-4R, such as gliomas and ovarian and non-small cell lung cancers.

IL-4R sequences are publicly available. For example, GENBANK® Accession Nos. CAA36672.1, CAA49528.1, and AAB59727.1, incorporated by reference herein, disclose exemplary human, rat, and mouse IFNγ protein sequences, and X52425.1, X69903.1, and M29854.1, incorporated by reference herein, disclose exemplary human, rat, and mouse IL-4R nucleotide sequences, respectively.

Isolated: An "isolated" biological component has been substantially separated, produced apart from, or purified away from other biological components in the cell of the organism in which the component naturally occurs, such as, other chromosomal and extrachromosomal DNA and RNA and proteins. Nucleic acids, peptides, and proteins that have been "isolated" thus include nucleic acids and proteins purified by standard purification methods. The term also embraces nucleic acids, peptides, and proteins prepared by recombinant expression in a host cell as well as chemically synthesized nucleic acids. For example, isolated proteins, such as IFNα, IFNγ, IL-4, and PE, are proteins that are substantially separated from other types of proteins in a cell.

Liver cancer: A cancer of the liver, including primary liver and secondary liver cancer. In primary liver cancer, the cancer originates in the liver, but in secondary liver cancer (i.e., metastatic liver cancer), the cancer has metastasized into the liver from another originating site in the body. In some embodiments, the primary cancer metastasizes into other organs. Examples of primary liver cancer include hepatocellular carcinoma (i.e., hepatocellular cancer), intrahepatic cholangiocarcinoma (i.e., bile duct cancer), angiosarcoma, hemangiosarcoma, and hepatoblastoma.

Lung cancer: A malignant lung tumor characterized by uncontrolled cell growth in tissues of the lung that can spread beyond the lung through metastasis into nearby tissue or other parts of the body. Examples of lung cancer include non-small cell lung cancer (e.g., adenocarcinomas, squamous cell carcinoma, large cell carcinoma, and large cell neuroendocrine tumors), small cell lung cancer, mesothelioma, and carcinoid tumors.

Malignant: Cells that have the properties of anaplasia invasion and metastasis.

Mammal: Includes both human and non-human mammals. Examples of mammals include, but are not limited to: humans and veterinary and laboratory animals, such as pigs, cows, goats, cats, dogs, rabbits, and mice.

Melanoma: A form of cancer that originates in melanocytes (cells that make the pigment melanin). Melanocytes are found primarily in the skin, but are also present in the bowel and eye. As used herein, "melanoma" refers to any stage of melanoma, or any subtype of melanoma. Examples of melanoma include superficial spreading melanoma, nodular melanoma, lentigo maligna melanoma, acral lentiginous melanoma, desmoplastic melanoma, ocular melanoma, and anorectal melanoma.

Monocyte: A type of leukocyte found in the blood and in tissues, which can differentiate into macrophages or dendritic cells. Monocytes and cells differentiated therefrom are included. Monocytes play various roles in immune function, including phagocytosis, antigen presentation, and cytokine production. Monocytes can also be used as a form of immunotherapy, such as to treat a cancer (e.g., solid or malignant tumor, an ovarian cancer, a lung cancer, a liver cancer, a melanoma, an osteosarcoma, or a brain cancer; Montague and Malcangio, Front Mol Neurosci, 10:397, 2017; Green et al., J Translational Medicine, 16(1):196, 2018, both of which are incorporated herein by reference).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Osteosarcoma (OS) or osteogenic sarcoma (OGS): A cancerous tumor in a bone; an aggressive malignant neoplasm that arises from primitive transformed cells of mesenchymal origin that exhibits osteoblastic differentiation and produces a malignant osteoid. Examples of osteosarcomas include high-grade osteosarcomas, such as osteoblastic, chondroblastic, fibroblastic, mixed, small cell, telangiectatic, high-grade surface (i.e., juxtacortical high grade), pagetoid, extra-skeletal, and post-radiation; intermediate-grade osteosarcomas, such as periosteal (i.e., juxtacortical intermediate grade); and low-grade osteosarcomas, such as parosteal (i.e., juxtacortical low grade) and intramedullary or intraosseous well differentiated (i.e., low-grade central).

Ovarian cancer: A malignant ovarian neoplasm (an abnormal growth located on the ovaries). Cancer of the ovaries includes ovarian carcinoma, papillary serous cystadenocarcinoma (e.g., high-grade serous), mucinous cystadenocarcinoma, endometrioid tumors, Brenner tumors, clear cell carcinoma, unclassified carcinoma, granulosa-thecal cell tumors, Sertoli-Leydig cell tumors, dysgerminoma, and malignant teratoma. The most common type of ovarian cancer is papillary serous carcinoma.

Parenteral: Administered outside of the intestine (e.g., not via the alimentary tract). Generally, parenteral formulations are those that will be administered through any possible mode except ingestion. This term especially refers to injections, whether administered intravenously, intrathecally, intramuscularly, intraperitoneally, intra-vitreously, or subcutaneously, and various surface applications, including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, immunosuppressive agents.

Pharmaceutically acceptable carriers: The pharmaceutically acceptable carriers useful in this disclosure are conventional. *Remington's Pharmaceutical Sciences*, E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, serum albumin (e.g., human serum albumin, "HSA," such as IL4-PE suspended in at least 0.1, 0.2, 0.3, or 0.5% HSA), or the like as a vehicle. For solid compositions (e.g., powder, pill, tablet, or capsule forms), conventional non-toxic solid carriers can include, for example, pharmaceutical grades of mannitol, lactose, starch, or magnesium stearate. In some embodiments, polyethylene glycol is coupled to an IFN (e.g., peginterferona-2b, such as PEG-INTRON®, peginterferona-2a, such as PEGASYS®, and peginterferonλ-1a; see U.S. Pat. No. 8,575,135, incorporated herein by reference). In addition to biologically-neutral carriers, pharmaceutical compositions to be administered can contain minor amounts of non-toxic auxiliary substances, such as wetting or emulsifying agents, preservatives, pH buffering agents, and the like, for example sodium acetate or sorbitan monolaurate.

*Pseudomonas* exotoxin (PE): Also known as Exotoxin A (ETA; e.g., UniProt P11439), PE is an exotoxin produced by *Pseudomonas aeruginosa* that inhibits elongation factor-2 (EF2). PE arrests eukaryotic protein synthesis and induces apoptosis by catalyzing EF2 ADP-ribosylation (catalyzing the transfer of the ADP ribosyl moiety of oxidized NAD onto EF2; see U.S. Pat. No. 6,011,002, incorporated by reference herein). Both preclinical and clinical trials have also studied PE-based immunotoxins as anti-cancer therapies.

The toxin contains three structural domains that act in concert to cause cytotoxicity. Domain 1a (amino acids 1-252) mediates cell binding. Domain II (amino acids 253-364) is responsible for translocation into the cytosol, and domain III (amino acids 400-613) mediates ADP ribosylation of EF2. The function of domain Ib (amino acids 365-399) remains undefined; however, a large portion of domain Ib (e.g., amino acids 365-380) can be deleted without loss of cytotoxicity. See Siegall et al., *J. Biol. Chem*, 264: 14256-14261, 1989, incorporated by reference herein. For example, in the case of B3(Fv)PE38 residues 350 to 394 can be deleted and if replaced with GGGGS SEQ ID NO:54 and are fully active (U.S. Pat. No. 6,011,002, incorporated by reference herein).

PE40 is a truncated derivative of PE (e.g., Pai et al., *Proc. Nat'l Acad. Sci. USA,* 88:3358-62, 1991; Kondo et al., *J. Biol. Chem,* 263:9470-947, 1988; and PCT Pub. No. WO 2003047632, which are incorporated by reference herein). PE35 is a 35 kD carboxyl-terminal fragment of PE in which amino acid residues 1-279 have deleted and the molecule commences with a Met at position 280 followed by amino acids 281-364 and 381-613 of native PE. PE35 and PE40 have been disclosed (e.g., U.S. Pat. Nos. 5,602,095 and 4,892,827 and PCT Pub. No. WO 2003047632, which are incorporated by reference herein). PE38 is a truncated PE pro-protein composed of amino acids 253-364 and 381-613 of PE, which is activated to its cytotoxic form upon processing within a cell (see, e.g., U.S. Pat. No. 5,608,039; Pastan et al., *Biochim. Biophys. Acta*, 1333:C1-C6, 1997; and PCT Pub. No. WO 2003047632, all of which are incorporated herein by reference).

PE nucleic acids and proteins are included. PE sequences are publicly available. For example, GENBANK® Accession Nos. NP_249839.1 and JX026663.1 disclose PE protein and nucleotide sequences, respectively. Truncated PE variants, such as PE38 and PE40, are also included (e.g., PE38KDEL; see U.S. Pat. No. 6,011,002, Kreitman et al. Cancer Res. 55:3357, 1995; Chaudhary et al. PNAS 87: 308, 1990; and Seetharam et al. J Biol Chem. 266: 17376, 1991, which are incorporated herein by reference). One of ordinary skill in the art can identify additional PE nucleic acid and protein sequences, including PE variants that retain PE biological activity (such as inhibiting EF2).

Polynucleotide: A single- or double-strand ("ss" or "ds," respectively) polymer of deoxyribonucleotide or ribonucleotide bases read from the 5' to the 3' end. Polynucleotides include RNA and DNA and may be isolated from natural sources, synthesized in vitro, or prepared from a combination of natural and synthetic molecules. In some examples, two strands of a double-stranded polynucleotide may differ in length and the ends thereof may be staggered as a result of hybridization or enzymatic cleavage; thus, all nucleotides within a double-stranded polynucleotide molecule may not be paired.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences, such as glycoproteins. The term "polypeptide" is specifically intended to cover naturally occurring proteins, as well as those that are recombinantly or synthetically produced.

The term "effective fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

The term "substantially purified polypeptide" as used herein refers to a polypeptide which is substantially free of other proteins, lipids, carbohydrates, or other materials with which it is naturally associated. In one embodiment, the polypeptide is at least 50%, for example at least 80% free of other proteins, lipids, carbohydrates, or other materials with which it is naturally associated. In another embodiment, the polypeptide is at least 90% free of other proteins, lipids, carbohydrates, or other materials with which it is naturally associated. In yet another embodiment, the polypeptide is at least 95% free of other proteins, lipids, carbohydrates, or other materials with which it is naturally associated.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements that can be located as much as several thousand base pairs from the start site of transcription. Both constitutive and inducible promoters are included (see, e.g., Bitter et al., *Methods in Enzymology*, 153:516-544, 1987).

Sequence identity: The similarity between amino acid sequences is expressed in terms of the similarity between the sequences and is otherwise referred to as sequence identity. Sequence identity is frequently measured as percentage identity (or similarity or homology); the higher the percentage, the more similar the two sequences are. Homologs or variants of a polypeptide will possess a relatively high degree of sequence identity when aligned using standard methods.

Methods of aligning sequences for comparison are well-known in the art. Various programs and alignment algorithms are described in: Smith and Waterman, *Adv. Appl. Math*, 2:482, 1981; Needleman and Wunsch, *J. Mol. Biol.*, 48:443, 1970; Pearson and Lipman, *Proc. Natl. Acad. Sci. U.S.A.* 85:2444, 1988; Higgins and Sharp, *Gene*, 73:237, 1988; Higgins and Sharp, *CABIOS*, 5:151, 1989; Corpet et al., *Nucleic Acids Research*, 16:10881, 1988; and Pearson and Lipman, *Proc. Natl. Acad. Sci. U.S.A.*, 85:2444, 1988, and Altschul et al., *Nature Genet*, 6:119, 1994, presents a detailed consideration of sequence alignment methods and homology calculations.

The NCBI Basic Local Alignment Search Tool (BLAST) (Altschul et al., *J. Mol. Biol.*, 215:403, 1990) is available from several sources, including the National Center for Biotechnology Information (NCBI, Bethesda, Md.) and on the internet, for use in connection with the sequence analysis programs blastp, blastn, blastx, tblastn, and tblastx. A description of how to determine sequence identity using this program is available on the NCBI website on the internet.

Homologs and variants are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids and may possess sequence identities of at least 85% or at least 90% or 95%, depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters are used. Methods of aligning sequences for comparison are well-known in the art. Optimal alignment of sequences for comparison can be conducted, e.g., by the local homology algorithm of Smith & Waterman, *Adv. Appl. Math*, 2:482, 1981, by the homology alignment algorithm of Needleman & Wunsch, *J. Mol. Biol*, 48:443, 1970, by the search for similarity method of Pearson & Lipman, *Proc. Nat'l. Acad. Sci. USA*, 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds, *Current Protocols in Molecular Biology*, 1995 supplement).

One example of a useful algorithm is PILEUP. PILEUP uses a simplification of the progressive alignment method of Feng & Doolittle, *J. Mol. Evol.*, 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nucleic Acids Res.*, 12:387-395, 1984).

Another example of algorithms that are suitable for determining percent sequence identity and sequence similarity are the BLAST and the BLAST 2.0 algorithms, which are described in Altschul et al., *J. Mol. Biol*, 215:403-410, 1990 and Altschul et al., *Nucleic Acids Res*, 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA*, 89:10915, 1989). An oligonucleotide is a linear polynucleotide sequence of up to about 100 nucleotide bases in length.

Specifically binding agent: An agent that binds substantially or preferentially only to a defined target (for example to IL-4R), such as a protein, enzyme, polysaccharide, nucleic acid, or a small molecule. For example, an agent that specifically binds a protein binds substantially only the defined protein or to a specific region within the protein. For example, a, "agent that specifically binds IL-4R" includes antibodies and other agents that bind substantially to IL-4R. Such antibodies can be monoclonal or polyclonal antibodies that are specific for the polypeptide (e.g., IL-4R) as well as immunologically effective portions ("fragments") thereof. Other agents include ligands that are specific for the polypeptide; for example, IL-4 specifically binds IL-4R. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Surgery: A physical intervention on tissues, such as a procedure that involves cutting a patient's tissues or closure of a previously sustained wound. Other procedures, such as endoscopy, are considered surgery where common surgical procedure or settings are involved, such as a sterile environment, anesthesia, antiseptic conditions, typical surgical instruments, and suturing or stapling. Surgery is generally an invasive procedure, but excisions that do not penetrate the structure (e.g., laser ablation) or radiosurgical procedures (e.g., irradiation of a tumor) are considered non-invasive surgical procedures.

Subject: As used herein, the term "subject" refers to a mammal and includes, without limitation, humans, domestic animals (e.g., dogs or cats), farm animals (e.g., cows, horses, or pigs), non-human primates, and laboratory animals (mice, rats, hamsters, guinea pigs, pigs, rabbits, dogs, or monkeys). In a particular example, a subject is one who has cancer, such as ovarian cancer, a lung cancer, a liver cancer, a melanoma, an osteosarcoma, or a brain cancer.

Therapeutic agent: Used in a generic sense, it includes treating agents, prophylactic agents, and replacement agents. The agents can be chemotherapeutics (e.g., chemical or biological agents) and physical agents.

Therapeutically effective amount: A quantity of an agent sufficient to achieve a desired effect in a subject being treated. For instance, this can be the amount of IFNα, IFNγ, and IL4-PE polypeptides or polynucleotides encoding such polypeptides necessary to treat cancer (such as ovarian cancer) in a subject, or a dose sufficient to prevent advancement, or to cause regression of a disease, such as cancer, or which is capable of relieving symptoms caused by a disease, such as cancer. In one example, the amount is sufficient to prevent advancement or to cause regression of the disease. In another example, the amount is sufficient to inhibit a sign or symptom of cancer.

An effective amount of IFNα, IFNγ, and IL4-PE polypeptides or polynucleotides encoding such polypeptides can be administered systemically or locally (see below). In addition, an effective amount can be administered in a single dose or in several doses, for example daily, during a course of treatment. However, the effective amount will depend on the preparation applied, the subject being treated, the severity and type of the affliction, and the manner of administration of the compound.

Toxic moiety: The portion of an immunotoxin that renders the immunotoxin cytotoxic to cells of interest. Most commonly, the toxic moiety is a protein cytotoxin, such as PE; however, other toxins, such as radioisotopes, can also be conjugated to the targeting moiety if desired. Persons of skill will recognize that a molecule, such as an antibody, is considered a "moiety" once it is incorporated into a chimeric molecule such as an immunoconjugate (see PCT Pub. No. WO 2003047632, incorporated by reference herein).

The term "toxin" includes any molecule that is cytotoxic, such as *Pseudomonas* exotoxin (PE), ricin A, abrin, ribotoxin, ribonuclease, saporin, calicheamycin, Diphtheria toxin (DT), botulinum toxin, pokeweed antiviral toxin, bryodin 1, *Clostridium perfringens* enterotoxin (CPE), Cholera toxin, BAD (BCL-2 associated death prompter protein), ribosome-inactivating toxins, other bacterial toxins, and derivatives of plant or animal toxins or a cytotoxic fragment thereof. For example, PE and DT are highly toxic compounds that typically bring about death through liver toxicity, and receptors for these compounds are ubiquitous on eukaryotic cells. In some embodiments, PE and DT can be modified into a form for use as an immunotoxin by removing the native targeting component of the toxin (e.g., domain 1a of PE or the B chain of DT) and replacing it with a different targeting moiety, such as an IL-4 or an IL-4R-binding antibody (see id.; U.S. Pat. Nos. 6,011,002; 5,458,878, which are incorporated by reference herein).

Treating a disease: "Treatment" refers to a therapeutic intervention that ameliorates a sign or symptom of a disease or pathological condition, such as a sign or symptom of cancer (e.g., ovarian cancer). Treatment can also induce remission or cure of a condition or can reduce the pathological condition, such as a reduction in tumor size, a reduction in tumor burden, a reduction in a sign or a symptom of a tumor (such as cachexia), a reduction in metastasis, or combinations thereof. In particular examples, treatment includes preventing a disease, for example by inhibiting the full development of a disease, such as decreasing the ability of a tumor to metastasize. Prevention of a disease does not require a total absence of disease.

Tumor: All neoplastic cell growth and proliferation, whether malignant or benign, and all pre-cancerous and cancerous cells and tissues. In one example, a tumor is an ovarian tumor.

Cancer is a malignant tumor (a malignancy), characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of cancer in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid or malignant tumors, such as sarcomas, carcinomas, germ cell tumors, blastomas, and lymphomas, include fibrosarcoma, myxosarcoma, liposarcoma, chondrosarcoma, osteogenic sarcoma, other sarcomas, synovioma, mesothelioma, Ewing's sarcoma (tumor), leiomyosarcoma, rhabdomyosarcoma, colon carcinoma, lymphoid malignancy, pancreatic cancer, breast cancer (including basal breast carcinoma, ductal carcinoma, and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, head cancer, neck cancer, CNS tumors (such as a glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), yolk sac tumors, germinomas, choriocarcinomas, hepatoblastoma, medulloblastoma, nephroblastoma (e.g., Wilms' tumor), neuroblastoma, retinoblastoma, pancreatoblastoma, and pleuropulmonary blastoma.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform, or infect a cell, thereby causing the cell to express nucleic acids and/or proteins other than those native to the cell. A vector optionally includes materials to aid in achieving entry of the nucleic acid into the cell, such as a viral particle, liposome, protein coating, or the like. A vector can be a viral vector.

Overview

The ability to target multiple pathways at the same time is aids in the treatment of human cancer. Disclosed herein is that the combination of IFNα, IFNγ, and IL4-PE that targets multiple receptors and pathways is a therapeutic modality for solid tumors, such as ovarian cancer, and for malignant cancer. It is disclosed herein that IFNs and IL-4PE when used in combination. For example, ovarian cancer epithelial cells are more sensitive to IFNs and IL4-PE than the individual agents alone. When treated with IFNs and IL-4-PE either alone or in combination, the combination approach mediated synergistic antitumor effects.

Interferon Polypeptides and Polynucleotides Encoding Interferons

These methods and compositions disclosed herein utilize IFNα and IFNγ polypeptides and/or nucleic acid molecules that encode IFNα and IFNγ polypeptides. Human and mouse IFNα and IFNγ polypeptides and polynucleotides are disclosed in GENBANK® Accession Nos. AAA52724.1, AAA37886.1, NM_024013.2, and NM_010502.2, incorporated herein by reference, as well as AAB59534.1, ACR22511.1, NM_000619.2, and NM_008337.4, respectively, incorporated herein by reference. IFNα and IFNγ polypeptides and polynucleotides encoding an IFNα and IFNγ polypeptides are of use in the disclosed methods, wherein the IFNα and IFNγ polypeptides increase cancer cell death, such as ovarian cancer cell death.

An exemplary human IFNα is:

MALLFPLLAALVMTSYSPVGSLGCDLPQNHGLLSRNTLVLLHQMRRIS

PFLCLKDRRDFRFPQEMVKGSQLQKAHVMSVLHEMLQQIFSLFHTERS

SAAWNMTLLDQLHTELHQQLQHLETCLLQVVGEGESAGAISSPALTLR

RYFQGIRVYLKEKKYSDCAWEVVRMEIMKSLFLSTNMQERLRSKDRDL

GSS (SEQ ID NO: 1, see GENBANK ®Accession No.
AAA52724.1, incorporated herein by reference).

An exemplary murine IFNα is:

MARPFAFLMVLVVISYWSTCSLGCDLPQTHNLRNKKILTLLAQMRRLS

PLSCLKDRKDFGFPQEKVDAQQIQEAQAIPVLSELTQQILTLFTSKDS

-continued
SAAWNATLLDSFCTGLHQLLNDLQGCLMQLVGMKELPLTQEDSQLAMK

KYFHRITVYLREKKHSPCAWEVVRAEVWRALSSSVNLLARLSEEKE.
(SEQ ID NO: 2, see GENBANK ® Accession No.
AAA37886.1, incorporated herein by reference)

An exemplary human IFNγ is:

MKYTSYILAFQLCIVLGSLGCYCQDPYVKEAENLKKYFNAGHSDVADN

GTLFLGILKNWKEESDRKIMQSQIVSFYFKLFKNFKDDQSIQKSVETI

KEDMNVKFFNSNKKKRDDFEKLTNYSVTDLNVQRKAIHELIQVMAELS

PAAKTGKRKRSQMLFRGRRASQ.
(SEQ ID NO: 3, see GENBANK ® Accession No.
AAB59534.1, incorporated herein by reference)

An exemplary murine IFNγ is:

MNATHCILALQLFLMAVSGCYCHGTVIESLESLNNYFNSSGIDVEEKS

LFLDIWRNWQKDGDMKILQSQIISFYLRLFEVLKDNQAISNNISVIES

HLITNFFSNSKAKKDAFMSIAKFEVNNPQVQRQAFNELIRVVHQLSPE

SSLRKRKRSRC.
(SEQ ID NO: 4, see GENBANK ® Accession No.
ACR22511.1, incorporated herein by reference)

In some embodiments, the methods include administering variants of IFNα (including IFNα subtypes, such as IFNα1, IFNα2a, IFNα4a, IFNα5, IFNα6, IFNα7, IFNα8, IFNα10, IFNα14, IFNα16, IFNα17, and IFNα21) and IFNγ, such as polypeptides about 95%, 96%, 97%, 98%, or 99% identical to human or mouse IFNα and IFNγ. In some embodiments, IFNα polypeptide at least 95% identical to the amino acids set forth in SEQ ID NO: 1 or SEQ ID NO: 2 is administered, such as at least 95%, at least 96%, at least 97%, at least 98%, at least 99%, or 100% identical to the amino acid sequence of SEQ ID NO: 1 or SEQ ID NO: 2, wherein the polypeptide retains interferon activity, such as increasing cancer cell death. In some other embodiments, IFNγ polypeptide at least 95% identical to the amino acids set forth in SEQ ID NO: 3 or SEQ ID NO: 4 is administered, such as at least 95%, at least 96%, at least 97%, at least 98%, at least 99%, or 100% identical to the amino acid sequence of SEQ ID NO: 3 or SEQ ID NO: 4, wherein the polypeptide retains interferon activity, such as increasing cancer cell death. In further embodiments, the IFNα polypeptide administered includes at most 1, 2, 3, 4, 5, 6, 7, 8, 9, or 10 conservative substitutions in SEQ ID NO: 1 or at most 1, 2, 3, 4, 5, 6, 7, 8, 9, 10, or 11 conservative substitutions in SEQ ID NO: 2, wherein the polypeptide retains interferon activity, such as increasing cancer cell death. In additional embodiments, the IFNγ polypeptide administered includes at most 1, 2, 3, 4, 5, 6, 7, 8, 9, or 10 conservative substitutions in SEQ ID NO: 3 or at most 1, 2, 3, 4, 5, 6, 7, 8, 9, 10, or 11 conservative substitutions in SEQ ID NO: 4, wherein the polypeptide retains interferon activity, such as increasing cancer cell death.

In some examples, the method includes administering a nucleic acid molecule encoding the IFNα polypeptide.

An exemplary nucleic acid encoding human IFNα is:

CAAGGTTCAGAGTCACCCATCTCAGCAAGCCCAGAAGTATCTGCAATA

TCTACGATGGCCTCGCCCTTTGCTTTACTGATGGTCCTGGTGGTGCTC

-continued
```
AGCTGCAAGTCAAGCTGCTCTCTGGGCTGTGATCTCCCTGAGACCCAC
AGCCTGGATAACAGGAGGACCTTGATGCTCCTGGCACAAATGAGCAGA
ATCTCTCCTTCCTCCTGTCTGATGGACAGACATGACTTTGGATTTCCC
CAGGAGGAGTTTGATGGCAACCAGTTCCAGAAGGCTCCAGCCATCTCT
GTCCTCCATGAGCTGATCCAGCAGATCTTCAACCTCTTTACCACAAAA
GATTCATCTGCTGCTTGGGATGAGGACCTCCTAGACAAATTCTGCACC
GAACTCTACCAGCAGCTGAATGACTTGGAAGCCTGTGTGATGCAGGAG
GAGAGGGTGGGAGAAACTCCCCTGATGAATGCGGACTCCATCTTGGCT
GTGAAGAAATACTTCCGAAGAATCACTCTCTATCTGACAGAGAAGAAA
TACAGCCCTTGTGCCTGGGAGGTTGTCAGAGCAGAAATCATGAGATCC
CTCTCTTTATCAACAAACTTGCAAGAAAGATTAAGGAGGAAGGAATAA
CATCTGGTCCAACATGAAAACAATTCTTATTGACTCATACACCAGGTC
ACGCTTTCATGAATTCTGTCATTTCAAAGACTCTCACCCCTGCTATAA
CTATGACCATGCTGATAAACTGATTTATCTATTTAAATATTTATTTAA
CTATTCATAAGATTTAAATTATTTTGTTCATATAACGTCATGTGCAC
CTTTACACTGTGGTTAGTGTAATAAAACATGTTCCTTATATTTACTC.
```
(SEQ ID NO: 5, see GENBANK ® Accession No. NM_024013.2, incorporated herein by reference)

An exemplary nucleic acid encoding mouse IFNα is:

```
ATGGCTAGGCTCTGTGCTTTCCTGATGGTCCTGGCGGTGCTGAGCTAC
TGGCCAACCTGCTCTCTAGGATGTGACCTTCCTCAGACTCATAACCTC
AGGAACAAGAGAGCCTTGACACTCCTGGTACAAATGAGGAGACTCTCC
CCTCTCTCCTGCCTGAAGGACAGGAAGGACTTTGGATTCCCGCAGGAG
AAGGTGGATGCCCAGCAGATCAAGAAGGCTCAAGCCATCCCTGTCCTG
AGTGAGCTGACCCAGCAGATCCTGAACATCTTCACATCAAAGGACTCA
TCTGCTGCATGGAATACAACCCTCCTAGACTCATTCTGCAATGACCTC
CACCAGCAGCTCAATGACCTGCAAGGCTGTCTGATGCAGCAGGTGGGG
GTGCAGGAATTTCCCCTGACCCAGGAAGATGCCCTGCTGGCTGTGAGG
AAATACTTCCACAGGATCACTGTGTACCTGAGAGAGAAGAAACACAGC
CCCTGTGCCTGGGAGGTGGTCAGAGCAGAAGTCTGGAGAGCCCTGTCT
TCCTCTGCCAATGTGCTGGGAAGACTGAGAGAAGAGAAATGA.
```
(SEQ ID NO: 6, see GENBANK ® Accession No. NM_010502.2, incorporated herein by reference)

In some examples, the method includes administering a nucleic acid molecule encoding the IFNγ polypeptide.

An exemplary nucleic acid encoding human IFNγ is:

```
CACATTGTTCTGATCATCTGAAGATCAGCTATTAGAAGAGAAAGATCA
GTTAAGTCCTTTGGACCTGATCAGCTTGATACAAGAACTACTGATTTC
AACTTCTTTGGCTTAATTCTCTCGGAAACGATGAAATATACAAGTTAT
ATCTTGGCTTTTCAGCTCTGCATCGTTTTGGGTTCTCTTGGCTGTTAC
TGCCAGGACCCATATGTAAAAGAAGCAGAAAACCTTAAGAAAATATTTT
AATGCAGGTCATTCAGATGTAGCGGATAATGGAACTCTTTTCTTAGGC
ATTTTGAAGAATTGGAAAGAGGAGAGTGACAGAAAAATAATGCAGAGC
CAAATTGTCTCCTTTTACTTCAAACTTTTTAAAAACTTTAAAGATGAC
CAGAGCATCCAAAAGAGTGTGGAGACCATCAAGGAAGACATGAATGTC
AAGTTTTTCAATAGCAACAAAAAGAAACGAGATGACTTCGAAAAGCTG
ACTAATTATTCGGTAACTGACTTGAATGTCCAACGCAAAGCAATACAT
GAACTCATCCAAGTGATGGCTGAACTGTCGCCAGCAGCTAAAACAGGG
AAGCGAAAAGGAGTCAGATGCTGTTTCGAGGTCGAAGAGCATCCCAG
TAATGGTTGTCCTGCCTGCAATATTTGAATTTTAAATCTAAATCTATT
TATTAATATTTAACATTATTTATATGGGGAATATATTTTTAGACTCAT
CAATCAAATAAGTATTTATAATAGCAACTTTTGTGTAATGAAAATGAA
TATCTATTAATATATGTATTATTTATAATTCCTATATCCTGTGACTGT
CTCACTTAATCCTTTGTTTTCTGACTAATTAGGCAAGGCTATGTGATT
ACAAGGCTTTATCTCAGGGGCCAACTAGGCAGCCAACCTAAGCAAGAT
CCCATGGGTTGTGTGTTTATTTCACTTGATGATACAATGAACACTTAT
AAGTGAAGTGATACTATCCAGTTACTGCCGGTTTGAAAATATGCCTGC
AATCTGAGCCAGTGCTTTAATGGCATGTCAGACAGAACTTGAATGTGT
CAGGTGACCCTGATGAAAACATAGCATCTCAGGAGATTTCATGCCTGG
TGCTTCCAAATATTGTTGACAACTGTGACTGTACCCAAATGGAAAGTA
ACTCATTTGTTAAAATTATCAATATCTAATATATATGAATAAAGTGTA
AGTTCACAACAAAAAAAAAAAAAAAAAAAAAAAAAAAAAAAA.
```
(SEQ ID NO: 7, see GENBANK ® Accession No. NM_000619.2, incorporated herein by reference)

An exemplary nucleic acid encoding mouse IFNγ is:

```
TATAGCTGCCATCGGCTGACCTAGAGAAGACACATCAGCTGATCCTTT
GGACCCTCTGACTTGAGACAGAAGTTCTGGGCTTCTCCTCCTGCGGCC
TAGCTCTGAGACAATGAACGCTACACACTGCATCTTGGCTTTGCAGCT
CTTCCTCATGGCTGTTTCTGGCTGTTACTGCCACGGCACAGTCATTGA
AAGCCTAGAAAGTCTGAATAACTATTTTAACTCAAGTGGCATAGATGT
GGAAGAAAAGAGTCTCTTCTTGGATATCTGGAGGAACTGGCAAAAGGA
TGGTGACATGAAAATCCTGCAGAGCCAGATTATCTCTTTCTACCTCAG
ACTCTTTGAAGTCTTGAAAGACAATCAGGCCATCAGCAACAACATAAG
CGTCATTGAATCACACCTGATTACTACCTTCTTCAGCAACAGCAAGGC
GAAAAAGGATGCATTCATGAGTATTGCCAAGTTTGAGGTCAACAACCC
ACAGGTCCAGCGCCAAGCATTCAATGAGCTCATCCGAGTGGTCCACCA
GCTGTTGCCGGAATCCAGCCTCAGGAACTCGGAAAAGGAGTCGCTGCT
GATTCGGGGTGGGAAGAGATTGTCCCAATAAGAATAATTCTGCCAGC
ACTATTTGAATTTTAAATCTAAACCTATTTATTAATATTTAAAACTA
TTTATATGGAGAATCTATTTTAGATGCATCAACCAAAGAAGTATTTAT
AGTAACAACTTATATGTGATAAGAGTGAATTCCTATTAATATATGTGT
TATTTATAATTTCTGTCTCCTCAACTATTTCTCTTTGACCAATTAATT
ATTCTTTCTGACTAATTAGCCAAGACTGTGATTGCGGGGTTGTATCTG
```

-continued
```
GGGGTGGGGACAGCCAAGCGGCTGACTGAACTCAGATTGTAGCTTGT

ACCTTTACTTCACTGACCAATAAGAAACATTCAGAGCTGCAGTGACCC

CGGGAGGTGCTGCTGATGGGAGGAGATGTCTACACTCCGGGCCAGCGC

TTTAACAGCAGGCCAGACAGCACTCGAATGTGTCAGGTAGTAACAGGC

TGTCCCTGAAAGAAAGCAGTGTCTCAAGAGACTTGACACCTGGTGCTT

CCCTATACAGCTGAAAACTGTGACTACACCCGAATGACAAATAACTCG

CTCATTTATAGTTTATCACTGTCTAATTGCATATGAATAAAGTATACC

TTTGCAACCAA.
(SEQ ID NO: 8, see GENBANK ® Accession No.
NM_008337.4, incorporated herein by reference)
```

In some embodiments, the nucleic acid molecule includes a nucleic acid sequence encoding an amino acid sequence at least 95% identical to the amino acid sequence of SEQ ID NO: 1 or SEQ ID NO: 2, such as at least 95%, at least 96%, at least 97%, at least 98%, at least 99%, or 100% identical to the amino acid sequence of SEQ ID NO: 1 or SEQ ID NO: 2, wherein the polypeptide retains interferon activity, such as increasing cancer cell death. In further embodiments, the nucleic acid molecule includes a nucleic acid sequence encoding an amino acid sequence at least 95% identical to the amino acid sequence of SEQ ID NO: 3 or SEQ ID NO: 4, wherein the amino acid sequence retains interferon activity, such as increasing cancer cell death, such as at least 95%, at least 96%, at least 97%, at least 98%, at least 99%, or 100% identical to the amino acid sequence of SEQ ID NO: 3 or SEQ ID NO: 4, wherein the amino acid sequence retains interferon activity, such as increasing cancer cell death. In some embodiments, the nucleic acid molecule encodes a polypeptide that includes at most 1, 2, 3, 4, 5, 6, 7, 8, 9, or 10 conservative substitutions in SEQ ID NO: 1 or SEQ ID NO: 2, wherein the polypeptide retains interferon activity, such as increasing cancer cell death. In further embodiments, the nucleic acid molecule encodes a polypeptide that includes at most 1, 2, 3, 4, 5, 6, 7, 8, 9, or 10 conservative substitutions in SEQ ID NO: 3 or SEQ ID NO: 4. In yet other embodiments, the nucleic acid molecule is at least 85% identical to SEQ ID NO: 5, for example a nucleic acid molecule that is 85%, at least 90%, at least 95%, at least 96%, at least 97%, at least 98%, at least 99%, or 100% identical to SEQ ID NO: 5, wherein the nucleic acid encodes a polypeptide that retains interferon activity, such as increasing cancer cell death. In yet other embodiments, the nucleic acid molecule is at least 85% identical to SEQ ID NO: 6, for example a nucleic acid molecule that is 85%, at least 90%, at least 95%, at least 96%, at least 97%, at least 98%, at least 99%, or 100% identical to SEQ ID NO: 6, wherein the nucleic acid encodes a polypeptide that retains interferon activity, such as increasing cancer cell death. In yet other embodiments, the nucleic acid molecule is at least 85% identical to SEQ ID NO: 7, for example a nucleic acid molecule that is 85%, at least 90%, at least 95%, at least 96%, at least 97%, at least 98%, at least 99%, or 100% identical to SEQ ID NO: 7, wherein the nucleic acid encodes a polypeptide that retains interferon activity, such as increasing cancer cell death. In yet other embodiments, the nucleic acid molecule is at least 85% identical to SEQ ID NO: 8, for example a nucleic acid molecule that is 85%, at least 90%, at least 95%, at least 96%, at least 97%, at least 98%, at least 99%, or 100% identical to SEQ ID NO: 8, wherein the nucleic acid encodes a polypeptide that retains interferon activity, such as increasing cancer cell death.

Polypeptides and Polynucleotides Encoding Chimeric Molecules

The methods disclosed herein use chimeric molecules, which include agents that bind IL-4R and toxic moieties (e.g., U.S. Pat. No. 6,011,002, incorporated by reference herein). In some examples, the agents that bind IL-4R can be IL-4 (e.g., U.S. Pat. No. 6,011,002, incorporated by reference herein). In further examples, the toxic moiety can be PE, such as wild type PE, PE3, or PE40 and any variations thereof (e.g., U.S. Pat. Nos. 6,011,002; 5,458,878, incorporated by reference herein). Nucleic acids encoding these molecules can also be used in the disclosed methods.

Polypeptides and Polynucleotides Encoding Agents that Bind IL-4R

The methods disclosed herein use agents that bind IL-4R (e.g., U.S. Pat. Nos. 6,011,002; 8,388,965, incorporated by reference herein). In some embodiments, the agent that binds IL-4R is IL-4 polypeptide (e.g., U.S. Pat. No. 6,011,002, incorporated by reference herein). In some other examples, the agent that binds IL-4R is an antibody specific for IL-4R (e.g., U.S. Pat. No. 8,388,965, incorporated by reference herein). The disclosed methods can include administering chimeric molecules, which include an agent that binds IL-4R, such as IL-4, or nucleic acids that encode these chimeric molecules.

Human and mouse IL-4 polypeptides and polynucleotides are disclosed in GENBANK® Accession Nos. CAP72493.1, AAH27514.1, M13982.1, NM_201270.1, and M25892.1, incorporated herein by reference. IL-4 polypeptides and polynucleotides encoding an IL-4 polypeptide are of use in the disclosed compositions and methods, wherein the IL-4 polypeptide binds IL-4R.

An exemplary human IL-4 is:

```
MGLTSQLLPPLFFLLACAGNFVHGHKCDITLQEIIKTLNSLTEQKTLC

TELTVTDIFAASKNTTEKETFCRAATVLRQFYSHHEKDTRCLGATAQQ

FHRHKQLIRLLKRLDRNLWGLAGLNSCPVKEANQSTLENFLERLKTIM

REKYSKCSS.
(SEQ ID NO: 9, see GENBANK ® Accession No.
CAP72493.1, incorporated herein by reference)
```

An exemplary murine IL-4 is:

```
MGLNPQLVVILLFFLECTRSHIHGCDKNHLREIIGILNEVTGEGTPCT

EMDVPNVLTATKNTTESELVCRASKVLRIFYLKHGKTPCLKKNSSVLM

ELQRLFRAFRCLDSSISCTMNESKSTSLKDFLESLKSIMQMDYS.
(SEQ ID NO: 10, see GENBANK ® Accession No.
AAH27514.1, incorporated herein by reference)
```

In some embodiments, the methods include administering chimeric molecules, which include an agent that binds IL-4R, such as IL-4 or variants of IL-4, such as polypeptides about 95%, 96%, 97%, 98%, or 99% identical to human or mouse of IL-4. In some embodiments, an IL-4 polypeptide at least 95% identical to the amino acids set forth in SEQ ID NO: 9 or SEQ ID NO: 10, wherein the IL-4 polypeptide retains IL-4 activity, such as binding IL-4R, is included in the chimeric molecules administered, such as at least 95%, at least 96%, at least 97%, at least 98%, at least 99%, or 100% identical to the amino acid sequence of SEQ ID NO: 9 or SEQ ID NO: 10, wherein the IL-4 polypeptide retains IL-4 activity, such as binding IL-4R. In further embodiments, the IL-4 polypeptide administered includes at most 1, 2, 3, 4, 5, 6, 7, 8, 9, or 10 conservative substitutions in SEQ ID NO: 9 or at most 1, 2, 3, 4, 5, 6, 7, 8, 9, 10, or 11 conservative substitutions in SEQ ID NO: 10, wherein the polypeptide retains activity, such as binding to IL-4R.

In some other examples, the method includes administering a nucleic acid molecule encoding the chimeric molecules, which include an agent that binds IL-4R, such as IL-4 polypeptide.

An exemplary nucleic acid encoding human IL-4 is:

```
GATCGTTAGCTTCTCCTGATAAACTAATTGCCTCACATTGTCACTGCA

AATCGACACCTATTAATGGGTCTCACCTCCCAACTGCTTCCCCCTCTG

TTCTTCCTGCTAGCATGTGCCGGCAACTTTGTCCACGGACACAAGTGC

GATATCACCTTACAGGAGATCATCAAAACTTTGAACAGCCTCACAGAG

CAGAAGACTCTGTGCACCGAGTTGACCGTAACAGACATCTTTGCTGCC

TCCAAGAACACAACTGAGAAGGAAACCTTCTGCAGGGCTGCGACTGTG

CTCCGGCAGTTCTACAGCCACCATGAGAAGGACACTCGCTGCCTGGGT

GCGACTGCACAGCAGTTCCACAGGCACAAGCAGCTGATCCGATTCCTG

AAACGGCTCGACAGGAACCTCTGGGGCCTGGCGGGCTTGAATTCCTGT

CCTGTGAAGGAAGCCAACCAGAGTACGTTGGAAAACTTCTTGGAAAGG

CTAAAGACGATCATGAGAGAGAAATATTCAAAGTGTTCGAGCTGAATA

TTTTAATTTATGAGTTTTTCTATAGCTTTATTTTTTAAGTATTTATAT

ATTTATAACTCATCATAAAATAAAGTATATATAGAATCT.
(SEQ ID NO: 11, see GENBANK ® Accession No.
M13982.1, incorporated herein by reference)
```

An exemplary nucleic acid encoding mouse IL-4 is:

```
GGATCCCCGGGCAGAGCTGGGGGGGATTTGTTAGCATCTCTTGATAA

ACTTAATTGTCTCTCGTCACTGACGGCACAGAGCTATTGATGGGTCTC

AACCCCCAGCTAGTTGTCATCCTGCTCTTCTTTCTCGAATGTACCAGG

AGCCATATCCACGGATGCGACAAAAATCACTTGAGAGAGATCATCGGC

ATTTTGAACGAGGTCACAGGAGAAGGGACGCCATGCACGGAGATGGAT

GTGCCAAACGTCCTCACAGCAACGAAGAACACCACAGAGAGTGAGCTC

GTCTGTAGGGCTTCCAAGGTGCTTCGCATATTTTATTTAAAACATGGG

AAAACTCCATGCTTGAAGAAGAACTCTAGTGTTCTCATGGAGCTGCAG

AGACTCTTTCGGGCTTTTCGATGCCTGGATTCATCGATAAGCTGCACC

ATGAATGAGTCCAAGTCCACATCACTGAAAGACTTCCTGGAAAGCCTA

AAGAGCATCATGCAAATGGATTACTCGTAGTACTGAGCCACCATGCTT

TAACTTATGAATTTTTAATGGTTTTATTTTAATATTTATATATTTATA

ATTCATAAAATAAAATATTTGTATAATGT.
(SEQ ID NO: 12, see GENBANK ® Accession No.
M25892.1, incorporated herein by reference)
```

Polypeptides and Polynucleotides Encoding a Toxic Moiety

These chimeric molecules further include toxic moieties. The disclosed methods can include administering chimeric molecules, which include a toxic moiety, such as PE or variants thereof, or nucleic acids that encode these chimeric molecules.

PE polypeptides and polynucleotides are disclosed in GENBANK® Accession No. NP_249839.1 and JX026663.1, incorporated herein by reference. PE polypeptides and polynucleotides encoding a PE polypeptide are of use in the disclosed methods, such as a PE that is cytotoxic to cancer cells (e.g., ovarian cancer cells). PE variants are also of use, such as the PE38 and PE40 variants (e.g., PE38KDEL) described in U.S. Pat. Nos. 6,011,002; 5,458,878; Kreitman et al., *Cancer Res,* 55:3357, 1995; Chaudhary et al., *PNAS,* 87: 308, 1990; and Seetharam et al., *J Biol Chem,* 266: 17376, 1991, all of which are incorporated herein by reference.

The methods disclosed herein utilize PE polypeptides and/or nucleic acids that encode PE polypeptides.

An exemplary PE is:

```
MHLTPHWIPLVASLGLLAGGSFASAAEEAFDLWNECAKACVLDLKDGV

RSSRMSVDPAIADTNGQGVLHYSMVLEGGNDALKLAIDNALSITSDGL

TIRLEGGVEPNKPVRYSYTRQARGSWSLNWLVPIGHEKPSNIKVFIHE

LNAGNQLSHMSPIYTIEMGDELLAKLARDATFFVRAHESNEMQPTLAI

SHAGVSVVMAQAQPRREKRWSEWASGKVLCLLDPLDGVYNYLAQQRCN

LDDTWEGKIYRVLAGNPAKHDLDIKPTVISHRLHFPEGGSLAALTAHQ

ACHLPLETFTRHRQPRGWEQLEQCGYPVQRLVALYLAARLSWNQVDQV

IRNALASPGSGGDLGEAIREQPEQARLALTLAAAESERFVRQGTGNDE

AGAASADVVSLTCPVAAGECAGPADSGDALLERNYPTGAEFLGDGGDI

SFSTRGTQNWTVERLLQAHRQLEERGYVFVGYHGTFLEAAQSIVFGGV

RARSQDLDAIWRGFYIAGDPALAYGYAQDQEPDARGRIRNGALLRVYV

PRSSLPGFYRTGLTLAAPEAAGEVERLIGHPLPLRLDAITGPEEEGGR

LETILGWPLAERTVVIPSAIPTDPRNVGGDLDPSSIPDKEQAISALPD

YASQPGKPPREDLK.
(SEQ ID NO: 13, see GENBANK ® Accession No.
NP_249839.1, incorporated herein by reference)
```

In some other examples, the method includes administering a nucleic acid molecule encoding the PE polypeptide.

An exemplary nucleic acid encoding PE is:

```
ATGCACCTGATACCCCATTGGATCCCCCTGGTCGCCAGCCTCGGCCTG

CTCGCCGGCGGCTCGTTCGCGTCCGCCGCCGAGGAAGCCTTCGACCTC

TGGAACGAATGCGCCAAGGCCTGCGTGCTCGACCTCAAGGACGGCGTG

CGTTCCAGCCGCATGAGCGTCGACCCGGCCATCGCCGACACCAACGGC

CAGGGCGTGCTGCACTACTCCATGGTCCTGGAGGGCGGCAACGACGCG

CTCAAGCTGGCCATCGACAACGCCCTCAGCATCACCAGCGACGGCCTG

ACCATCCGCCTCGAAGGCGGCGTCGAGCCGAACAAGCCGGTGCGCTAC

AGCTACACGCGCCAGGCGCGCGGCAGTTGGTCGCTGAACTGGCTGGTG

CCGATCGGCCACGAGAAGCCTTCGAACATCAAGGTGTTCATCCACGAA

CTGAACGCCGGTAACCAGCTCAGCCACATGTCGCCGATCTACACCATC

GAGATGGGCGACGAGTTGCTGGCGAAGCTGGCGCGCGATGCCACCTTC

TTCGTCAGGGCGCACGAGAGCAACGAGATGCAGCCGACGCTCGCCATC

AGCCATGCCGGGGTCAGCGTGGTCATGGCCCAGGCCCAGCCGCGCCGG

GAAAAGCGCTGGAGCGAATGGGCCAGCGGCAAGGTGTTGTGCCTGCTC
```

```
GACCCGCTGGACGGGGTCTACAACTACCTCGCCCAGCAGCGCTGCAAC

CTCGACGATACCTGGGAAGGCAAGATCTACCGGGTGCTCGCCGGCAAC

CCGGCGAAGCATGACCTGGACATCAAGCCCACGGTCATCAGTCATCGC

CTGCACTTCCCCGAGGGCGGCAGCCTGGCCGCGCTGACCGCGCACCAG

GCTTGCCACCTGCCGCTGGAGACCTTCACCCGTCATCGCCAGCCGCGC

GGCTGGGAACAACTGGAGCAGTGCGGCTATCCGGTGCAGCGGCTGGTC

GCCCTCTACCTGGCGGCGCGACTGTCGTGGAACCAGGTCGACCAGGTG

ATCCGCAACGCCCTGGCCAGCCCCGGCAGCGGCGGCGACCTGGGCGAA

GCGATCCGCGAGCAGCCGGAGCAGGCCCGTCTGGCCCTGACCCTGGCC

GCCGCCGAGAGCGAGCGCTTCGTCCGGCAGGGCACCGGCAACGACGAG

GCCGGCGCGGCCAGCGCCGACGTGGTGAGCCTGACCTGCCCGGTCGCC

GCCGGTGAATGCGCGGGCCCGGCGGACAGCGGCGACGCCCTGCTGGAG

CGCAACTATCCCACTGGCGCGGAGTTCCTCGGCGACGGCGGCGACGTC

AGCTTCAGCACCCGCGGCACGCAGAACTGGACGGTGGAGCGGCTGCTC

CAGGCGCACCGCCAACTGGAGGAGCGCGGCTATGTATTCGTCGGCTAC

CACGGCACCTTCCTCGAAGCGGCGCAAAGCATCGTCTTCGGCGGGGTG

CGCGCGCGCAGCCAGGACCTCGACGCGATCTGGCGCGGTTTCTATATC

GCCGGCGATCCGGCGCTGGCCTACGGCTACGCCCAGGACCAGGAACCC

GACGCGCGCGGCCGGATCCGCAACGGTGCCCTGCTGCGGGTCTATGTG

CCGCGCTCGAGCCTGCCGGGCTTCTACCGCACCGGCCTGACCCTGGCC

GCGCCGGAGGCGGCGGGCGAGGTCGAACGGCTGATCGGCCATCCGCTG

CCGCTGCGCCTGGACGCCATCACCGGCCCCGAGGAGGAAGGCGGGCGC

CTGGAGACCATTCTCGGCTGGCCGCTGGCCGAGCGCACCGTGGTGATT

CCCTCGGCGATCCCCACCGACCCGCGCAACGTCGGCGGCGACCTCGAC

CCGTCCAGCATCCCCGACAAGGAACAGGCGATCAGCGCCCTGCCGGAC

TACGCCAGCCAGCCCGGCAAACCGCCGCGCGAGGACCTGAAGTAA.
(SEQ ID NO: 14, see GENBANK ® Accession No.
JX026663.1, incorporated herein by reference)
```

In some embodiments, the nucleic acid molecule includes a nucleic acid sequence encoding an amino acid sequence at least 95% identical to the amino acid sequence of SEQ ID NO: 13, wherein the amino acid sequence retains cytotoxic activity, such as killing tumor cells, such as at least 95%, at least 96%, at least 97%, at least 98%, at least 99%, or 100% identical to the amino acid sequence of SEQ ID NO: 13, wherein the amino acid sequence retains cytotoxic activity, such as killing tumor cells. In further embodiments, the nucleic acid molecule encodes a polypeptide that includes at most 1, 2, 3, 4, 5, 6, 7, 8, 9, or 10 conservative substitutions in SEQ ID NO: 14, wherein the polypeptide retains cytotoxic activity, such as killing tumor cells. In yet other embodiments, the nucleic acid molecule is at least 85% identical to SEQ ID NO: 14, wherein the amino acid sequence encoded thereby retains cytotoxic activity, such as killing tumor cells, for example a nucleic acid molecule that is 85%, at least 90%, at least 95%, at least 96%, at least 97%, at least 98%, at least 99%, or 100% identical to SEQ ID NO: 14, wherein the amino acid sequence encoded thereby retains cytotoxic activity, such as killing tumor cells (e.g., U.S. Pat. Nos. 6,011,002; 5,458,878, incorporated by reference herein).

The methods and compositions herein include agents that specifically bind IL-4R. These agents can be fused to a toxic moiety. For example, the IL-4R-binding agent that is fused to the toxic moiety can be IL-4 or a variant or effective fragment thereof, an antibody that specifically binds IL-4R, or an antigen-binding fragment. In some examples, the IL-4R-binding agent can be fused to a toxin, such as Pseudomonas exotoxin (PE), ricin A, abrin, ribotoxin, ribonuclease, saporin, calicheamycin, Diphtheria toxin, botulinum toxin, pokeweed antiviral toxin, bryodin 1, Clostridium perfringens enterotoxin (CPE), Cholera toxin, BAD (BCL-2 associated death prompter protein), ribosome-inactivating toxins or a cytotoxic fragment thereof. In some other examples, the IL-4R-binding agent can be fused to a chemotherapeutic agent, such as taxane, carboplatin, cyclophosphamide, and/or doxorubicin.

The chimeric molecule can include circularly permuted molecules, which may include DNA, RNA, and protein. In some examples, the chimeric molecule includes a circularly permuted protein that specifically binds IL-4R and a toxic moiety (e.g., circularly permuted IL-4 fused to PE).

The methods disclosed herein utilize circularly permuted polypeptides comprising an IL-4 polypeptide and a PE polypeptide or variant thereof (e.g., PE38KDEL) and/or nucleic acids that encode circularly permuted polypeptides comprising an IL-4 polypeptide and a PE polypeptide or variant thereof.

An exemplary circularly permuted polypeptide comprising an IL-4 polypeptide and a PE variant (PE38KDEL), "IL4-PE38KDEL," is:

```
                                    (SEQ ID NO: 15)
HMDTTEKETFCRAATVLRQFYSHHEKDTRCLGATAQQFHRHKQLIRFLK

RLDRNLWGLAGLNSCPVKEANQSTLENFLERLKTIMREKYSKCSSKCDI

TLQEIIKTLNSLTEQKTLCTELTVTDIFAASKASGGPEGGSLAALTAHQ

ACHLPLETFTRHRQPRGWEQLEQCGYPVQRLVALYLAARLSWNQVDQVI

RNALASPGSGGDLGEAIREQPEQARLALTLAAAESERFVRQGTGNDEAG

AANGPADSGDALLERNYPTGAEFLGDGGDVSFSTRGTQNWTVERLLQAH

RQLEERGYVFVGYHGTFLEAAQSIVFGGVRARSQDLDAIWRGFYIAGDP

ALAYGYAQDQEPDARGRIRNGALLRVYVPRSSLPGFYRTSLTLAAPEAA

GEVERLIGHPLPLRLDAITGPEEEGGRLETILGWPLAERTVVIPSAIPT

DPRNVGGDLDPSSIPDKEQAISALPDYASQPGKPPKDEL.
```

In some other examples, the method includes administering a nucleic acid molecule encoding circularly permuted polypeptides comprising an IL-4 polypeptide and a PE polypeptide or variant thereof.

An exemplary nucleic acid encoding a circularly permuted polypeptide comprising an IL-4 polypeptide and a PE variant (PE38KDEL), "IL4-PE38KDEL," is:

```
                                    (SEQ ID NO: 16)
CATATGGACACAACTGAGAAGGAAACCTTCTGCAGGGCTGCGACTGTG

CTCCGGCAGTTCTACAGCCACCATGAGAAGGACACTCGCTGCCTGGGT

GCGACTGCACAGCAGTTCCACAGGCACAAGCAGCTGATCCGATTCCTG

AAACGGCTCGACAGGAACCTCTGGGGCCTGGCGGGCTTGAATTCCTGT

CCTGTGAAGGAAGCCAACCAGAGTACGTTGGAAAACTTCTTGGAAAGG
```

```
-continued
CTAAAGACGATCATGAGAGAGAAATATTCAAAGTGTTCGTCCAAGTGC

GATATCACCTTACAGGAGATCATCAAAACTTTGAACAGCCTCACAGAG

CAGAAGACTCTGTGCACCGAGTTGACCGTAACAGACATCTTTGCTGCC

TCCAAAGCTTCCGGAGGTCCCGAGGGCGGCAGCCTGGCCGCGCTGACC

GCGCACCAGGCTTGCCACCTGCCGCTGGAGACTTTCACCCGTCATCGC

CAGCCGCGCGGCTGGGAACAACTGGAGCAGTGCGGCTATCCGGTGCAG

CGGCTGGTCGCCCTCTACCTGGCGGCGCGGCTGTCGTGGAACCAGGTC

GACCAGGTGATCCGCAACGCCCTGGCCAGCCCCGGCAGCGGCGGCGAC

CTGGGCGAAGCGATCCGCGAGCAGCCGGAGCAGGCCCGTCTGGCCCTG

ACCCTGGCCGCCGCCGAGAGCGAGCGCTTCGTCCGGCAGGGCACCGGC

AACGACGAGGCCGGCGCGGCCAACGGCCCGGCGGACAGCGGCGACGCC

CTGCTGGAGCGCAACTATCCCACTGGCGCGGAGTTCCTCGGCGACGGC

GGCGACGTCAGCTTCAGCACCCGCGGCACGCAGAACTGGACGGTGGAG

CGGCTGCTCCAGGCGCACCGCCAACTGGAGGAGCGCGGCTATGTGTTC

GTCGGCTACCACGGCACCTTCCTCGAAGCGGCGCAAAGCATCGTCTTC

GGCGGGGTGCGCGCGCGCAGCCAGGACCTCGACGCGATCTGGCGCGGT

TTCTATATCGCCGGCGATCCGGCGCTGGCCTACGGCTACGCCCAGGAC

CAGGAACCCGACGCACGCGGCCGGATCCGCAACGGTGCCCTGCTGCGG

GTCTATGTGCCGCGCTCGAGCCTGCCGGGCTTCTACCGCACCAGCCTG

ACCCTGGCCGCGCCGGAGGCGGCGGGCGAGGTCGAACGGCTGATCGGC

CATCCGCTGCCGCTGCGCCTGGACGCCATCACCGGCCCCGAGGAGGAA

GGCGGGCGCCTGGAGACCATTCTCGGCTGGCCGCTGGCCGAGCGCACC

GTGGTGATTCCCTCGGCGATCCCCACCGACCCGCGCAACGTCGGCGGC

GACCTCGACCCGTCCAGCATCCCCGACAAGGAACAGGCGATCAGCGCC

CTGCCGGACTACGCCAGCCAGCCCGGCAAACCGCCGAAAGACGAGCTC

TAAGAATTCGGCTGCTAACAAAGCCCGAAAGGAAGCTGAGTT.
```

Any of the polypeptides described herein can be included in a fusion protein. Thus, in some embodiments, any of the IFNα and IFNγ polypeptides, effective fragments thereof, or variants thereof and chimeric molecule is administered as a fusion protein, such as an Fc fusion protein (e.g., U.S. Pat. Nos. 8,563,692; 6,011,002, incorporated by reference herein). In some specific, non-liming examples, the Fc domain is an IgG Fc domain, such as an $IgG_1$, $IgG_2$, $IgG_3$, or $IgG_4$ Fc domain. In some embodiments, these forms of the IFNα and IFNγ polypeptide, effective fragments thereof, or variants thereof and chimeric molecule have an increased half-life as compared to the IFNα and IFNγ polypeptide, effective fragments thereof, or variants thereof and chimeric molecule not included in the fusion protein.

Without being bound by theory, the Fc domain increases the half-life of an IgG through its unique pH-dependent association with the neonatal Fc receptor (FcRn). After internalization, the Fc domain of IgG can bind to FcRn in the acidic environment of the endosome such that the IgG is then cycled onto the cell surface and re-released into circulation. This biological system protects IgG from degradation and results in a long serum half-life. Fusions of an Fc domain and a therapeutic molecule have an extended half-life. In addition, because the Fc fragment of IgG consists of a tightly packed homodimer, two therapeutic proteins are present in each molecule. Recently, monomeric Fc fusion proteins were generated in which a single active protein was fused to dimeric wild-type Fc. These smaller molecules have been shown to possess extended half-lives compared with the dimeric version.

Polynucleotides and Vectors

Polynucleotides that encode the IFNα and IFNγ polypeptides, effective fragments thereof, or variants thereof and chimeric polypeptide (e.g., IL4-PE) include DNA, cDNA, and RNA sequences. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, Biochemistry, $3^{rd}$ Edition, W.H. 5 Freeman and Co., NY, 1988).

Nucleic acid molecules encoding an IFNα and IFNγ polypeptides, effective fragments thereof, or variants thereof and a chimeric polypeptide (e.g., IL4-PE) can readily be produced by one of skill in the art using the amino acid sequences provided herein and the genetic code. Nucleic acid sequences encoding the IFNα and IFNγ polypeptides, effective fragments thereof, or variants thereof and chimeric polypeptide (e.g., IL4-PE) can be prepared by any suitable method including, for example, cloning of appropriate sequences or by direct chemical synthesis by methods, such as the phosphotriester method of Narang et al., *Methods Enzymol.*, 68:90-99, 1979; the phosphodiester method of Brown et al., *Methods Enzymol.*, 68:109-151, 1979; the diethylphosphoramidite method of Beaucage et al., *Tetra. Lett,* 22:1859-1862, 1981; the solid phase phosphoramidite triester method described by Beaucage & Caruthers, *Tetra. Letts,* 22(20):1859-1862, 1981, for example, using an automated synthesizer as described in, for example, Needham-VanDevanter et al., *Nucleic Acids Res,* 12:6159-6168, 1984 and the solid support method of U.S. Pat. No. 4,458,066. Chemical synthesis produces a single-strand (ss) oligonucleotide, which can be converted into double-strand (ds) DNA by hybridization with a complementary sequence or by polymerization with a DNA polymerase using the single strand as a template. Exemplary nucleic acids that include sequences encoding IFNα and IFNγ polypeptides, effective fragments thereof, or variants thereof and a chimeric molecule (e.g., IL4-PE) polypeptide can be prepared by cloning techniques.

Nucleic acids encoding the IFNα and IFNγ polypeptides, effective fragments thereof, or variants thereof and a chimeric molecule (e.g., IL4-PE) polypeptide can be cloned or amplified by in vitro methods, such as the polymerase chain reaction (PCR), the ligase chain reaction (LCR), the transcription-based amplification system (TAS), the self-sustained sequence replication system (3SR), and the Qβ replicase amplification system (QB). For example, a polynucleotide encoding the protein can be isolated by a polymerase chain reaction of cDNA using primers based on the DNA sequence of the molecule. A wide variety of cloning and in vitro amplification methodologies are well-known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, Stockton Press, N Y, 1989. Polynucleotides also can be isolated by screening genomic or cDNA libraries with probes selected from the sequences of the desired polynucleotide under stringent hybridization conditions.

In the context of the compositions and methods described herein, a nucleic acid sequence that encodes IFNα and/or IFNγ polypeptides, effective fragments thereof, or variants thereof and/or a chimeric polypeptide (e.g., IL4-PE), such as described above, a variant thereof, or a fusion protein thereof, is incorporated into a vector capable of expression in a host cell, using established molecular biology procedures. For example, nucleic acids, such as cDNAs, that encode IFNα and/or IFNγ polypeptides, effective fragments thereof, or variants thereof and/or a chimeric polypeptide (e.g., IL4-PE) can be manipulated with standard procedures, such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate, or use of specific oligonucleotides in combination with PCR or other in vitro amplification.

Exemplary procedures sufficient to guide one of ordinary skill in the art through the production of a vector capable of expression in a host cell that includes a polynucleotide sequence encoding IFNα and/or IFNγ polypeptides, effective fragments thereof, or variants thereof and/or a chimeric polypeptide (e.g., IL4-PE) can be found, for example, in Sambrook et al., *Molecular Cloning: A Laboratory Manual*, 2nd ed., Cold Spring Harbor Laboratory Press, 1989; Sambrook et al., *Molecular Cloning: A Laboratory Manual*, 3rd ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., *Wiley & Sons*, 1999.

Typically, polynucleotide sequences encoding IFNα and/or IFNγ polypeptides, effective fragments thereof, or variants thereof and/or a chimeric polypeptide (e.g., IL4-PE) are operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are include promoters isolated from mammalian genes, such as the immunoglobulin heavy chain, immunoglobulin light chain, T cell receptor, HLA DQ α and DQ β,β-interferon, interleukin-2, interleukin-2 receptor, MHC class II, HLA-DRα,β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), al-antitrypsin, H2B (TH2B) histone, type I collagen, glucose-regulated proteins (GRP94 and GRP78), rat growth hormone, human serum amyloid A (SAA), troponin I (TNI), platelet-derived growth factor, dystrophin, and T cells as well as promoters specific for cancer cells, such as ovarian cancer, lung cancer, liver cancer, melanoma, osteosarcoma, and brain cancer cells.

The promoter can be either inducible or constitutive. An inducible promoter is a promoter that is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2 kb, HSP70, proliferin, tumor necrosis factor, or thyroid stimulating hormone gene promoter. Typically, the promoter is a constitutive promoter that results in high levels of transcription upon introduction into a host cell in the absence of additional factors. Optionally, transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40, and the herpes simplex virus thymidine kinase genes.

The polynucleotides encoding IFNα and/or IFNγ polypeptides, effective fragments thereof, or variants thereof and/or a chimeric polypeptide (e.g., IL4-PE) include a recombinant DNA, which is incorporated into a vector in an autonomously replicating plasmid or virus or into the genomic DNA of a prokaryote or eukaryote or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors that encode the IFNα and/or IFNγ polypeptides, effective fragments thereof, or variants thereof and/or a chimeric polypeptide can also be prepared. A number of viral vectors have been constructed, including polyoma; SV40 (Madzak et al., 1992, J. Gen. Virol., 73:15331536); adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256); vaccinia virus (Mackett et al., 1992, Biotechnology, 24:495-499); adeno-associated virus (Muzyczka, 1992, Curr. Top. Microbiol. Immunol., 158:91-123; On et al., 1990, Gene, 89:279-282); herpes viruses, including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199); Sindbis viruses (H. Herweijer et al., 1995, Human Gene Therapy 6:1161-1167; U.S. Pat. Nos. 5,091,309 and 5,2217,879); alphaviruses (S. Schlesinger, 1993, Trends Biotechnol. 11:18-22; I. Frolov et al., 1996, Proc. Natl. Acad. Sci. USA 93:11371-11377); and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors are also known in the art and may be obtained from commercial sources (such as PharMingen, San Diego, Calif.; Protein Sciences Corp., Meriden, Conn.; Stratagene, La Jolla, Calif.).

Thus, in one embodiment, polynucleotides encoding IFNα and/or IFNγ polypeptides, effective fragments thereof, or variants thereof and/or a chimeric polypeptide (e.g., IL4-PE) are included in one or more viral vectors. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors, and poliovirus vectors. Specific exemplary vectors are poxvirus vectors, such as vaccinia virus, fowlpox virus and a highly attenuated vaccinia virus (MVA), adenovirus, baculovirus, yeast, and the like.

It is understood that portions of the nucleic acid sequences encoding IFNα and/or IFNγ polypeptides, effective fragments thereof, or variants thereof and/or a chimeric polypeptide (e.g., IL4-PE) can be deleted as long as the polypeptides are functionally active. For example, it may be desirable to delete the nucleotides encoding one or more amino acids from the N-terminus, C-terminus, or both. It is also contemplated that substitution of nucleotides that encode residues in IFNα and/or IFNγ polypeptides, effective fragments thereof, or variants thereof and/or a chimeric polypeptide (e.g., IL4-PE) can be, for example, conservative substitutions, such that the functionality of the IFNα and/or IFNγ polypeptides, effective fragments thereof, or variants thereof and/or a chimeric polypeptide (e.g., IL4-PE) is maintained (see above).

Compositions and Methods of Treating Cancer

Compositions and methods are provided herein for treating cancer and/or a tumor in a subject, such as a mammalian subject, for example a human subject or veterinary subject.

In some examples, the methods can ameliorate a sign or symptom of cancer (e.g., a solid tumor, such as an ovarian tumor or a malignant cancer, such as, but not limited to, ovarian cancer) in a subject. In some non-limiting examples, the methods can induce remission or cure cancer in a subject, such as by reducing tumor size or burden, signs or symptoms of a tumor (such as cachexia), metastasis, or combinations thereof. In some examples, the method can prevent cancer, for example by inhibiting the full development of cancer, such as decreasing the ability of a tumor to metastasize. In further examples, the subject has a benign tumor, and the methods can be used to reduce the tumor size or burden.

The methods include administering an IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules, to the subject with cancer. In some examples, the IFNα and IFNγ can be human IFNα and human IFNγ. The methods also include administering a chimeric molecule, including an agent that specifically binds IL-4R and a toxin, or a nucleic acid molecule encoding the chimeric molecule. The chimeric molecule can include a circularly permuted molecule, such as circularly permuted IL-4R-binding agent and a toxin. In some examples, the agent that specifically binds IL-4R can be IL-4 or an effective fragment or variant thereof. In further examples, the IL-4R can be IL-4 or an effective fragment or variant thereof can be human. In other examples, the agent that specifically binds IL-4R can be an antibody that specifically binds IL-4R or an antigen-binding fragment, such as Fab', (Fab')$_2$, single chain (sc)Fv, or disulfide stabilized (ds)Fv.

In some examples, the toxin can be Pseudomonas exotoxin (PE), ricin A, abrin, ribotoxin, ribonuclease, saporin, calicheamycin, Diphtheria toxin, botulinum toxin, pokeweed antiviral toxin, bryodin 1, Clostridium perfringens enterotoxin (CPE), Cholera toxin, BAD (BCL-2 associated death prompter protein), ribosome-inactivating toxins or a cytotoxic fragment or variant thereof. In some examples, the toxin can be a chemotherapeutic agent. Examples of chemotherapeutic agents can include taxane, carboplatin, cyclophosphamide, and/or doxorubicin. In certain examples, the toxin is PE or a cytotoxic fragment or variant thereof. For example, the PE can be PE38 or PE40 (e.g., U.S. Pat. Nos. 6,011,002; 5,458,878, which are incorporated by reference herein). In some examples, the chimeric molecule can include IL-4 and PE (e.g., a chimeric protein that includes circularly permuted IL-4 and PE, see U.S. Pat. No. 6,011,002, incorporated by reference herein).

The methods can include selecting a subject with cancer. In some methods, the cancer is an ovarian cancer, a lung cancer, a liver cancer, a melanoma, an osteosarcoma, or a brain cancer or a tumor that is solid or malignant. The methods include administering the IFNα and IFNγ polypeptide, effective fragments thereof, or variants thereof and chimeric molecule and/or nucleic acid molecules encoding the IFNα and IFNγ polypeptide, effective fragments thereof, or variants thereof and chimeric molecules to the subject with cancer.

In some examples, the method includes selecting a subject with ovarian cancer. Any form of ovarian cancer can be treated using the IFNα and IFNγ polypeptide, effective fragments thereof, or variants thereof and chimeric molecule and/or nucleic acid molecules encoding the IFNα and IFNγ polypeptide, effective fragments thereof, or variants thereof and chimeric molecules. In some non-limiting examples, the subject can have ovarian carcinoma, papillary serous cystadenocarcinoma, mucinous cystadenocarcinoma, endometrioid tumors, Brenner tumors, clear cell carcinoma, unclassified carcinoma, granulosa-thecal cell tumors, Sertoli-Leydig cell tumors, dysgerminoma, and malignant teratoma. The methods can also be used to treat ovarian cancer at any stage.

In some examples, the method includes selecting a subject with lung cancer. Any form of lung cancer can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have non-small cell lung cancer (e.g., any type of adenocarcinoma, squamous cell carcinoma, large cell carcinoma, and large cell neuroendocrine tumors), small cell lung cancer, mesothelioma, or carcinoid tumors. The methods can also be used to treat lung cancer at any stage.

In some examples, the method includes selecting a subject with liver cancer. Any form of liver cancer can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have primary liver cancer (e.g, hepatocellular carcinoma, intrahepatic cholangiocarcinoma, angiosarcoma, hemangiosarcoma, and hepatoblastoma) or secondary liver cancer (i.e., metastatic liver cancer). The methods can also be used to treat liver cancer at any stage.

In some examples, the method includes selecting a subject with melanoma. Any form of melanoma can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have superficial spreading melanoma, nodular melanoma, lentigo maligna melanoma, acral lentiginous melanoma, desmoplastic melanoma, ocular melanoma, and anorectal melanoma. The methods can also be used to treat melanoma at any stage.

In some examples, the method includes selecting a subject with an osteosarcoma. Any form of osteosarcoma can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have a high-grade osteosarcoma, such as osteoblastic, chondroblastic, fibroblastic, mixed, small cell, telangiectatic, high-grade surface (i.e., juxtacortical high grade), pagetoid, extra-skeletal, and post-radiation; intermediate-grade osteosarcoma, such as periosteal (i.e., juxtacortical intermediate grade); or low-grade osteosarcoma, such as parosteal (i.e., juxtacortical low grade) and intramedullary or intraosseous well differentiated (i.e., low-grade central). The methods can also be used to treat osteosarcoma at any stage.

In some examples, the method includes selecting a subject with brain cancer Any form of brain cancer can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have primary brain cancer (e.g., astrocytomas, meningiomas, and oligodendrogliomas) or secondary brain cancer. The methods can also be used to treat brain cancer at any stage.

In some examples, the methods include selecting a subject with a solid or malignant tumor. Any form or solid or malignant tumor can be treated using the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE). In some non-limiting examples, the subject can have a sarcoma, carcinoma, germ cell tumor, blastoma, or lymphoma, including fibrosarcoma, myxosarcoma, liposarcoma, chondrosarcoma, osteogenic sarcoma, other sarcomas, synovioma, mesothelioma, Ewing's sarcoma (tumor), leiomyosarcoma, rhabdomyosarcoma, colon carcinoma, lymphoid malignancy, pancreatic cancer, breast cancer (including basal breast carcinoma, ductal carcinoma, and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, head cancer, neck cancer, CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma), yolk sac tumors, germinomas, choriocarcinomas, hepatoblastoma, medulloblastoma, nephroblastoma (e.g., Wilms' tumor), neuroblastoma, retinoblastoma, pancreatoblastoma, or pleuropulmonary blastoma. The methods can also be used to treat solid malignant tumors at any stage.

In some examples, the subject is administered an additional protocol and/or pharmaceutical agent. Examples of additional protocols that can be administered include, but are not limited to, a therapeutically effective amount of surgery, chemotherapy, hormone therapy, radiation therapy, immunotherapy (e.g., cell-based, protein-based, nucleic acid-based therapy, and/or polysaccharide-based therapy), and/or a vaccine (e.g., for a subject with ovarian cancer). In specific, non-limiting examples, the immunotherapy includes adoptive cell transfer using cells of interest, such as monocytes). In some examples, the adoptive cell transfer can include transfer of monocytes (e.g., monocytes and/or monocyte-derived cells, such as macrophages or dendritic cells). In some examples, the adoptive cell therapy can include a preparative regimen (e.g., immunodepletion before administration of the cells of interest, such as administering cyclophosphamide and/or fludarabine). In some examples, the adoptive cell therapy can include co-administering an agent to enhance efficacy of the cells of interest (e.g., IL-2). In specific, non-limiting examples, the adoptive cell therapy can include administering the cells of interest (e.g., monocytes) at a dose of at least about $10^3$, $10^4$, $10^5$, $10^6$, $10^7$, $10^8$, $10^9$, or $10^{10}$ cells, or about $10^6$, such as at least about $10^6$, $50\times10^6$, $75\times10^6$, $100\times10^6$, $200\times10^6$, $300\times10^6$, $400\times10^6$, $500\times10^6$, or $750\times10^6$ cells for at least about 1, 2, 3, 4, 5, 6, 7, 8, 9, or 10 doses or at least about a daily, biweekly, weekly, bimonthly, or monthly dose.

In additional embodiments, the subject can be administered an additional pharmaceutical agent, such as a chemotherapeutic or immunotherapeutic agent. The phrase "combinatorial therapy" or "combination therapy" not only embraces the administration of the IFNα and IFNγ polypeptide, effective fragments thereof, or variants thereof and chimeric molecule (e.g., IL4-PE) and nucleic acid molecules encoding the IFNα and IFNγ polypeptide, effective fragments thereof, or variants thereof and chimeric molecules (e.g., IL4-PE) but also the addition of one or more therapeutic agents as part of a specific treatment regimen intended to provide beneficial effect from the co-action of these therapeutic agents. In some examples, the additional therapeutic agent is a taxane, a carboplatin, a cisplatin (e.g., PLATINOL-AQ®, and PLATINOL®), a cyclophosphamide (or clafen; e.g., CYTOXAN®), a doxorubicin, and/or an antibody that targets and/or apparently targets programmed cell death (PD)-1 and/or PD-ligand 1 (PD-L1), such as atezolizumab (i.e., MPDL3280A and/or RG7446; e.g., TECENTRIQ®), nivolumab (i.e., BMS-936558, MDX-1106, and/or ONO-4538; e.g., OPDIVO®), pembrolizumab (i.e., MK-3475 and/or lambrolizumab; e.g., KEYTRUDA®), BMS 936559 (i.e., MDX-1105), durvalumab (i.e., MEDI-4736; e.g., IMFINZI®), AMP-224, and avelumab (i.e., MSB0010718C and/or MSB0010682; e.g., BAVENCIO®).

Exemplary chemotherapeutic agents include melphalan (e.g., ALKERAN®), bevacizumab (e.g., AVASTIN®), doxorubicin liposome (e.g., EVACET®, DOXIL®, DOXSL®, and LIPODOX®), gemcitabine hydrochloride (e.g., GEMZAR®), topotecan (HYCAMTIN®), olaparib (e.g., LYNPARZA®), paclitaxel (e.g., TAXOL®), rucaparib camsylate (e.g., RUBRACA®), thiotepa. topotecan hydrochloride (e.g., HYCAMTIN®), and niraparib tosylate monohydrate (e.g., ZEJULA®). Exemplary combinations of additional chemotherapeutic agents include bleomycin, etoposide phosphate, and cisplatin; carboplatin and paclitaxel; gemcitabine hydrochloride and cisplatin; carboplatin, etoposide phosphate, and bleomycin; cisplatin, etoposide phosphate, and bleomycin; vincristine sulfate, dactinomycin (e.g., ACTINOMYCIN-D®), and cyclophosphamide; and vincristine sulfate, ifosfamide, and cisplatin.

Examples of other chemotherapeutics that can be used include methotrexate (e.g., RHEUMATREX®, TREXALL®, ABITREXATE®, FOLEX PFS®, FOLEX®, METHOTREXATE LPF®, MEXATE-AQ®, and MEXATE®), paclitaxel albumin-stabilized nanoparticle formulation (e.g., ABRAXANE®), afatinib dimaleate (e.g., GILOTRIF®), everolimus (e.g., AFINITOR® and ZORTRESS®), alectinib (e.g., ALECENSA®), pemetrexed disodium (e.g., ALIMTA®), brigatinib (e.g., ALUNBRIG®), bevacizumab (e.g., AVASTIN®), brigatinib (e.g., ALUNBRIG®), ceritinib (e.g., ZYKADIA®), crizotinib (e.g., XALKORI®), ramucirumab (e.g., CYRAMZA®), docetaxel (e.g., DOCEFREZ® and TAXOTERE®), erlotinib hydrochloride (e.g., TARCEVA®), everolimus (e.g., AFINITOR® and ZORTRESS®), gefitinib (e.g., IRESSA®), afatinib dimaleate (e.g., GILOTRIF®), mechlorethamine hydrochloride (e.g., MUSTARGEN®), vinorelbine tartrate (e.g., NAVELBINE®), necitumumab (e.g., PORTRAZZA®), ramucirumab (e.g., CYRAMZA®), osimertinib (e.g., TAGRISSO®), erlotinib hydrochloride (e.g., TARCEVA®), etoposide phosphate (e.g., ETOPOPHOS®), sorafenib tosylate (e.g., NEXAVAR®), regorafenib (e.g., STIVARGA®), aldesleukin (e.g., PROLEUKIN®), cobimetinib (e.g., COTELLIC®), dabrafenib (e.g., TAFINLAR®), dacarbazine (e.g., DTIC-DOME®), talimogene laherparepvec (e.g., IMLYGIC®), ipilimumab (e.g., YERVOY®), trametinib (e.g., MEKINIST®), vemurafenib (e.g., ZELBORAF®), dactinomycin (e.g., COSMEGEN®), denosumab (e.g., PROLIA® and XGEVA®), carmustine (e.g., BECENUM®, BiCNU®, GLIADEL®, and CARMUBRIS®), lomustine (e.g., GLEOSTINE®), pidilizumab (i.e., CT-011), and temozolomide (e.g., METHAZOLASTONE® and TEMODAR®). Exemplary combinations of additional chemotherapeutic agents include procarbazine hydrochloride, lomustine, and vincristine sulfate.

For any of the methods disclosed herein, the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE) can be administered systemically or locally. In some embodiments, the IFNα and IFNγ polypeptide, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE) are administered locally to the site of the tumor. In some non-limiting examples, the administration can be intraperitoneal, such as to treat ovarian cancer.

Pharmaceutical Compositions of Use for Treating Cancer

Provided herein are pharmaceutical compositions that include the IFNα and IFNγ polypeptide, effective fragments thereof, or variants thereof and chimeric molecules (e.g., IL4-PE) that bind IL-4R and include a toxic moiety (e.g., IL4-PE) and nucleic acid molecules encoding the IFNα and IFNγ polypeptide, effective fragments thereof, or variants thereof and chimeric molecules (e.g., IL4-PE) disclosed herein. The pharmaceutical compositions can be formulated and administered in a variety of ways depending on the location and type of cancer to be treated.

These pharmaceutical compositions are of use in the methods disclosed herein. Pharmaceutical compositions are provided for use by any subject, such as a mammalian or human subject. The subject can have a cancer that expresses IL-4R, such as a solid tumor or a malignant cancer. The subject can have an ovarian cancer (e.g., ovarian carcinoma, papillary serous cystadenocarcinoma, mucinous cystadenocarcinoma, endometrioid tumors, Brenner tumors, clear cell carcinoma, unclassified carcinoma, granulosa-thecal cell tumors, Sertoli-Leydig cell tumors, dysgerminoma, or malignant teratoma), a lung cancer (e.g., non-small cell lung cancer or small cell lung cancer, mesothelioma, or carcinoid tumors), a liver cancer (e.g., primary liver cancer, such as hepatocellular carcinoma, intrahepatic cholangiocarcinoma, angiosarcoma, hemangiosarcoma, and hepatoblastoma, or secondary liver cancer), a melanoma (e.g., superficial spreading melanoma, nodular melanoma, lentigo maligna melanoma, acral lentiginous melanoma, desmoplastic melanoma, ocular melanoma, and anorectal melanoma), an osteosarcoma (e.g., high-grade, intermediate-grade, or low-grade), or a brain cancer (e.g., primary brain cancer, such as astrocytomas, meningiomas, and oligodendrogliomas or secondary brain cancer). These pharmaceutical compositions are of use in to treat cancer at any stage.

The disclosure includes within its scope pharmaceutical compositions comprising IFNα and IFNγ polypeptides, effective fragments thereof, or variants thereof and chimeric molecules (e.g., IL4-PE) that bind IL-4R and include a toxic moiety. The disclosure also includes within its scope a pharmaceutical composition including a nucleic acid molecule encoding the IFNα and IFNγ polypeptide, effective fragments thereof, or variants thereof and chimeric molecules (e.g., IL4-PE) that bind IL-4R and include a toxic moiety. The pharmaceutical compositions can be formulated for use in human or veterinary medicine.

Generally, it is desirable to prepare the compositions as pharmaceutical compositions appropriate for the intended application. Accordingly, methods for making a medicament or pharmaceutical composition containing the polypeptides, nucleic acid molecules, or vectors described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for binding or uptake of polypeptides, nucleic acids, or virus by target cells.

Therapeutic compositions can be provided as parenteral compositions, such as for injection or infusion. Such compositions are formulated generally by mixing a disclosed therapeutic agent at the desired degree of purity in a unit dosage injectable form (solution, suspension, or emulsion) with a pharmaceutically acceptable carrier, for example, one that is non-toxic to recipients at the dosages and concentrations employed and is compatible with other ingredients of the formulation. In addition, a disclosed therapeutic agent can be suspended in an aqueous carrier, for example, in an isotonic or hypotonic buffer solution at a pH of about 3.0 to about 8.5, such as about 4.0 to about 8.0, about 5 to about 7.5, or about 5 to about 7. Useful buffers include phosphate-buffered saline.

The pharmaceutically acceptable carriers and excipients useful in this disclosure are conventional. For instance, parenteral formulations usually comprise fluids that are pharmaceutically and physiologically acceptable fluid vehicles, such as water, physiological saline, other balanced salt solutions, aqueous dextrose, glycerol, or the like. Excipients that can be included are, for instance, proteins, such as serum albumin (e.g., human serum albumin, "HSA," such as IL4-PE suspended in at least 0.1, 0.2, 0.3, or 0.5% HSA) or plasma preparations. If desired, the pharmaceutical composition to be administered may also contain minor amounts of non-toxic auxiliary substances, such as wetting or emulsifying agents, preservatives, pH buffering agents, and the like, for example, glycine, sodium acetate, or sorbitan monolaurate. The IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecule (e.g., IL4-PE) described herein can be formulated with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol, and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, and sodium bicarbonate. These agents can be present in amounts sufficient to maintain a pH of the system of between about 4 to about 8, about 5 to about 7.5, or at about 5 to about 7. As such, the buffering agent can be as much as 5% on a weight-to-weight basis of the total composition. Electrolytes, such as sodium chloride and potassium chloride, may also be included in the formulation. In some embodiments, polyethylene glycol (PEG) is coupled to an IFN (e.g., peginterferona-2b, such as PEG-INTRON® and/or SYLATRON®, peginterferona-2a, such as PEGASYS®, and peginterferonλ-1a; see U.S. Pat. No. 8,575,135, incorporated herein by reference). The proportions of the IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric (e.g., IL4-PE) molecule; added polymers; and any other modifiers may be empirically determined by formulating several carries with varying proportions. A USP-approved method for dissolution or release test can be used to measure the rate of release (USP 23; NF 18 (1995) pp. 1790-1798).

The active ingredient, optionally together with excipients (e.g., human serum albumin), can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the polypeptide, nucleic acid molecule, or dispersed (for example, dissolved or suspended) in a pharmaceutically acceptable carrier or excipient. Pharmaceutically acceptable carriers and/or pharmaceutically acceptable excipients are known in the art and are described, for example, in Remington's Pharmaceutical Sciences by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids, such as water, physiological saline, balanced salt solutions, aqueous dextrose, glycerol, or the like, as a vehicle. For solid compositions (such as powder, pill, tablet, or capsule forms), conventional non-toxic solid carriers can include, for example, pharmaceutical grades of mannitol, lactose, starch, or magnesium stearate. In addition, pharmaceutical compositions to be administered can contain minor amounts of non-toxic auxiliary substances, such as wetting or emulsifying agents, preservatives, pH buffering agents and the like, for example, sodium acetate or sorbitan monolaurate.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the polypeptides, polynucleotides, vectors, or viruses in an aqueous solution, mixed with a suitable surfactant, such as hydroxypropyl cellulose. Dispersions also can be prepared in glycerol, liquid polyethylene glycols, and mixtures thereof as well as in oils. Under ordinary conditions of storage and use, these preparations contain a preservative to prevent the growth of microorganisms.

Administration of therapeutic compositions can be locally or systemically by any common route as long as the target tissue available via that route (e.g., the site of the tumor, such as IP injection into the abdominal cavity for treatment of ovarian cancer). This further includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. In some embodiments, the IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE) are formulated for administration to the abdominal cavity, such as to treat ovarian cancer. The therapeutic agents can be administered by the same route or by different routes.

Such pharmaceutical compositions are usually administered as pharmaceutically acceptable compositions that include physiologically acceptable carriers, buffers, or other excipients. Pharmaceutical compositions that include the IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE) as an active ingredient can be formulated with an appropriate solid or liquid carrier, depending upon the particular mode of administration chosen. For instance, in addition to injectable fluids, topical and oral formulations can be employed. Topical preparations can include eye drops, ointments, sprays, and the like. Eye drops or sprays (e.g., for melanoma) can be provided in unit dose dispensers (such as eye drop bottles that dispense a metered unit dose containing IFNα and IFNγ polypeptides, effective fragments thereof, or variants thereof and a chimeric molecule (e.g., IL4-PE) and/or nucleic acid molecules encoding the IFNα and IFNγ polypeptide, effective fragments thereof, or variants thereof and chimeric molecules (e.g., IL4-PE), either alone or in combination with other therapeutic agents). Oral formulations may be liquid (e.g., syrups, solutions, or suspensions) or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known or will be apparent to those of ordinary skill in the art. Implants can also be employed (see below).

The pharmaceutical compositions that include the IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecules (e.g., IL4-PE) will, in some embodiments, be formulated in unit dosage form, suitable for individual administration of precise dosages. In some examples, the chimeric molecule (such as IL4-PE) can be administered to the subject at least at about 10-100 µg/Kg, 20-80 µg/Kg, 30-70 µg/Kg, 40-60 µg/Kg; about 20 µg/Kg, 30 µg/Kg, 40 µg/Kg, 50 µg/Kg, 60 µg/Kg, or 70 µg/Kg; or at least about 50 µg/Kg. In further examples, the IFNα and IFNγ polypeptides can be administered to the subject at least at about 50-100, 100-200, 200-300, 300-400, 400-500, 500-600, 600-700, or 800-900 µg; at least at about 100, 200, 300, or 600 µg; or at least at about 1-2, 2-3, 3-4, 4-5, 5-6, 6-7, 7-8, 8-9, 9-10, 10-15, or 15-20 µg/Kg or at least about 1-10 µg/Kg. In some examples, the IFNα is peginterferona-2b (e.g., SYLATRON®), and the subject is administered at least about 100, 200, 300, 400, 500, 600, 700, or 800 µg or at least about 200, 300, or 600 µg. In other examples, the IFNα is peginterferona-2a (e.g., ROFERON A®), and the subject is administered at least about 1, 2, 3, 4, 5, 6, 7, or 8 million IU or at least about 3 or 6 million IU. In further examples, the IFNγ is IFNγ-1b (e.g., ACTIMMUNE®), and the subject is administered at least about 50, 100, or 200 µg or at least about 100 µg.

The amount of active compound(s) administered will depend on the subject being treated, the severity of the affliction, and the manner of administration and is best left to the judgment of the prescribing clinician. Within these bounds, the formulation to be administered will contain a quantity of the active component(s) in amounts effective to achieve the desired effect in the subject being treated.

In some embodiments, the IFNα, IFNγ, and chimeric molecule (such as IL4-PE) can be administered to the subject multiple times, such as at least 2 times, at least 3 times, at least 4 times, at least 5 times, or about 3 times. In other embodiments the IFNα, IFNγ, and chimeric molecule (such as IL4-PE) can be administered over long periods of time, such as daily, multiple times per week, weekly, multiple times per month, or monthly. Administration of these therapeutic agents in combination typically is carried out over a defined period (usually minutes, hours, days, weeks, or months, depending on the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject an individual dose having a fixed ratio of each therapeutic agent or in multiple, individual doses for each of the therapeutic agents. Sequential or substantially simultaneous administration of each therapeutic agent can be affected by any appropriate route. Any of the compositions disclosed above can be used in the presently claimed methods. The IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecule (e.g., IL4-PE) can be formulated with additional therapeutic agents. Exemplary agents include chemotherapeutic agents and/or immunotherapeutic agents (e.g., monocytes). In specific non-limiting examples, the IFNα and IFNγ polypeptides, effective fragments thereof, or variants thereof and chimeric molecule (e.g., IL4-PE) and/or nucleic acid molecules encoding the IFNα and IFNγ polypeptide, effective fragments thereof, or variants thereof and chimeric molecule (e.g., IL4-PE) can be formulated with monocytes (e.g., at a dose of at least about $10^3$, $10^4$, $10^5$, $10^6$, $10^7$, $10^8$, $10^9$, or $10^{10}$ cells, or about $10^6$, such as at least about $10^6$, $50 \times 10^6$, $75 \times 10^6$, $100 \times 10^6$, $200 \times 10^6$, $300 \times 10^6$, $400 \times 10^6$, $500 \times 10^6$, or $750 \times 10^6$ cells for at least about 1, 2, 3, 4, 5, 6, 7, 8, 9, or 10 doses or at least about a daily, biweekly, weekly, bimonthly, or monthly dose).

Any of the administration methods and/or compositions disclosed above can be utilized. More than one method of administration also can also be utilized, such as a combination of injection methods or an injection method combined with oral administrate. Local and/or topical administration can also be combined with systemic administration. In one embodiment, a sign or a symptom of the cancer is decreased or alleviated. One polypeptide or polynucleotide, or multiple polypeptides and polynucleotides can be utilized.

EXAMPLES

It is disclosed herein that IFNs and IL4-PE are synergistic in vitro as measured by cytotoxicity assays. Intracellular signaling and the activation of cell death (apoptosis) by IFNs and IL4-PE in ovarian cancer cell lines. Western blot analyses showed that IFNs and IL-4PE induced STAT1 and STAT6 phosphorylation, respectively. Jak inhibitor studies using tofacitinib and ruxolitinib showed that cytotoxicity depended on IFN and was independent of IL-4 signaling, showing that the two signaling pathways do not interact to cause cell death. Apoptosis was assessed by western blot analysis for PARP, caspase-3, and caspase-7, which showed that both IFNs and IL-4PE activated critical proteins in the apoptosis pathway (see also, Du et al., *Molecular and Cellular Biology*, 30(14):3444-52, 2010, showing that IL-4PE induces apoptosis).

In addition, the antitumor effects of a combination therapy in vivo were investigated. An intraperitoneal metastatic ovarian tumor model was generated in immune-deficient animals. An aggressive human ovarian cancer cell line (A2780) was injected i.p. and generated a rapid and dispersed disease within the peritoneal cavity. The animals succumbed to disease with median survival time of 35 to 55 days. Consistent with the in vitro results, a combination of IFNs and IL-4PE mediated synergistic antitumor effects when administered in vivo. This antitumor effect was assessed by overall survival of ovarian cancer-bearing animals and autopsy findings. A combination of IFNs and IL4-PE resulted in a statistically significant higher survival of animals compared with individual treatment groups. Despite the aggressive nature of this ovarian cancer model, approximately 33% of animals survived in the combination group with 24% scored as having a CR.

A notable feature of the combination therapy is that a suboptimal dose of IL4-PE (50 µg/kg, qod, x3; total dose: 150 µg/kg) with interferons alpha and gamma (200 ng/ml each) administered via IP resulted in decreased tumor burden with prolonged overall survival. The combination therapy yielded 38% complete responders (8/21 treated mice) in all three experiments. A known limitation to therapy is the formation of host-neutralizing antibodies to the PE toxin, which typically limits the treatment window to approximately 2 weeks with the most significant toxicity being reversible elevated liver enzymes. However, in this study, histological and macroscopic studies of organs (heart, lung, liver spleen, and kidney) showed no apparent sign of toxicity. The treated animals did not show changes in weight or other clinical measurements of animal health.

Without being bound by theory, the route of administration directly into the peritoneum could change the toxicity profile by increasing the concentration at the site of disease and decreasing systemic concentration. These results showed that IFN immunotherapy with a targeted IL4-PE drug is useful for managing patients with ovarian cancer.

Supporting the animal survival results, longitudinal imaging using gaussia luciferase imaging technology was performed. Ovarian tumor cells were stably transduced with a vector containing luciferase, and chemiluminescence was measured by IVIS imaging system after iv injection of luciferin. Further demonstrating the synergistic action in vivo, tumor histology was performed, showing a decrease in the amount of Ki-67 staining in the combination treatment group. The decrease in the proliferation marker showed that the combination treatment decreased the proliferative capacity of the cells.

The combination therapy did not mediate visible signs of toxicity, as animals being treated did not show changes in body weight or other clinical measurements of animal health. In addition, no gross toxicity was observed in peritoneal organs, as assessed by histology. These data are consistent with limited toxicity of IFNs to normal cells in vitro, despite the anti-proliferative effects in cancer cells. Similarly, due to low level expression of IL-4R in normal cells, including resting immune cells, IL4-PE has limited toxicity in normal cells. IL-4PE has been administered i.v. in Phase 1 clinical trials for the treatment of advanced solid tumors and shown dose-limiting reversible liver enzyme elevation (Garland et al., *Journal of Immunotherapy*, 28(4): 376-81, 2005). In addition, the novel route of administration directly into the peritoneal cavity can effect toxicity profiles in the clinical trials by increasing the concentration at the site of disease and decreasing systemic concentrations.

The combination therapy along with the administration of the agents IP provides a new cytokine and fusion toxin protein therapy for the treatment of cancer, such as, but not limited to, relapsed metastatic ovarian cancer.

Example 1

Materials and Methods

This example describes the methods used to generate the results described herein.

Cell Lines, IFNs, Chemical Inhibitors

OVCAR-5 and OVCAR-8 cells were obtained from the National Cancer Institute, National Institutes of Health (NIH). The A2780 cell line was obtained from ATCC® (Manassas, Va.). All cell lines were verified via short tandem repeat analysis (Hsu et al., *Int J Mol Sci*, 14:57-71, 2012). Cell lines were maintained in RPMI-1640 (LIFE TECHNOLOGIES®, Grand Island, N.Y.) supplemented with 10% FBS, 1% L-glutamine No antibiotics or anti-fungal agents were added to the cultures. Monocytes were obtained from healthy human donors.

Human IFN-α2a was a gift of Hoffmann LaRoche (Nutley, N.J.), PEGylated IFN-α2b (SYLATRON®) was purchased from MERCK®, Kenilwork N.J., and IFN-γ was purchased from INTERMUNE® Pharmaceutical Inc. (Brisbane, Calif.). Ruxolitinib (TOCRIS® Bioscience) and tofacitinib (TOCRIS® Bioscience) were purchased from SELLECKCHEM® (Houston, Tex.) and suspended in DMSO. Chemicals were stored at −20° C.

Recombinant IL-4 *Pseudomonas* Exotoxin (PE) Production

A recombinant chimeric protein comprised of human interleukin-4 (IL-4) and *Pseudomonas* exotoxin (IL-4-PE38KDEL) was produced by fusing a circularly permuted IL-4 mutant gene encoding IL-4 amino acids 38-129, the GGNGG linker, and IL-4 amino acids 1-37 with a truncated *Pseudomonas* exotoxin gene encoding PE38KDEL. This chimeric gene was expressed in *E. coli*, and highly purified protein was isolated on ion exchange and gel filtration columns (Kreitman et al., *Proc Natl Acad Sci USA*, 91:6889-6893, 1994; Puri et al., *J Immunol*, 152:3693-3700, 1994; Puri et al., *Cell Immunol*, 154:369-379, 1994). Recombinant IL-4-PE38KDEL (also referred to as IL4-PE) was reconstituted in PBS and stored at −80° C. The IL4-PE was not used after 1 freeze-thaw cycle.

Cytotoxicity Assays

Cell lines were seeded at $10^4$ cells/well in a 96-well plate in 100 µL of media and incubated until adherence (4 hr, 37° C., 5% $CO_2$). Serial dilutions of IL4-PE, IFN-α2a, or IFN-γ were added and incubated for three days. IFNs were diluted using serial dilutions in cRPMI to obtain a final concentration of 200 ng/mL of both IFN-α2a or IFN-γ. For ruxolitinib and tofacitinib studies, 10 µM (final concentration) was added to the plates and incubated at 37° C. for 2 hours before IFNs or IL4-PE was added. The media was then removed, and cell viability was determined by crystal violet dye uptake in fixed, live cells. Crystal violet is a triarylmethane dye that binds to ribose type molecules such as DNA in nuclei. The dye staining is directly proportional to the cell biomass. Dye absorbance was measured at 570 nm using a spectrophotometer.

Western Blots

Cell pellets were snap-frozen and stored at −80° C. Pellets were thawed and lysed with MPER buffer supplemented with protease inhibitors. Cell lysates were centrifuged at 13,000 RPM at 4° C. for 20 minutes to clarify the lysate. The clarified lysate was removed and placed in a new vial. The protein concentration was measured using a NANODROP® Spectrophotometer (LIFE TECHNOLOGIES®, Wilmington, Del.). The lysate was mixed with reducing loading buffer (LIFE TECHNOLOGIES®, Waltham Mass.) and heated at 90° C. for 10 minutes. The samples were allowed to cool and were either used immediately or stored at 4° C. for future analysis. The samples were analyzed using 10% Bis-Tris gels and then transferred to nitrocellulose membranes per the manufacturer's directions. The nitrocellulose blots were first blocked with 4% milk in TBST for 1 hour at room temperature. The membranes were incubated with a primary antibody overnight in 4% milk in TBST. The membranes were then developed using an ECL reagent (PIERCE®, Waltham Mass.) as directed. Images were acquired using a LI-COR® Odyssey (LI-COR® Biosciences, Lincoln, Nebr.).

Antibodies

Antibodies to Caspase-3 (#9662), Caspase-7 (#12827), and PARP (#9542) were obtained from CELL SIGNALING TECHNOLOGY® Inc. (Danvers, Mass.), and antibodies to Heat Shock Protein 90 (sc-7947) and p38 (sc-535) were obtained from SANTA CRUZ BIOTECHNOLOGY® (Dallas, Tex.).

Human Ovarian Cancer Xenograft Model

The peritoneal ovarian tumor model was developed in female nude nu/nu mice that were 4 to 6 weeks old (about 20 g body weight). The mice were obtained from the National Cancer Institute-Frederick Cancer Center Animal Facilities, Frederick, Md., and were maintained in a barrier facility on HEPA-filtered racks in pathogen-free conditions with 12-hour light/12-hour dark cycles. All animal studies were conducted under an approved protocol in accordance with the principles and procedures outlined in the program description of Animal Care and Use Program of the Center for Biologics Evaluation and Research, Food and Drug Administration, Silver Spring, Md.

For tumor cell injection in generating the ovarian cancer model, A2780-Gluc cells (ovarian cancer cells; $2 \times 10^6/200$ μL/mouse) were injected directly into the peritoneum. On day 4 post-tumor cell transplantation, the mice were randomly divided into different therapeutic groups and a control group (5-6 mice in first and second experiment and 12 mice per group in the third experiment). The mice had similar weights in the various groups. The mice were injected with excipient PBS, IL4-PE (50 μg/kg resuspended in 0.2% human serum albumin), or a mixture of PEGylated IFN-α2b and IFN-γ both in PBS at 200 ng/ml each on alternating days for a total of 3 injections. One group of mice was injected with the combination of all three agents simultaneously at the same concentrations. All injections were administered IP.

Two mice were sacrificed one week after the last injection for monitoring early growth of tumors. The remainder of the mice were monitored for their survival for up to 175 days. Body weights of mice were measured, and mice with extremely distended abdomens were sacrificed and photographed immediately, tumors and organs were harvested for, tumor weight, toxicological, and histological studies.

Histology

Organs and tumors were removed and placed in 4% Paraformaldehyde in buffered saline. Tissues were imbedded in paraffin blocks and sectioned. Sections were stained with hematoxylin and eosin and stained with antibodies against Caspsase-3 (Clone #9661, CELL SIGNALING TECHNOLOGY®) and Ki-67 (Clone # MIB-1, DAKO®).

Statistical Analysis

The drug treatments were analyzed for significance via a Student's t-test and two-way ANOVA with a Bonferroni post-test analysis. For each graph, the data are mean±standard error of the mean with P-values≤0.05 (*P<0.05, P<0.01, *P<0.001, ****P<0.0001). All data were obtained from at least three different experiments, and statistical analysis was performed using GRAPHPAD® 7 Software (PRISM®, Irvine Calif.).

Synergism, additive effects, and antagonism for multiple drug treatments were quantified using combination index values (CI) obtained from CompuSyn software (Chou, *Pharmacol Rev,* 58:621-681, 2006). The in vivo data were analyzed for statistical significance using the Student's t-test and ANOVA. Survival curves were generated using the Kaplan-Meier method and compared using a two-tailed logrank test. The animal experiments were repeated three times.

Example 2

IL-4-PE, IFN-α, and IFN-γ Mediate a Synergistic Cytotoxic Effect in Ovarian Cancer Cell Lines In Vitro This example shows that IFNs and IL4-PE mediate a synergistic killing in vitro. Two ovarian cancer cell lines were assessed for the cytotoxic effects of IL4-PE, IFN-α, and IFN-γ, and the combination of all three. The OVCAR-5 cells are an IL4-PE-sensitive, IFNs-sensitive cell line, and the A2780 cells exhibit low sensitivity to IL4-PE and IFNs. For both cell lines, cytokine concentrations above and below the individual EC50s (half maximal effective concentration) for IL4-PE and IFNs were selected; concentrations ranging from 0.04 ng/mL to 40 ng/mL for IL4-PE and 0.16 to 200 ng/mL for the IFNs were used.

In the OVCAR-5 cells treated with the lowest cytokine concentration, there was a statistically significant difference between IL4-PE alone and the combination treatment (FIG. 1A). However, this difference was not mathematically synergistic (FIG. 2). There was a statistically significant difference in cell death between both the IL4-PE (0.2 ng/mL) alone, IFNs alone (0.8 ng/mL), and the combination thereof. The IFNs were added at equal concentrations (i.e., 0.8 ng/mL IFNα2a and 0.8 ng/mL IFNγ). The combination of the three agents yielded slightly more than 50% cell death. A combination analysis showed that this affect was synergistic (CI, 0.4). Treatment with 1.0 ng/mL IL4-PE and 4.0 ng/mL IFNs alone yielded greater than 50% killing in the OVCAR-5 cells. The combination treatment showed statistically significant killing compared with the single agents and yielded 97% cell death. This effect was highly synergistic (CI, 0.11). At the highest concentrations tested (5.0 ng/mL IL4-PE and 20.0 ng/mL IFNs), the combination treatment yielded 100% killing, which was also highly synergistic (CI, $26.2 \times 10^{-6}$).

Figure 1B:
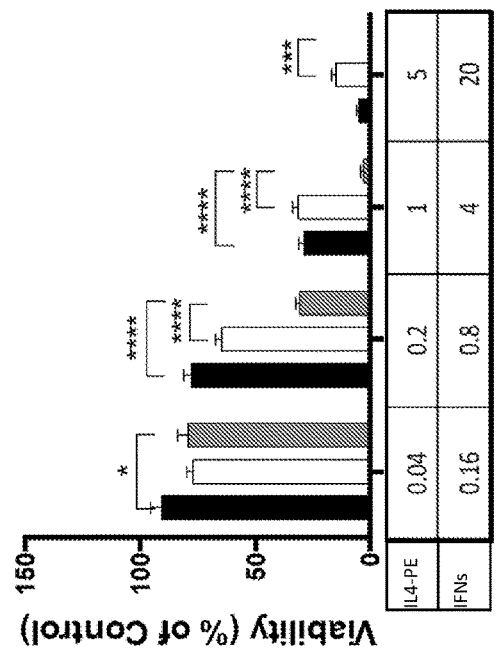

Compared with the OVCAR-5 cell line, the A2780 cell line is more refractory to both IL4-PE and IFNs with EC50s of the individual agents at approximately 8-fold and 10-fold higher (FIG. 1B). Similar to the OVCAR-5 cells, the difference between the IL4-PE and combination treatment was statistically significant as well as synergistic (CI, 0.5) (FIG. 2). At the three higher concentrations, the A2780 cells exhibited significant and synergistic killing with 100% cell death at the highest concentrations (IL4-PE, 40 ng/mL; IFNs, 200 ng/mL). Despite requiring high concentrations of both agents, the CI values of the A2780 treatment group were more synergistic in the A2780 cells than the OVCAR-5 cells (FIG. 2). The A2780 cells also exhibited a greater EC50 synergistic effect (CI, 0.24) than OVCAR-5 cells (CI, 0.58) (FIG. 2). The in vitro killing assays show that IL4-PE and the IFNs act synergistically to kill two ovarian cancer cell lines.

Example 3

The Combination of IL4-PE, IFNα, and IFNγ Increased Overall Survival of Tumor-Bearing Mice This example shows that the combination of IL4-PE, IFNα, and IFNγ can result in a complete response, despite a conservative dosing schedule, using a pre-clinical model of a cancer that expresses the IL-4R, human ovarian cancer.

Figure 3A:
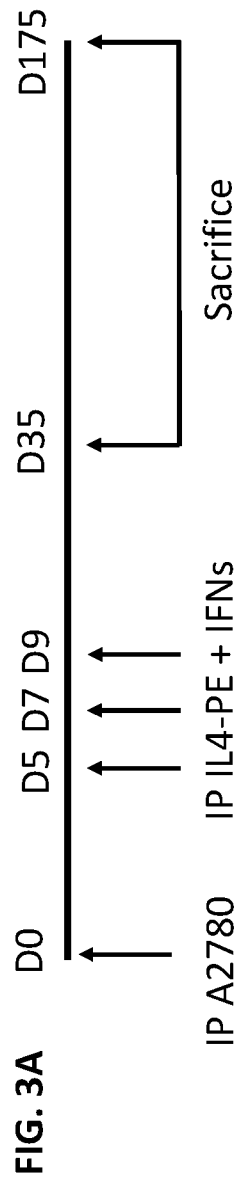
FIGS. 3A-3B: In vivo therapy model of IFNs and IL4-PE.
Figure 3B:
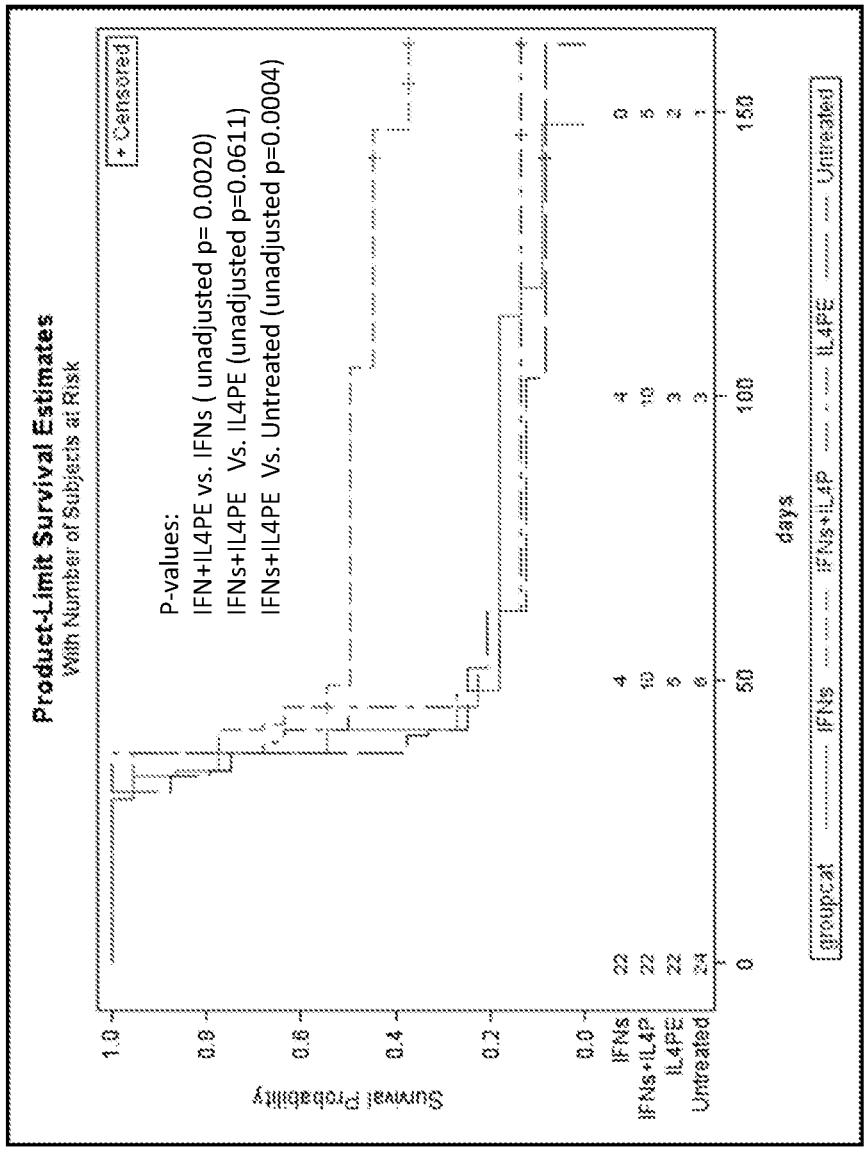

IP injection of A2780 cells into nude mice produces tumor formation throughout the peritoneal cavity, which models ovarian cancer in patients. To test the effect of IL4-PE and IFNs in vivo, a model was created that would follow the dosing schedule of IL-4PE in clinical trials (FIG. 3A). Mice received IP injections of saline, IL-4PE, IFNs, or the combination of both on days 5, 7, and 9. This model was repeated 3 times (FIG. 3B).

In the first experiment, 5 mice were randomized per group. By day 120, the entire IFN treatment group had died. At the termination of the experiment, on day 174, 1 of 5 animals in both the saline and IL-4PE group were alive. Three of the 5 animals in the combination treatment group survived until the termination of the experiment and were scored as having a complete response (CR) on necropsy.

In the second experiment, all of the animals (n=6) died both in the IL4-PE-treated group (by day 35) and in the saline group (by day 42). Five of the 6 mice died in the IFNs group by day 42 with one animal surviving to day 142. In the dual treatment group, 3 of the 6 animals died by day 42 with one dying on day 50. Two remaining mice survived until the termination of the experiment on day 155. The difference between the IL4-PE alone, IFNs alone, or saline treatment and the combination treatment groups was statistically significant (p=0.008).

In the third experiment, 10 out of 10 animals had died by day 49 in the IL4-PE treatment group. Nine out of 10 animals had also died by day 41 in the saline and IFNs groups. In the combination treatment group, 3 of the ten animals were alive at the termination of the experiment with all 3 scored as a CR. Statistical analysis showed a significant difference between IL4-PE alone, IFNs alone, or saline treatment and the combination treatment groups (p=0.0171). The saline control, IL4-PE, or IFNs alone treatment groups showed no statistically difference.

Due to the lower number of animals in the first experiment, the statistical survival probability analysis showed little difference among the four groups (global p=0.42), but the combination group appeared better. The individual groups in the second experiment also appeared to be similar, but because of the rapid events compared with the first experiment, the individual groups exhibited a trend of not being identical (global p=0.06). However, the percent survival in the combination group was statistically significant (p=0.008) compared with the other groups. With only 6 mice per group, the advantage of the survival probability in treated groups was inconclusive.

In the third experiment, more (n=10) animals per group were examined. The treatment was similar to the other two experiments, all individual groups differed from each other, and overall survival probability values was highly significant (global p=0.0086). The combination group (IFNs+IL4-PE) exhibited significantly better survival than the other three groups (saline, IFNs, or IL4-PE). The three p values for the combination vs. each of the other is between 0.0011 and 0.015.

Figure 4B:
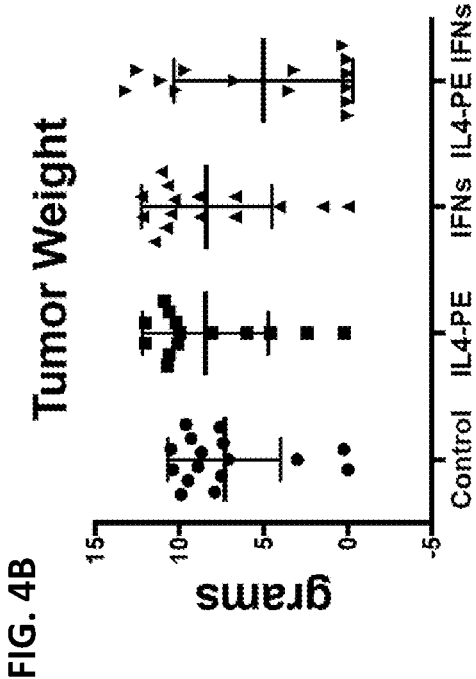
FIGS. 4A-4D: Quantification of disease using the in vivo therapy model in FIGS. 3A-3B. Total mouse weight (FIG. 4A), tumor weight (FIG. 4B), the ratio of tumor weight to mouse weight (FIG. 4C), and the ratio of tumor weight to days alive (FIG. 4D) from experiments 1 and 3.
Figure 4D:
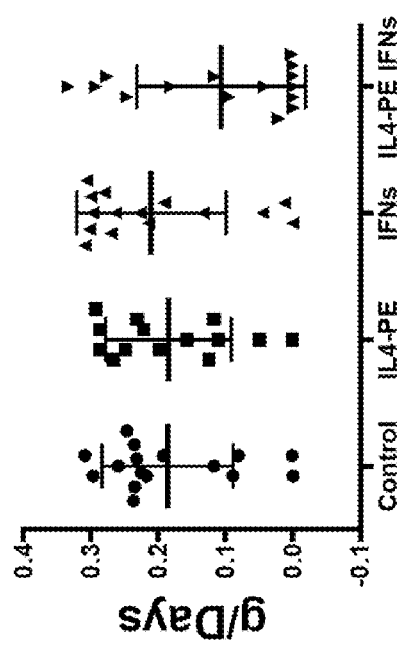
Figure 4A:
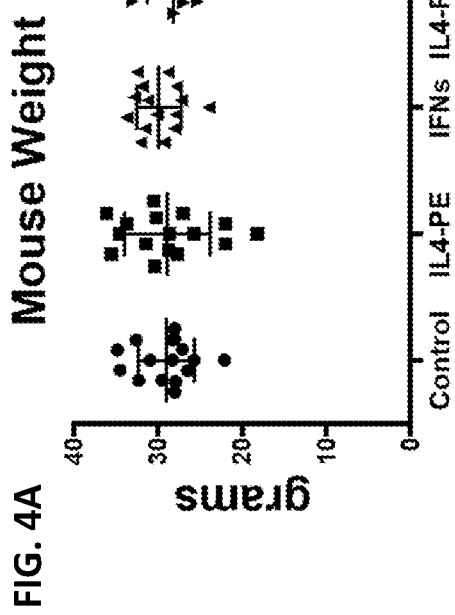
Figure 4C:
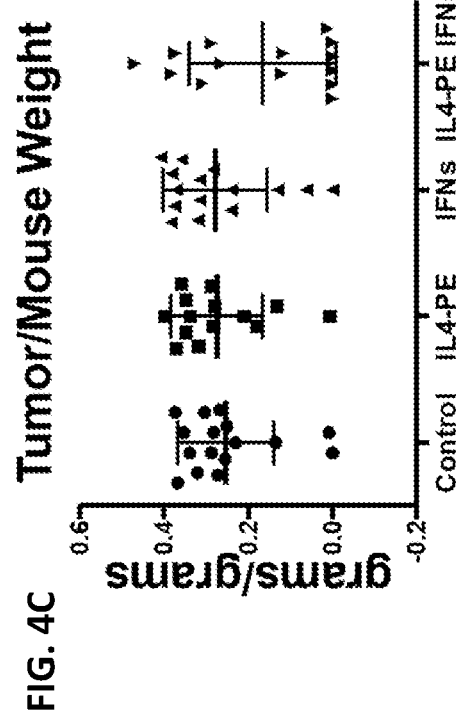
Figure 5A:
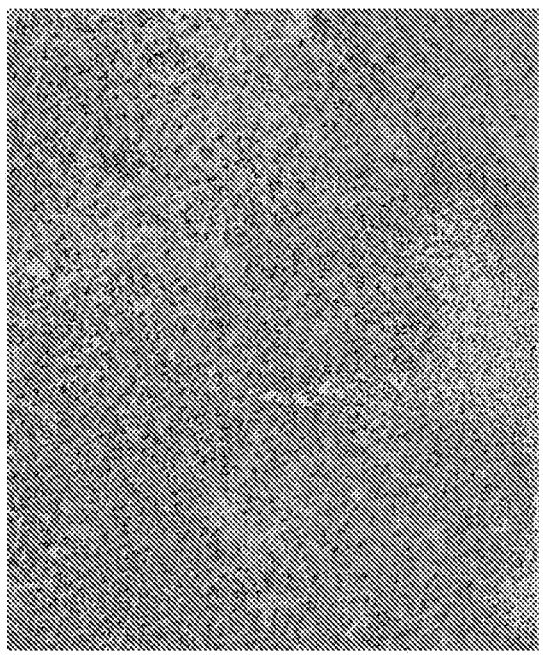
FIGS. 5A-5D: Ki-67 staining of tumors. Peritoneal tumors were fixed and stained for Ki-67. Representative images from one mouse, control (FIG. 5A), IFNs (FIG. 5B), IL-4PE (FIG. 5C), and combination (FIG. 5D).
Figure 5B:
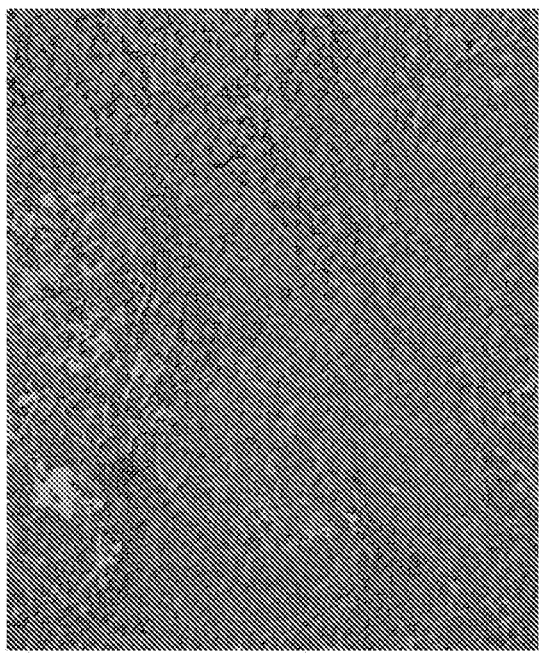
Figure 5C:
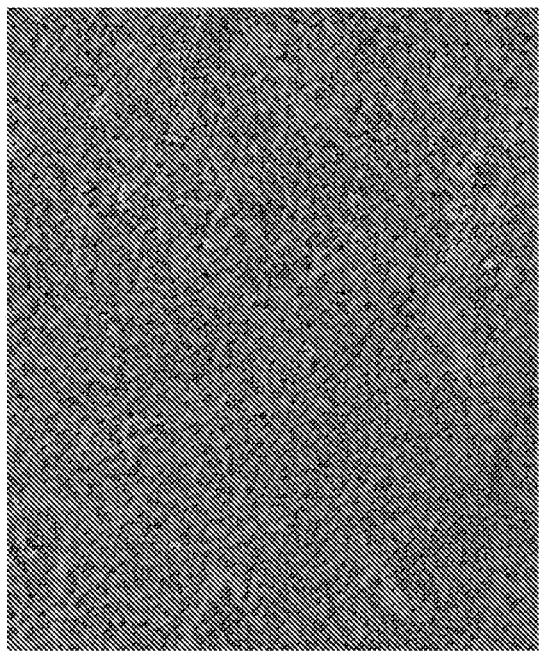
Figure 5D:
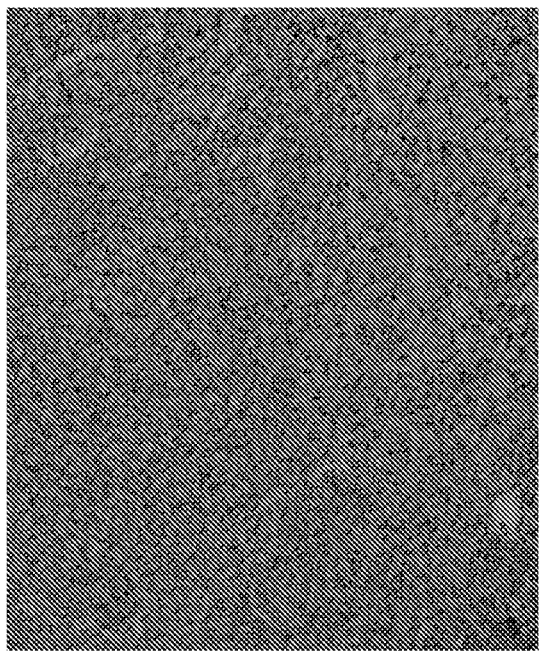

Both mouse weight and total tumor weight were measured (FIGS. 4A-3B). The mouse weight did not differ across the groups. The total tumor weight decreased in the combination group, but this decrease was not statistically significant. As a measurement of cachexia, tumor weight was divided by mouse weight (FIG. 4C). While the saline and combination group differed, the change was not statistically significant. To measure total tumor burden as a function of time to death, tumor weight was divided by the number of days the animal survived (FIG. 4D). A trend towards a difference between the controls and combination treatment groups was observed. Notably, the mice were sacrificed at different days in each group when they reached study endpoint. Though mice survived longer in the combination therapy-treated groups, their tumor burden (measured as tumor weight) may not differ dramatically compared with the tumor burden of the control mice on the day of the sacrifice.

Example 4

Figure 9:
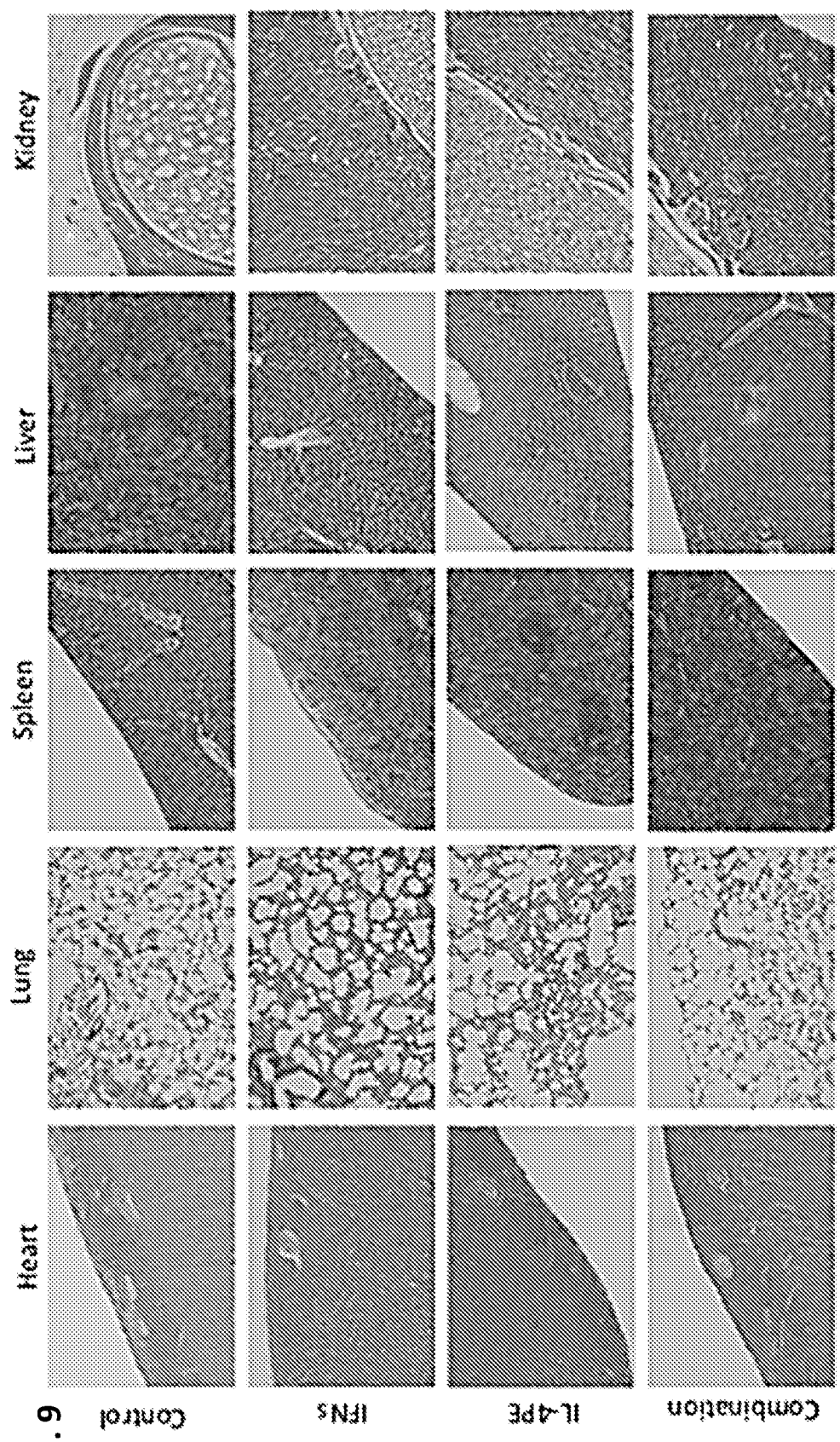
FIG. 9: Histopathology of major organs. Heart, lung, spleen, liver, and kidney were harvested from mice (control, IFNs, IL4-PE, combination) from experiments in FIGS. 3A-3B. Tissues were fixed in paraformaldehyde and embedded in paraffin. Sections were stained with H&E and analyzed for the presence of micro-metastases and the presence of necrotic or apoptotic regions potentially due to therapy toxicity. Representative images (10×) for all 5 organs and the treatment groups are shown.
Figure 10:
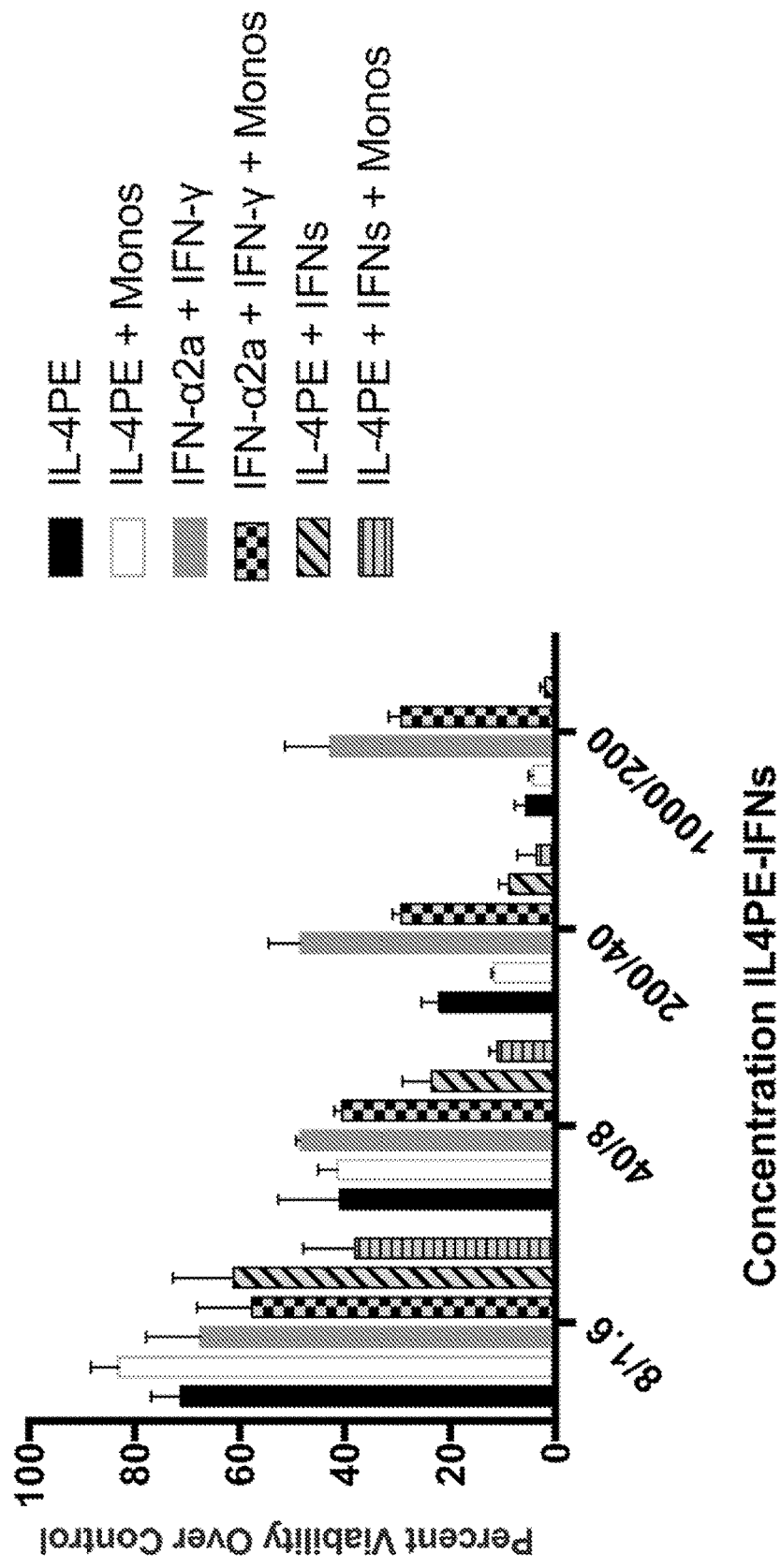
FIG. 10: Treatment of ovarian cancer cell line, OVCAR8, with IFNs, IL4-PE, human monocytes, and combinations thereof. Cells were treated with IL4-PE (black bars), IL4-PE and monocytes (open bars), IFNα and IFNγ (gray bars), the combination of IFNα, IFNγ, and IL4-PE (checker board bars), the combination of IL4-PE and IFNs (diagonal stripes bars), or the combination of IL4-PE, IFNs, and monocytes (horizontal stripes bar). Concentration are presented on the abscissae with the IL4-PE concentration (ng/ml) first and IFNs (ng/ml) concentrations second. $1 \times 10^5$ monocytes were added to each well for a final effector to target ratio of 10:1. Cell viability is presented as a percent of the control on the ordinate.

The Combination of IL4-PE, IFNα, and IFNγ Decreased Proliferation of Tumor Cells In Vivo and Did not Cause Histological Damage to Vital Organs Fixed tumor tissue sections were stained with Ki-67 and caspase-3. A marked decrease in Ki-67 staining was observed in the combination group compared with the controls, indicating a decrease in proliferation (FIGS. 5A-5D). However, no change was observed in caspase-3 activity between treatment groups (data not shown). To address potential toxicity, the major organs of the peritoneum were fixed and analyzed. An analysis of paraffin embedded tissue sections from the experiments did not show gross abnormalities, indicating that the treatment was not toxic to normal tissue (FIG. 9).

Example 5

Synergistic Effect of IL4-PE and IFNs

This example highlights the synergistic effect of IL4-PE and IFNs, showing robust activation of the IFN and IL-4 signaling pathways and subsequent activation of molecules critical for inducing apoptotic cell death.

IFNα and IFNγ signal through the IFNα and IFNγ receptors, respectively. Both receptors induce STAT1 activation through phosphorylation (Bekisz et al., *J Interferon Cytokine Res*, 33:154-161, 2013). Similarly, IL4 signals through the IL-4Rα and either the common IL-2 receptor gamma chain (IL-2Rγc) in immune cells or IL-13Rα1 chain in tumor cells to induce STAT6 activation (Murata et al., *Int J Cancer*, 70:230-240, 1997). Both STAT1 and STAT6 phosphorylation were measured in response to the IFNs, IL4-PE, or the combination of all three. IFNα and IFNγ induced STAT1 phosphorylation in both the OVCAR-5 and A2780 cell lines (FIG. 6A). IL4-PE did not induce STAT1 phosphorylation or inhibit IFN-induced STAT1 phosphorylation. IL4-PE induced STAT6 phosphorylation alone and in combination with the IFNs (FIG. 6B).

Figure 7A:
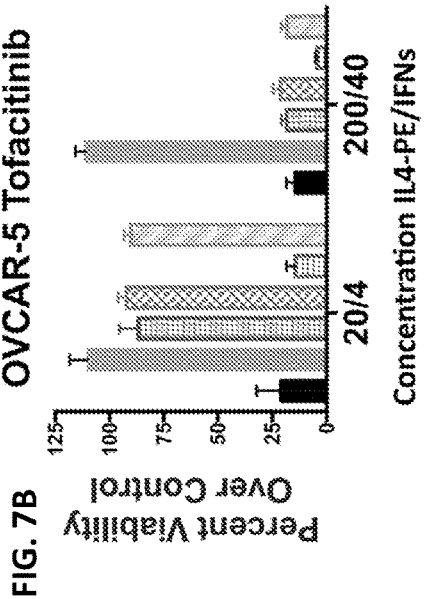
FIGS. 7A-7D: Chemical inhibition of Jak signaling. OVCAR-5 cells (FIGS. 7A-7B) or A2780 cells (FIGS. 7C-7D) were treated with either ruxolitinib or tofacitinib for 2 hours at a final concentration of 10 μm before different concentrations of IFNs, IL4-PE or the combination of each were added. Percent viability was measured after 3 days in culture.
Figure 7B:
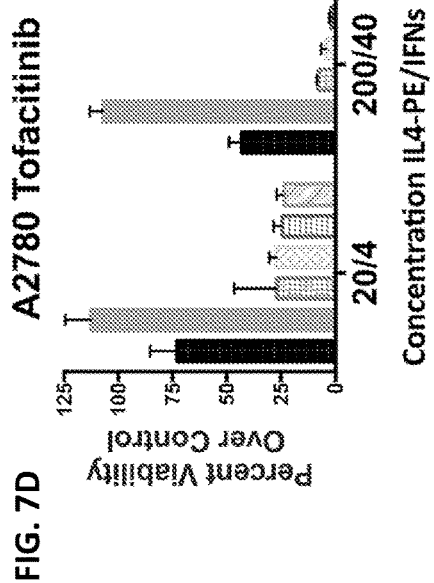
Figure 7C:
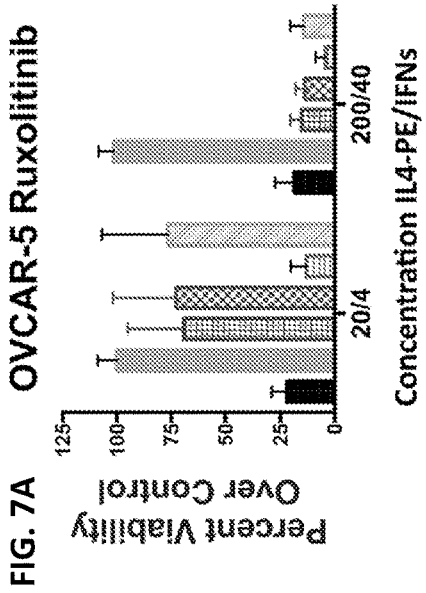
Figure 7D:
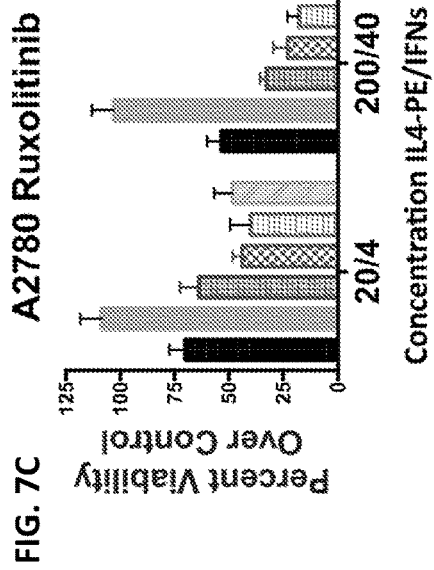

Whether IL-4Rα signal transduction through STAT6 influenced the observed synergistic killing and/or whether IFNs signaling through STAT1 influenced STAT6 mediated signaling was assessed. Two chemical inhibitors of Jak/STAT signaling were used. Ruxolitinib is an FDA-approved inhibitor of Jak1- and Jak2-mediated signaling, while tofacitinib is an FDA-approved inhibitor of Jak1 and Jak3. While the IFNs signal through Jak1 and Jak2, IL-4 can also signal through Jak1 and Jak2 in tumor cells. Ruxolitinib blocked all of the IFN and IFNs and IL4-PE mediated cell death at both 20/4 ng/mL and 200/40 ng mL IFNs/IL4-PE (FIG. 7A). However, ruxolitinib did not block any of the IL4-PE-mediated cell death. While similar ruxolitinib-mediated blocking of IFN signaling was observed in A2780 cells (FIG. 7C), adding ruxolitinib slightly increased the IL4-PE-mediated cell death. Tofacitinib experiments showed similar results as the ruxolitinib experiments in the OVCAR-5 cells (FIG. 7B), including a dose-dependent blocking of IFN signaling. Similarly, in the A2780 cells, tofacitinib blocked IFN-mediated killing at both doses, but not the IL4-PE-mediated killing in the combination treatment group (FIG. 7D). Without being bound by theory, the cell death observed may depend on IFN signaling, but not IL-4 signaling, and may act through distinct, non-redundant pathways.

To assess apoptotic cell death, PARP cleavage was measured. PARP aids in regulating the cell response to DNA damage, and PARP cleavages indicates caspase activation and inhibition of the DNA damage response. The IFNs alone, IL4-PE, or the combination of all three induced PARP cleavage in the OVCAR-5 cells as determined using western blotting (FIG. 8A). In the A2780 cell line, only PARP cleavage was observed in the IL4-PE alone or IL4-PE in combination with the IFNs (FIG. 8A). Caspase-3 is an executioner (effector) caspase that mediates protein degradation and subsequent apoptosis. In the OVCAR-5 cells, a small amount of caspase-3 activation was observed with the IL4-PE groups (Keppler-Hafkemeyer et al., *J Interferon Cytokine Res*, 33:154-161, 1998), but not the IFN groups (FIG. 8B). The A2780 cells showed a small cleavage product at 17 kDa (FIG. 8B). There was almost no presence of the whole caspase-3 at 35 kDa. Caspase-7 is also a protease that aids in apoptotic cell death. Western blot analysis showed caspase-7 cleavage in all treatment groups in OVCAR-5 cells. Caspase-7 cleavage was also evident in the A2780 cells.

Example 6

Synergistic Effect of IL4-PE, IFNs, and Monocytes

This example highlights the combination of IL4-PE and IFNs with cell-based therapies.

Co-culture of human monocytes with IFNs results in synergistic tumor cell death (Johnson et al., *J Interferon Cytokine Res*, 35:55-62, 2015). Therefore, the cytotoxicity of monocytes in combination with IFNs and IL4-PE was assayed. While the combinations of IL4-PE with monocytes and IFNs with monocytes were cytotoxic, the greatest cytotoxicity was observed with the combination of monocytes, IFNs, and IL4-PE. These data show that the combination of IFNs and IL4-PE can be combined with cell-based therapies (see also Green et al., *J Translational Medicine*, 16(1):196, 2018, assaying treatment with the IFNs and monocyte combination).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a subject with an ovarian cancer, comprising:
   administering to the subject a therapeutically effective amount of:
   (a) a chimeric molecule comprising an interleukin 4 polypeptide and a toxic moiety;
   (b) an interferon alpha (IFNα) polypeptide; and
   (c) an interferon gamma (IFNγ) polypeptide,
   thereby treating the ovarian cancer in the subject, wherein cells in the ovarian cancer express IL-4R.

2. The method of claim 1, wherein the IL-4 polypeptide is circularly permuted.

3. The method of claim 1, wherein the IL-4 polypeptide comprises an amino acid sequence at least 95% identical to SEQ ID NO: 1.

4. The method of claim 1, wherein the IL-4 polypeptide comprises the amino acid sequence of SEQ ID NO: 1.

5. The method of claim 1, wherein the toxic moiety comprises a *Pseudomonas* exotoxin (PE), ricin A, abrin, ribotoxin, ribonuclease, saporin, calicheamycin, Diphtheria toxin, botulinum toxin, pokeweed antiviral toxin, bryodin 1, *Clostridium perfringens* enterotoxin (CPE), Cholera toxin, BAD (BCL-2 associated death prompter protein), ribosome-inactivating toxins, or a cytotoxic fragment thereof.

6. The method of claim 1 wherein the toxic moiety comprises a PE polypeptide or a cytotoxic fragment thereof.

7. The method of claim 6, wherein the PE polypeptide is PE, PE38, or PE40.

8. The method of claim 1, wherein the chimeric molecule comprises a circularly permuted IL-4 and a PE or a cytotoxic fragment of the PE.

9. The method of claim 1, wherein the toxic moiety is a chemotherapeutic agent.

10. The method of claim 9, wherein the chemotherapeutic agent is taxane, carboplatin, cyclophosphamide, and/or doxorubicin.

11. The method of claim 1, wherein the IFNα and the IFNγ polypeptide are human.

12. The method of claim 2, wherein the IL-4 polypeptide, is human.

13. The method of claim 1, further comprising administering to the subject a therapeutically effective amount of surgery, chemotherapy, hormone therapy, radiation therapy, immunotherapy, and/or a vaccine.

14. The method of claim 13, wherein the immunotherapy comprises adoptive cell therapy using monocytes.

15. The method of claim 1, comprising administering the chimeric molecule; the IFNα polypeptide; and the IFNγ polypeptide, systemically to the subject.

16. The method of claim 1, comprising administering the chimeric molecule; the IFNα polypeptide; and the IFNγ polypeptide, locally to the ovarian cancer in the subject.

17. The method of claim 1, wherein the subject is a human.

* * * * *

SEQUENCE LISTING

```
<160> NUMBER OF SEQ ID NOS: 16

<210> SEQ ID NO 1
<211> LENGTH: 195
<212> TYPE: PRT
<213> ORGANISM: Homo sapiens

<400> SEQUENCE: 1

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Glu Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175
```

Leu Ser Thr Asn Met Gln Glu Arg Leu Arg Ser Lys Asp Arg Asp Leu
            180                 185                 190

Gly Ser Ser
        195

<210> SEQ ID NO 2
<211> LENGTH: 190
<212> TYPE: PRT
<213> ORGANISM: Mouse

<400> SEQUENCE: 2

Met Ala Arg Pro Phe Ala Phe Leu Met Val Leu Val Val Ile Ser Tyr
1               5                   10                  15

Trp Ser Thr Cys Ser Leu Gly Cys Asp Leu Pro Gln Thr His Asn Leu
            20                  25                  30

Arg Asn Lys Lys Ile Leu Thr Leu Leu Ala Gln Met Arg Arg Leu Ser
        35                  40                  45

Pro Leu Ser Cys Leu Lys Asp Arg Lys Asp Phe Gly Phe Pro Gln Glu
    50                  55                  60

Lys Val Asp Ala Gln Gln Ile Gln Glu Ala Gln Ala Ile Pro Val Leu
65                  70                  75                  80

Ser Glu Leu Thr Gln Gln Ile Leu Thr Leu Phe Thr Ser Lys Asp Ser
                85                  90                  95

Ser Ala Ala Trp Asn Ala Thr Leu Leu Asp Ser Phe Cys Thr Gly Leu
            100                 105                 110

His Gln Leu Leu Asn Asp Leu Gln Gly Cys Leu Met Gln Leu Val Gly
        115                 120                 125

Met Lys Glu Leu Pro Leu Thr Gln Glu Asp Ser Gln Leu Ala Met Lys
    130                 135                 140

Lys Tyr Phe His Arg Ile Thr Val Tyr Leu Arg Glu Lys His Lys Ser
145                 150                 155                 160

Pro Cys Ala Trp Glu Val Val Arg Ala Glu Val Trp Arg Ala Leu Ser
                165                 170                 175

Ser Ser Val Asn Leu Leu Ala Arg Leu Ser Glu Glu Lys Glu
            180                 185                 190

<210> SEQ ID NO 3
<211> LENGTH: 166
<212> TYPE: PRT
<213> ORGANISM: Homo sapiens

<400> SEQUENCE: 3

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

```
Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 4
<211> LENGTH: 155
<212> TYPE: PRT
<213> ORGANISM: Mouse

<400> SEQUENCE: 4

Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Asn Phe Phe Ser Asn Ser Lys Ala Lys Lys Asp Ala
            100                 105                 110

Phe Met Ser Ile Ala Lys Phe Glu Val Asn Asn Pro Gln Val Gln Arg
        115                 120                 125

Gln Ala Phe Asn Glu Leu Ile Arg Val Val His Gln Leu Ser Pro Glu
    130                 135                 140

Ser Ser Leu Arg Lys Arg Lys Arg Ser Arg Cys
145                 150                 155

<210> SEQ ID NO 5
<211> LENGTH: 863
<212> TYPE: DNA
<213> ORGANISM: Homo sapiens

<400> SEQUENCE: 5
caaggttcag agtcacccat ctcagcaagc ccagaagtat ctgcaatatc tacgatggcc      60
tcgccctttg ctttactgat ggtcctggtg gtgctcagct gcaagtcaag ctgctctctg     120
ggctgtgatc tccctgagac ccacagcctg ataacagga  ggaccttgat gctcctggca     180
caaatgagca gaatctctcc ttcctcctgt ctgatggaca acatgacttt ggatttccc      240 caggaggagt ttgatggcaa ccagttccag aaggctccag ccatctctgt cctccatgag     300
ctgatccagc agatcttcaa cctctttacc acaaaagatt catctgctgc ttgggatgag     360
gacctcctag acaaattctg caccgaactc taccagcagc tgaatgactt ggaagcctgt     420
gtgatgcagg aggagagggt gggagaaact cccctgatga atgcggactc catcttggct     480
gtgaagaaat acttccgaag aatcactctc tatctgacag agaagaaata cagcccttgt     540
gcctgggagg ttgtcagagc agaaatcatg agatccctct ctttatcaac aaacttgcaa     600
gaaagattaa ggaggaagga ataacatctg gtccaacatg aaaacaattc ttattgactc     660
```

-continued

| | |
|---|---|
| atacaccagg tcacgctttc atgaattctg tcatttcaaa gactctcacc cctgctataa | 720 |
| ctatgaccat gctgataaac tgatttatct atttaaatat ttatttaact attcataaga | 780 |
| tttaaattat ttttgttcat ataacgtcat gtgcaccttt acactgtggt tagtgtaata | 840 |
| aaacatgttc cttatattta ctc | 863 |

<210> SEQ ID NO 6
<211> LENGTH: 570
<212> TYPE: DNA
<213> ORGANISM: Mouse

<400> SEQUENCE: 6

| | |
|---|---|
| atggctaggc tctgtgcttt cctgatggtc ctggcggtgc tgagctactg gccaacctgc | 60 |
| tctctaggat gtgaccttcc tcagactcat aacctcagga caagagagc cttgacactc | 120 |
| ctggtacaaa tgaggagact ctcccctctc tcctgcctga aggacaggaa ggactttgga | 180 |
| ttcccgcagg agaaggtgga tgcccagcag atcaagaagg ctcaagccat ccctgtcctg | 240 |
| agtgagctga cccagcagat cctgaacatc ttcacatcaa aggactcatc tgctgcatgg | 300 |
| aatacaaccc tcctagactc attctgcaat gacctccacc agcagctcaa tgacctgcaa | 360 |
| ggctgtctga tgcagcaggt gggggtgcag gaatttcccc tgacccagga gatgccctg | 420 |
| ctggctgtga ggaaatactt ccacaggatc actgtgtacc tgagagagaa gaaacacagc | 480 |
| ccctgtgcct gggaggtggt cagagcagaa gtctggagag ccctgtcttc ctctgccaat | 540 |
| gtgctgggaa gactgagaga agagaaatga | 570 |

<210> SEQ ID NO 7
<211> LENGTH: 1240
<212> TYPE: DNA
<213> ORGANISM: Homo sapiens

<400> SEQUENCE: 7

| | |
|---|---|
| cacattgttc tgatcatctg aagatcagct attagaagag aaagatcagt taagtccttt | 60 |
| ggacctgatc agcttgatac aagaactact gatttcaact tctttggctt aattctctcg | 120 |
| gaaacgatga atatacaag ttatatcttg gcttttcagc tctgcatcgt tttgggttct | 180 |
| cttggctgtt actgccagga cccatatgta aagaagcag aaaaccttaa gaaatatttt | 240 |
| aatgcaggtc attcagatgt agcggataat ggaactcttt tcttaggcat tttgaagaat | 300 |
| tggaaagagg agagtgacag aaaaataatg cagagccaaa ttgtctcctt ttacttcaaa | 360 |
| ctttttaaaa actttaaaga tgaccagagc atccaaaaga gtgtggagac catcaaggaa | 420 |
| gacatgaatg tcaagttttt caatagcaac aaaaagaaac gagatgactt cgaaaagctg | 480 |
| actaattatt cggtaactga cttgaatgtc aacgcaaag caatacatga actcatccaa | 540 |
| gtgatggctg aactgtcgcc agcagctaaa acagggaagc gaaaaaggag tcagatgctg | 600 |
| tttcgaggtc gaagagcatc ccagtaatgg ttgtcctgcc tgcaatattt gaattttaaa | 660 |
| tctaaatcta tttattaata tttaacatta tttatatggg gaatatattt ttagactcat | 720 |
| caatcaaata agtatttata atagcaactt ttgtgtaatg aaaatgaata tctattaata | 780 |
| tatgtattat ttataattcc tatatcctgt gactgtctca cttaatcctt tgttttctga | 840 |
| ctaattaggc aaggctatgt gattacaagg ctttatctca ggggccaact aggcagccaa | 900 |
| cctaagcaag atcccatggg ttgtgtgttt atttcacttg atgatacaat gaacacttat | 960 |
| aagtgaagtg atactatcca gttactgccg gtttgaaaat atgcctgcaa tctgagccag | 1020 |
| tgctttaatg gcatgtcaga cagaacttga atgtgtcagg tgaccctgat gaaaacatag | 1080 |

-continued

```
catctcagga gatttcatgc ctggtgcttc caaatattgt tgacaactgt gactgtaccc    1140
aaatggaaag taactcattt gttaaaatta tcaatatcta atatatatga ataaagtgta    1200
agttcacaac aaaaaaaaaa aaaaaaaaaa aaaaaaaaa                           1240
```

<210> SEQ ID NO 8
<211> LENGTH: 1210
<212> TYPE: DNA
<213> ORGANISM: Mouse

<400> SEQUENCE: 8

```
tatagctgcc atcggctgac ctagagaaga cacatcagct gatcctttgg accctctgac      60
ttgagacaga agttctgggc ttctcctcct gcggcctagc tctgagacaa tgaacgctac     120
acactgcatc ttggctttgc agctcttcct catggctgtt tctggctgtt actgccacgg     180
cacagtcatt gaaagcctag aaagtctgaa taactatttt aactcaagtg gcatagatgt     240
ggaagaaaag agtctcttct tggatatctg gaggaactgg caaaaggatg gtgacatgaa     300
aatcctgcag agccagatta tctctttcta cctcagactc tttgaagtct tgaaagacaa     360
tcaggccatc agcaacaaca taagcgtcat tgaatcacac ctgattacta ccttcttcag     420
caacagcaag gcgaaaaagg atgcattcat gagtattgcc aagtttgagg tcaacaaccc     480
acaggtccag cgccaagcat tcaatgagct catccgagtg gtccaccagc tgttgccgga     540
atccagcctc aggaagcgga aaaggagtcg ctgctgattc ggggtgggga agagattgtc     600
ccaataagaa taattctgcc agcactattt gaatttttaa atctaaacct atttattaat     660
atttaaaact atttatatgg agaatctatt ttagatgcat caaccaaaga agtatttata     720
gtaacaactt atatgtgata agagtgaatt cctattaata tatgtgttat ttataatttc     780
tgtctcctca actatttctc tttgaccaat taattattct ttctgactaa ttagccaaga     840
ctgtgattgc ggggttgtat ctgggggtgg gggacagcca agcggctgac tgaactcaga     900
ttgtagcttg tacctttact tcactgacca ataagaaaca ttcagagctg cagtgacccc     960
gggaggtgct gctgatggga ggagatgtct acactccggg ccagcgcttt aacagcaggc    1020
cagacagcac tcgaatgtgt caggtagtaa caggctgtcc ctgaaagaaa gcagtgtctc    1080
aagagacttg acacctggtg cttccctata cagctgaaaa ctgtgactac acccgaatga    1140
caaataactc gctcatttat agtttatcac tgtctaattg catatgaata aagtatacct    1200
ttgcaaccaa                                                           1210
```

<210> SEQ ID NO 9
<211> LENGTH: 153
<212> TYPE: PRT
<213> ORGANISM: Homo sapiens

<400> SEQUENCE: 9

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
        50                  55                  60

Glu Lys Glu Thr Phe Cys Arg Ala Ala Thr Val Leu Arg Gln Phe Tyr
65                  70                  75                  80
```

Ser His His Glu Lys Asp Thr Arg Cys Leu Gly Ala Thr Ala Gln Gln
                85                      90                      95

Phe His Arg His Lys Gln Leu Ile Arg Leu Leu Lys Arg Leu Asp Arg
             100                     105                     110

Asn Leu Trp Gly Leu Ala Gly Leu Asn Ser Cys Pro Val Lys Glu Ala
             115                     120                     125

Asn Gln Ser Thr Leu Glu Asn Phe Leu Glu Arg Leu Lys Thr Ile Met
             130                     135                     140

Arg Glu Lys Tyr Ser Lys Cys Ser Ser
145              150

<210> SEQ ID NO 10
<211> LENGTH: 140
<212> TYPE: PRT
<213> ORGANISM: Mouse

<400> SEQUENCE: 10

Met Gly Leu Asn Pro Gln Leu Val Val Ile Leu Leu Phe Phe Leu Glu
1             5                     10                     15

Cys Thr Arg Ser His Ile His Gly Cys Asp Lys Asn His Leu Arg Glu
             20                     25                     30

Ile Ile Gly Ile Leu Asn Glu Val Thr Gly Glu Gly Thr Pro Cys Thr
         35                     40                     45

Glu Met Asp Val Pro Asn Val Leu Thr Ala Thr Lys Asn Thr Thr Glu
50                     55                     60

Ser Glu Leu Val Cys Arg Ala Ser Lys Val Leu Arg Ile Phe Tyr Leu
65                     70                     75                     80

Lys His Gly Lys Thr Pro Cys Leu Lys Lys Asn Ser Ser Val Leu Met
             85                     90                     95

Glu Leu Gln Arg Leu Phe Arg Ala Phe Arg Cys Leu Asp Ser Ser Ile
             100                     105                     110

Ser Cys Thr Met Asn Glu Ser Lys Ser Thr Ser Leu Lys Asp Phe Leu
             115                     120                     125

Glu Ser Leu Lys Ser Ile Met Gln Met Asp Tyr Ser
             130                     135                     140

<210> SEQ ID NO 11
<211> LENGTH: 614
<212> TYPE: DNA
<213> ORGANISM: Homo sapiens

<400> SEQUENCE: 11
gatcgttagc ttctcctgat aaactaattg cctcacattg tcactgcaaa tcgacaccta    60
ttaatgggtc tcacctccca actgcttccc cctctgttct tcctgctagc atgtgccggc   120
aactttgtcc acggacacaa gtgcgatatc accttacagg agatcatcaa actttgaac   180 agcctcacag agcagaagac tctgtgcacc gagttgaccg taacagacat ctttgctgcc   240
tccaagaaca caactgagaa ggaaaccttc tgcagggctg cgactgtgct ccggcagttc   300
tacagccacc atgagaagga cactcgctgc ctgggtgcga ctgcacagca gttccacagg   360
cacaagcagc tgatccgatt cctgaaacgg ctcgacagga acctctgggg cctggcgggc   420
ttgaattcct gtcctgtgaa ggaagccaac cagagtacgt tggaaaactt cttggaaagg   480
ctaaagacga tcatgagaga gaaatattca aagtgttcga gctgaatatt ttaatttatg   540 agttttgat agctttattt tttaagtatt tatatattta taactcatca taaaataaag   600
tatatataga atct   614

<210> SEQ ID NO 12
<211> LENGTH: 605
<212> TYPE: DNA
<213> ORGANISM: Mouse

<400> SEQUENCE: 12

```
ggatccccgg gcagagctgg gggggatttt gttagcatct cttgataaac ttaattgtct      60
ctcgtcactg acggcacaga gctattgatg ggtctcaacc cccagctagt tgtcatcctg     120
ctcttctttc tcgaatgtac caggagccat atccacggat gcgacaaaaa tcacttgaga     180
gagatcatcg gcattttgaa cgaggtcaca ggagaaggga cgccatgcac ggagatggat     240
gtgccaaacg tcctcacagc aacgaagaac accacagaga gtgagctcgt ctgtagggct     300
tccaaggtgc ttcgcatatt ttatttaaaa catgggaaaa ctccatgctt gaagaagaac     360
tctagtgttc tcatggagct gcagagactc tttcgggctt ttcgatgcct ggattcatcg     420
ataagctgca ccatgaatga gtccaagtcc acatcactga aagacttcct ggaaagccta     480
aagagcatca tgcaaatgga ttactcgtag tactgagcca ccatgcttta acttatgaat     540
ttttaatggt tttattttaa tatttatata tttataattc ataaaataaa atatttgtat     600
aatgt                                                                605
```

<210> SEQ ID NO 13
<211> LENGTH: 638
<212> TYPE: PRT
<213> ORGANISM: Artificial Sequence
<220> FEATURE:
<223> OTHER INFORMATION: PE

<400> SEQUENCE: 13

```
Met His Leu Thr Pro His Trp Ile Pro Leu Val Ala Ser Leu Gly Leu
1               5                   10                  15

Leu Ala Gly Gly Ser Phe Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Ala Gln Pro Arg Arg
        195                 200                 205
```

```
Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Gly Ala Ala Ser Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Ile
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Gly Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605
```

```
Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635

<210> SEQ ID NO 14
<211> LENGTH: 1917
<212> TYPE: DNA
<213> ORGANISM: Artificial Sequence
<220> FEATURE:
<223> OTHER INFORMATION: PE

<400> SEQUENCE: 14
atgcacctga tacccattg gatccccctg gtcgccagcc tcggcctgct cgccggcggc      60
tcgttcgcgt ccgccgccga ggaagccttc gacctctgga cgaatgcgc caaggcctgc    120 gtgctcgacc tcaaggacgg cgtgcgttcc agccgcatga gcgtcgaccc ggccatcgcc    180
gacaccaacg gccagggcgt gctgcactac tccatggtcc tggagggcgg caacgacgcg    240
ctcaagctgg ccatcgacaa cgccctcagc atcaccagcg acggcctgac catccgcctc    300
gaaggcggcg tcgagccgaa caagccggtg cgctacagct acacgcgcca ggcgcgcggc    360
agttggtcgc tgaactggct ggtgccgatc ggccacgaga agccttcgaa catcaaggtg    420
ttcatccacg aactgaacgc cggtaaccag ctcagccaca tgtcgccgat ctacaccatc    480
gagatgggcg acgagttgct ggcgaagctg gcgcgcgatg ccaccttctt cgtcagggcg    540
cacgagagca acgagatgca ccgacgctc gccatcagcc atgccggggt cagcgtggtc    600
atggcccagg cccagccgcg ccgggaaaag cgctggagcg aatgggccag cggcaaggtg    660
ttgtgcctgc tcgacccgct ggacggggtc tacaactacc tcgcccagca cgctgcaac     720 ctcgacgata cctgggaagg caagatctac cgggtgctcg ccggcaaccc ggcgaagcat    780
gacctggaca tcaagcccac ggtcatcagt catcgcctgc acttccccga gggcggcagc    840
ctggccgcgc tgaccgcgca ccaggcttgc cacctgccgc tggagacctt cacccgtcat    900
cgccagccgc gcggctggga caactggag cagtgcggct atccggtgca cggctggtc     960 gccctctacc tggcggcgcg actgtcgtgg aaccaggtcg accaggtgat ccgcaacgcc   1020
ctggccagcc ccggcagcgg cggcgacctg gcgaagcga tccgcgagca gccggagcag   1080
gcccgtctgg ccctgaccct ggccgccgcc gagagcgagc gcttcgtccg cagggcacc   1140 ggcaacgacg aggccggcgc ggccagcgcc gacgtggtga gctgacctg cccggtcgcc   1200 gccggtgaat gcgcgggccc ggcggacagc ggcgacgccc tgctggagcg caactatccc   1260
actggcgcgg agttcctcgg cgacggcggc gacgtcagct tcagcacccg cggcacgcag   1320
aactggacgg tggagcggct gctccaggcg caccgccaac tggaggagcg cggctatgta   1380 tcgtcggct accacggcac cttcctcgaa gcggcgcaaa gcatcgtctt cggcggggtg   1440
cgcgcgcgca gccaggacct cgacgcgatc tggcgcggtt tctatatcgc cggcgatccg   1500
gcgctggcct acggctacgc ccaggaccag gaacccgacg cgcgcggccg gatccgcaac   1560
ggtgccctgc tgcgggtcta tgtgccgcgc tcgagcctgc cgggcttcta ccgcaccggc   1620 ctgacccctgg ccgcgccgga ggcggcgggc gaggtcgaac ggctgatcgg ccatccgctg   1680
ccgctgcgcc tggacgccat caccggcccc gaggaggaag cgggcgcct ggagaccatt   1740 ctcggctggc cgctggccga gcgaccgtg gtgattccct cggcgatccc caccgacccg   1800
cgcaacgtcg gcgcgacct cgaccgtcc agcatccccg acaaggaaca ggcgatcagc   1860
gccctgccgg actacgccag ccagcccggc aaaccgccgc gcgaggacct gaagtaa     1917
```

<210> SEQ ID NO 15
<211> LENGTH: 480
<212> TYPE: PRT
<213> ORGANISM: Artificial Sequence
<220> FEATURE:
<223> OTHER INFORMATION: IL4-PE38KDEL

<400> SEQUENCE: 15

```
His Met Asp Thr Thr Glu Lys Glu Thr Phe Cys Arg Ala Ala Thr Val
1               5                   10                  15

Leu Arg Gln Phe Tyr Ser His His Glu Lys Asp Thr Arg Cys Leu Gly
                20                  25                  30

Ala Thr Ala Gln Gln Phe His Arg His Lys Gln Leu Ile Arg Phe Leu
            35                  40                  45

Lys Arg Leu Asp Arg Asn Leu Trp Gly Leu Ala Gly Leu Asn Ser Cys
        50                  55                  60

Pro Val Lys Glu Ala Asn Gln Ser Thr Leu Glu Asn Phe Leu Glu Arg
65                  70                  75                  80

Leu Lys Thr Ile Met Arg Glu Lys Tyr Ser Lys Cys Ser Ser Lys Cys
                85                  90                  95

Asp Ile Thr Leu Gln Glu Ile Ile Lys Thr Leu Asn Ser Leu Thr Glu
                100                 105                 110

Gln Lys Thr Leu Cys Thr Glu Leu Thr Val Thr Asp Ile Phe Ala Ala
            115                 120                 125

Ser Lys Ala Ser Gly Gly Pro Glu Gly Gly Ser Leu Ala Ala Leu Thr
        130                 135                 140

Ala His Gln Ala Cys His Leu Pro Leu Glu Thr Phe Thr Arg His Arg
145                 150                 155                 160

Gln Pro Arg Gly Trp Glu Gln Leu Glu Gln Cys Gly Tyr Pro Val Gln
                165                 170                 175

Arg Leu Val Ala Leu Tyr Leu Ala Ala Arg Leu Ser Trp Asn Gln Val
                180                 185                 190

Asp Gln Val Ile Arg Asn Ala Leu Ala Ser Pro Gly Ser Gly Gly Asp
            195                 200                 205

Leu Gly Glu Ala Ile Arg Glu Gln Pro Glu Gln Ala Arg Leu Ala Leu
        210                 215                 220

Thr Leu Ala Ala Ala Glu Ser Glu Arg Phe Val Arg Gln Gly Thr Gly
225                 230                 235                 240

Asn Asp Glu Ala Gly Ala Ala Asn Gly Pro Ala Asp Ser Gly Asp Ala
                245                 250                 255

Leu Leu Glu Arg Asn Tyr Pro Thr Gly Ala Glu Phe Leu Gly Asp Gly
                260                 265                 270

Gly Asp Val Ser Phe Ser Thr Arg Gly Thr Gln Asn Trp Thr Val Glu
            275                 280                 285

Arg Leu Leu Gln Ala His Arg Gln Leu Glu Glu Arg Gly Tyr Val Phe
        290                 295                 300

Val Gly Tyr His Gly Thr Phe Leu Glu Ala Ala Gln Ser Ile Val Phe
305                 310                 315                 320

Gly Gly Val Arg Ala Arg Ser Gln Asp Leu Asp Ala Ile Trp Arg Gly
                325                 330                 335

Phe Tyr Ile Ala Gly Asp Pro Ala Leu Ala Tyr Gly Tyr Ala Gln Asp
                340                 345                 350
```

| | | | | | | | | | | | |
|---|---|---|---|---|---|---|---|---|---|---|---|
|Gln|Glu|Pro|Asp|Ala|Arg|Gly|Arg|Ile|Arg|Asn|Gly|Ala|Leu|Leu|Arg|
| | |355| | | |360| | | |365| |

Val Tyr Val Pro Arg Ser Ser Leu Pro Gly Phe Tyr Arg Thr Ser Leu
    370              375              380

Thr Leu Ala Ala Pro Glu Ala Ala Gly Glu Val Glu Arg Leu Ile Gly
385              390              395              400

His Pro Leu Pro Leu Arg Leu Asp Ala Ile Thr Gly Pro Glu Glu Glu
            405              410              415

Gly Gly Arg Leu Glu Thr Ile Leu Gly Trp Pro Leu Ala Glu Arg Thr
            420              425              430

Val Val Ile Pro Ser Ala Ile Pro Thr Asp Pro Arg Asn Val Gly Gly
            435              440              445

Asp Leu Asp Pro Ser Ser Ile Pro Asp Lys Glu Gln Ala Ile Ser Ala
    450              455              460

Leu Pro Asp Tyr Ala Ser Gln Pro Gly Lys Pro Pro Lys Asp Glu Leu
465              470              475              480

<210> SEQ ID NO 16
<211> LENGTH: 1482
<212> TYPE: DNA
<213> ORGANISM: Artificial Sequence
<220> FEATURE:
<223> OTHER INFORMATION: IL4-PE38KDEL

<400> SEQUENCE: 16

```
catatggaca caactgagaa ggaaaccttc tgcagggctg cgactgtgct ccggcagttc      60
tacagccacc atgagaagga cactcgctgc ctgggtgcga ctgcacagca gttccacagg     120
cacaagcagc tgatccgatt cctgaaacgg ctcgacagga acctctgggg cctggcgggc    180
ttgaattcct gtcctgtgaa ggaagccaac cagagtacgt ggaaaacttc ttggaaaagg    240
ctaaagacga tcatgagaga gaaatattca agtgttcgt ccaagtgcga tatcacctta    300
caggagatca tcaaaacttt gaacagcctc acagagcaga agactctgtg caccgagttg    360
accgtaacag acatctttgc tgcctccaaa gcttccggag gtcccgaggg cggcagcctg    420
gccgcgctga ccgcgcacca ggcttgccac ctgccgctgg agactttcac ccgtcatcgc    480
cagccgcgcg gctgggaaca actggagcag tgcggctatc cggtgcagcg gctggtcgcc    540
ctctacctgg cggcgcggct gtcgtggaac caggtcgacc aggtgatccg caacgccctg    600
gccagccccg gcagcggcgg cgacctgggc gaagcgatcc gcgagcagcc ggagcaggcc    660
cgtctggccc tgaccctggc cgccgccgag agcgagcgct cgtccggca gggcaccggc    720
aacgacgagg ccggcgcggc caacggcccg gcggacagcg gcgacgccct gctggagcgc    780
aactatccca ctggcgcgga gttcctcggc gacggcggcg acgtcagctt cagcacccgc    840
ggcacgcaga actggacggt ggagcggctg ctccaggcgc accgccaact ggaggagcgc    900
ggctatgtgt tcgtcggcta ccacggcacc ttcctcgaag cggcgcaaag catcgtcttc    960
ggcggggtgc gcgcgcgcag ccaggacctc gacgcgatct ggcgcggttt ctatatcgcc   1020
ggcgatccgg cgctggccta cggctacgcc caggaccagg aacccgacgc acgcggccgg   1080
atccgcaacg gtgccctgct gcgggtctat gtgccgcgct cgagcctgcc gggcttctac   1140
cgcaccagcc tgaccctggc cgcgccggag gcggcgggcg aggtcgaacg gctgatcggc   1200
catccgctgc cgctgcgcct ggacgccatc accggccccg aggaggaagg cgggcgcctg   1260
gagaccattc tcggctggcc gctggccgag cgcaccgtgg tgattccctc ggcgatcccc   1320
accgacccgc gcaacgtcgg cggcgacctc gacccgtcca gcatccccga caaggaacag   1380
```

```
gcgatcagcg ccctgccgga ctacgccagc cagcccggca aaccgccgaa agacgagctc    1440
taagaattcg gctgctaaca aagcccgaaa ggaagctgag tt                       1482
```